US011918807B2

(12) United States Patent
Toth et al.

(10) Patent No.: US 11,918,807 B2
(45) Date of Patent: *Mar. 5, 2024

(54) MONITORING AND MANAGEMENT OF PHYSIOLOGIC PARAMETERS OF A SUBJECT

(71) Applicant: LifeLens Technologies, Inc., Ivyland, PA (US)

(72) Inventors: Landy Toth, Doylestown, PA (US); Robert S. Schwartz, Inver Grove Heights, MN (US); Beth Schwartz, Inver Grove Heights, MN (US)

(73) Assignee: LifeLens Technologies, LLC, Ivyland, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/837,179

(22) Filed: Jun. 10, 2022

(65) Prior Publication Data

US 2022/0313996 A1    Oct. 6, 2022

Related U.S. Application Data

(63) Continuation of application No. 16/097,216, filed as application No. PCT/US2017/030186 on Apr. 28, 2017, now Pat. No. 11,389,652.

(Continued)

(51) Int. Cl.
*A61N 1/36* (2006.01)
*A43B 3/34* (2022.01)
(Continued)

(52) U.S. Cl.
CPC ........... *A61N 1/36034* (2017.08); *A43B 3/34* (2022.01); *A43B 3/36* (2022.01); *A43B 3/50* (2022.01);
(Continued)

(58) Field of Classification Search
CPC ................ A61N 1/36034; A61N 1/36031
(Continued)

(56) References Cited

U.S. PATENT DOCUMENTS 7,041,049 B1    5/2006  Raniere
7,146,211 B2   12/2006  Frei et al.
(Continued)

FOREIGN PATENT DOCUMENTS

| CN | 202699824 U | 1/2013 |
| WO | 2014197822 A2 | 12/2014 |
| WO | 2016019250 A1 | 2/2016 |

OTHER PUBLICATIONS

India Examination Report for Patent Application No. 201847044418, dated Nov. 5, 2021, 4 pages.
(Continued)

*Primary Examiner* — Nadia A Mahmood
(74) *Attorney, Agent, or Firm* — Ryan, Mason & Lewis, LLP

(57) ABSTRACT

A method includes receiving monitoring data from at least one sensing device coupled to a subject and analyzing the monitoring data to identify one or more physiologic parameters of the subject. The method also includes providing signaling to at least one stimulating device in response to the identified physiologic parameters, the signaling comprising instructions to apply a stimulus to the subject. The method further includes receiving additional monitoring data from the at least one sensing device, analyzing the additional monitoring data to identify one or more changes in the one or more physiologic parameters of the subject after application of the stimulus to the subject, and providing additional signaling to the at least one stimulating device, the additional signaling comprising instructions to modify the
(Continued)

stimulus applied to the subject based on the identified changes in the one or more physiologic parameters.

20 Claims, 21 Drawing Sheets

Related U.S. Application Data

(60) Provisional application No. 62/453,012, filed on Feb. 1, 2017, provisional application No. 62/329,358, filed on Apr. 29, 2016.

(51) Int. Cl.
| | |
|---|---|
| *A43B 3/36* | (2022.01) |
| *A43B 3/50* | (2022.01) |
| *A43B 7/1455* | (2022.01) |
| *A43B 17/00* | (2006.01) |
| *A61B 5/00* | (2006.01) |
| *A61B 5/0205* | (2006.01) |
| *A61N 1/04* | (2006.01) |
| *A61N 1/08* | (2006.01) |
| *A61B 5/145* | (2006.01) |
| *A61B 5/318* | (2021.01) |
| *A61B 5/369* | (2021.01) |
| *A61B 5/389* | (2021.01) |

(52) U.S. Cl.
CPC .............. *A43B 7/146* (2013.01); *A43B 17/00* (2013.01); *A61B 5/0024* (2013.01); *A61B 5/02055* (2013.01); *A61B 5/4818* (2013.01); *A61B 5/4836* (2013.01); *A61N 1/0452* (2013.01); *A61N 1/0456* (2013.01); *A61N 1/0472* (2013.01); *A61N 1/0484* (2013.01); *A61N 1/0492* (2013.01); *A61N 1/08* (2013.01); *A61N 1/36* (2013.01); *A61N 1/36003* (2013.01); *A61N 1/36014* (2013.01); *A61N 1/36031* (2017.08); *A61B 5/145* (2013.01); *A61B 5/318* (2021.01); *A61B 5/369* (2021.01); *A61B 5/389* (2021.01); *A61B 5/681* (2013.01); *A61B 5/688* (2013.01); *A61B 5/6892* (2013.01); *A61N 1/0496* (2013.01); *A61N 1/36036* (2017.08); *A61N 1/3604* (2017.08)

(58) Field of Classification Search
USPC .......................................... 600/301
See application file for complete search history.

(56) References Cited

U.S. PATENT DOCUMENTS

| | | |
|---|---|---|
| 2005/0149133 A1 | 7/2005 | Libbus et al. |
| 2007/0191688 A1* | 8/2007 | Lynn .................... A61B 5/4818 600/300 |
| 2011/0065979 A1 | 3/2011 | Lehrman et al. |
| 2012/0316616 A1 | 12/2012 | Kokones et al. |
| 2015/0351690 A1 | 12/2015 | Toth et al. |

OTHER PUBLICATIONS

European Extended Search Report for Patent Application No. 17790573, dated Nov. 8, 2019, 7 pages.

International Search Report and Written Opinion of the International Searching Authority of PCT/US2017/030186, dated Jul. 19, 2017, 16 pages.

* cited by examiner

MONITORING AND MANAGEMENT OF PHYSIOLOGIC PARAMETERS OF A SUBJECT

CROSS-REFERENCE TO RELATED APPLICATIONS

The present application is a continuation of U.S. patent application Ser. No. 16/097,216, filed on Oct. 26, 2018, which is a national stage application of International Application PCT/US2017/30186, filed on Apr. 28, 2017, which claims the benefit of and priority to U.S. Provisional Application Ser. No. 62/329,358, filed on Apr. 29, 2016, and to U.S. Provisional Application Ser. No. 62/453,012, filed on Feb. 1, 2017, the entire contents of which are incorporated by reference herein for all purposes.

TECHNICAL FIELD

The present disclosure relates to the field of physiologic monitoring and, more particularly, to devices and systems for monitoring and/or management of physiologic parameters of a subject.

BACKGROUND

Physiologic monitoring is performed for a range of purposes. Existing technologies, however, are not without shortcomings.

There is a need to measure physiologic parameters of subjects, reliably, simply, and without cables. As the proliferation of mobile and remote medicine increases, simplified and unobtrusive means for monitoring the physiologic parameters of a patient become more important.

Patient compliance is critical to the success of such systems and is often directly correlated to the ease of use and unobtrusiveness of the monitoring solution used.

Existing monitoring systems are often prone to false alarms, usage related failures, unreliable user interfaces, cumbersome interfaces, artifact or electromagnetic interference (EMI) related interference, etc. Such problems decrease productivity of using these systems, can result in lost data, and lead to dissatisfaction on the part of both the subject being monitored and the practitioners monitoring the subject. In the case of a hospital setting, the continual drone of alarms can lead to alarm fatigue and decreased productivity.

Long term compliance of subjects may suffer due to uncomfortable interfaces with monitoring devices, involved maintenance or change-over of disposables, painful or itchy reactions to materials in the devices, and the like.

More reliable, redundant, and user friendly systems are needed that can provide valuable patient data even when operating with limited supervision, expert input, or user manipulation.

SUMMARY

One illustrative, non-limiting objective of this disclosure is to provide systems, devices, methods, and kits for monitoring and management of physiologic parameters of a subject. Another illustrative, non-limiting objective is to provide simplified system for monitoring subjects. Another illustrative, non-limiting objective is to provide comfortable long term wearable systems for monitoring subjects. Yet another illustrative, non-limiting objective is to provide systems for facilitating stimulation of a subject based on monitoring physiologic parameters of the subject.

The above illustrative, non-limiting objectives are wholly or partially met by devices, systems, and methods according to the appended claims in accordance with the present disclosure. Features and aspects are set forth in the appended claims, in the following description, and in the annexed drawings in accordance with the present disclosure.

In some embodiments, a method comprises receiving monitoring data from at least one sensing device coupled to a subject, analyzing the monitoring data to identify one or more physiologic parameters of the subject and providing signaling to at least one stimulating device in response to the identified physiologic parameters, the signaling comprising instructions to apply a stimulus to the subject. The method also comprises receiving additional monitoring data from the at least one sensing device, analyzing the additional monitoring data to identify one or more changes in the one or more physiologic parameters of the subject after application of the stimulus to the subject, and providing additional signaling to the at least one stimulating device, the additional signaling comprising instructions to modify the stimulus applied to the subject based on the identified changes in the one or more physiologic parameters. The method is performed by at least one processing device comprising a processor coupled to a memory.

In some embodiments, the at least one processing device comprises a host device wirelessly coupled to the at least one sensing device and the at least one stimulating device.

In some embodiments, the stimulus comprises an electrical stimulus. The electrical stimulus may comprise application of a pulse train. The pulse train may comprise a variable or a fixed repetition rate. The pulse train in some embodiments comprises at least one pulse having a duration between 10 and 20 microseconds and/or a total charge between 10 and 20 microcoulombs. The pulse train may comprise two or more pulses having duration and charge delivery sufficient to stimulate tactile sensation while limiting pain fiber stimulation. The additional signaling comprises instructions to modify at least one of a duration of at least one pulse in the pulse train and a total charge of the at least one pulse in the pulse train. In some embodiments, the pulse train when applied to the subject mimics another stimulus, the other stimulus comprising at least one of vibration, pain, a wet sensation, heat or cold, taste, tension or stretch, sound, pressure and light. In some embodiments, the pulse train is applied to the subject to amplify another stimulus, the other stimulus comprising at least one of vibration, pain, a wet sensation, heat or cold, taste, tension or stretch, sound pressure and light.

In some embodiments, the stimulating device comprises a plurality of electrodes, and the signaling comprises instructions to selectively activate the plurality of electrodes in different locations in a test pattern and to utilize one or more sensors in at least one of the sensing device and the stimulating device to measure a response of the subject to the stimulus at the different locations in the test pattern. The additional signaling may comprise instructions to apply a stimulus using one or more of the plurality of electrodes at a given location based on the measured response of the subject to the stimulus at the different locations in the test pattern.

In some embodiments, analyzing the monitoring data comprises detecting an event based on measured levels of the one or more physiologic parameters, and wherein the stimulus comprises a therapeutic stimulus to remedy the event. The event may comprise a sleep apneic event, and the therapeutic stimulus may comprise application of stimulus to a plantar aspect of a foot of the subject. The event may comprise determining a sleep posture of the subject, and the therapeutic stimulus may comprise application of stimulus to alter the sleep posture of the subject.

In some embodiments, analyzing the monitoring data comprises detecting one or more measured values of physiologic parameters indicating that an event is likely to occur, and the stimulus comprises a therapeutic stimulus to reduce a likelihood that the event will occur.

In some embodiments, the at least one sensing device and the at least one stimulating device are physically distinct.

In some embodiments, the at least one sensing device comprises a first sensing device at a first location on the subject and a second sensing device at a second location on the subject different than the first location. The first sensing device may be configured to measure a first physiologic parameter of the subject at the first location and the second sensing device may be configured to measure a second physiologic parameter different than the first physiologic parameter at the second location. The first sensing device and the second sensing device, in some embodiments, are configured to measure a same physiologic parameter at the first location and the second location. Analyzing the data may comprise utilizing first information obtained from the first sensing device and second information obtained from the second device to determine a difference in height between the first location and the second location. The difference in height may be utilized to determine a posture of the subject.

In some embodiments, the at least one stimulating device comprises a first stimulating device at a first location on the subject and a second stimulating device at a second location on the subject different than the first location. The signaling may comprise instructions to apply a first stimulus utilizing the first stimulating device at the first location and to apply a second stimulus different than the first stimulus utilizing the second stimulating device at the second location.

In some embodiments, the at least one stimulating device is integrated into at least one of a patch adhesively attached to the subject, a sock, an insole, a sandal, a shoe an orthotic, a glove, a wrap, a ring, a bracelet, an earbud and a face cover.

In some embodiments, the at least one stimulating device is integrated into a surface configured for contact with the subject. The surface configured for contact with the subject may comprise a bed.

In some embodiments, the at least one stimulating device is integrated into a device not contacting the subject. The device not contacting the subject may comprise at least one of a speaker, a display and a heating and cooling system.

In some embodiments, the at least one stimulating device comprises a disposable component configured to conform to an anatomy of the subject and comprising one or more electrodes configured to apply a stimulus to the subject, and a reusable component configured to interface with the disposable component, to receive the signaling, and to direct the one or more electrodes to apply the stimulus in response to the signaling.

In some embodiments, the at least one sensing device comprises an insulating region configured to interface with skin of a subject, a thermally conducting region configured to interface with the skin of the subject, a plurality of temperature sensors, the plurality of temperature sensors comprising at least a first temperature sensor in the insulating region and at least a second temperature sensor in the thermally conducting region, the plurality of temperature sensors configured to measure skin temperature in the insulating region and the thermally conducting region, and one or more environmental sensors configured to measure one or more thermal properties of surroundings of the sensing device. Analyzing the data may comprise deriving thermal gradients from readings from two or more of the plurality of temperature sensors arranged along a vector substantially normal to a surface of the skin of the subject. Analyzing the data may comprise estimating a core temperature of the subject based on readings from the plurality of temperature sensors. Estimating the core temperature may comprise deriving the core temperature from a blood temperature measured by the first temperature sensor in the insulating region. Estimating the core temperature may comprise deriving the core temperature from a sweat temperature measured by the first temperature sensor in the sensing region. The thermal properties of surroundings of the sensing device measured by the one or more environmental sensors may comprise at least one of humidity, air temperature, air velocity, air turbidity, ambient pressure and ambient light.

In some embodiments, an article of manufacture comprises a non-transitory processor-readable storage medium having stored therein executable program code which, when executed, causes a processing device to perform the above-described method.

In some embodiments, an apparatus comprises a processor and a memory coupled to the processor, the processor being configured to receive monitoring data from at least one sensing device coupled to a subject, to analyze the monitoring data to identify one or more physiologic parameters of the subject, to provide signaling to at least one stimulating device in response to the identified physiologic parameters, the signaling comprising instructions to apply a stimulus to the subject, to receive additional monitoring data from the sensing device, to analyze the additional monitoring data to identify one or more changes in the one or more physiologic parameters of the subject after application of the stimulus to the subject, and to provide additional signaling to the stimulating device, the additional signaling comprising instructions to modify the stimulus applied to the subject based on the identified changes in the one or more physiologic parameters.

In some embodiments, the apparatus comprises a host device wirelessly coupled to the sensing device and the stimulating device.

In some embodiments, the stimulus comprises an electrical stimulus. The electrical stimulus may comprise application of a pulse train. The pulse train may comprise two or more pulses having duration and charge delivery sufficient to stimulate tactile sensation while limiting pain fiber stimulation. The additional signaling may comprise instructions for modifying at least one of a duration of at least one pulse in the pulse train and a total charge of the at least one pulse in the pulse train. In some embodiments, the pulse train when applied to the subject mimics another stimulus, the other stimulus comprising at least one of vibration, pain, a wet sensation, heat or cold, taste, tension or stretch, sound, pressure and light. In some embodiments, the pulse train is applied to the subject to amplify another stimulus, the other stimulus comprising at least one of vibration, pain, a wet sensation, heat or cold, taste, tension or stretch, sound pressure and light.

In some embodiments, the stimulating device comprises a plurality of electrodes, and wherein the signaling comprises instructions to selectively activate the plurality of electrodes in different locations in a test pattern and to utilize one or more sensors in at least one of the sensing device and the stimulating device to measure a response of the subject to the stimulus at the different locations in the test pattern.

In some embodiments, analyzing the monitoring data comprises detecting an event based on measured levels of the one or more physiologic parameters, and wherein the stimulus comprises a therapeutic stimulus to remedy the event. The event may comprise a sleep apneic event, and the therapeutic stimulus may comprise application of stimulus to a plantar aspect of a foot of the subject. The event may comprise determining a sleep posture of the subject, and the therapeutic stimulus may comprise application of stimulus to alter the sleep posture of the subject.

In some embodiments, analyzing the monitoring data comprises detecting one or more measured values of physiologic parameters indicating that an event is likely to occur, and the stimulus comprises a therapeutic stimulus to reduce a likelihood that the event will occur.

In some embodiments, the sensing device and the stimulating device are physically distinct.

In some embodiments, a system comprises at least one sensing device coupled to a subject, at least one stimulating device coupled to the subject, and a host device comprising a memory and a processor coupled to the memory, the host device being wirelessly coupled to the at least one sensing device and the at least one stimulating device. The host device is configured to receive monitoring data from the at least one sensing device, to analyze the monitoring data to identify one or more physiologic parameters of the subject, to provide signaling to the at least one stimulating device in response to the identified physiologic parameters, the signaling comprising instructions to apply a stimulus to the subject, to receive additional monitoring data from the at least one sensing device, to analyze the additional monitoring data to identify one or more changes in the one or more physiologic parameters of the subject after application of the stimulus to the subject, and to provide additional signaling to the at least one stimulating device, the additional signaling comprising instructions to modify the stimulus applied to the subject based on the identified changes in the one or more physiologic parameters.

In some embodiments, the at least one sensing device comprises a first sensing device at a first location on the subject and a second sensing device at a second location on the subject different than the first location. The first sensing device may be configured to measure a first physiologic parameter of the subject at the first location and the second sensing device may be configured to measure a second physiologic parameter different than the first physiologic parameter at the second location. The first sensing device and the second sensing device may be configured to measure a same physiologic parameter at the first location and the second location. Analyzing the data may comprise utilizing first information obtained from the first sensing device and second information obtained from the second device to determine a difference in height between the first location and the second location. The difference in height may be utilized to determine a posture of the subject.

In some embodiments, the at least one stimulating device comprises a first stimulating device at a first location on the subject and a second stimulating device at a second location on the subject different than the first location. The signaling may comprise instructions to apply a first stimulus utilizing the first stimulating device at the first location and to apply a second stimulus different than the first stimulus utilizing the second stimulating device at the second location.

In some embodiments, the at least one stimulating device is integrated into at least one of a patch adhesively attached to the subject, a sock, an insole, a sandal, a shoe, an orthotic, a glove, a wrap, a ring, a bracelet, an earbud and a face cover.

In some embodiments, the at least one stimulating device is integrated into a surface configured for contact with the subject.

In some embodiments, the at least one sensing device is integrated into a device not contacting the subject.

In some embodiments, the at least one stimulating device comprises a disposable component configured to conform to an anatomy of the subject and comprising one or more electrodes configured to apply a stimulus to the subject, and a reusable component configured to interface with the disposable component, to receive the signaling, and to direct the one or more electrodes to apply the stimulus in response to the signaling.

In some embodiments, the at least one sensing device comprises an insulating region configured to interface with skin of a subject, a thermally conducting region configured to interface with the skin of the subject, a plurality of temperature sensors, the plurality of temperature sensors comprising at least a first temperature sensor in the insulating region and at least a second temperature sensor in the thermally conducting region, the plurality of temperature sensors configured to measure skin temperature in the insulating region and the thermally conducting region, and one or more environmental sensors configured to measure one or more thermal properties of surroundings of the sensing device.

BRIEF DESCRIPTION OF THE DRAWINGS

Several aspects of the disclosure can be better understood with reference to the following drawings. In the drawings, like reference numerals designate corresponding parts throughout the several views.

DETAILED DESCRIPTION

Figure 1:
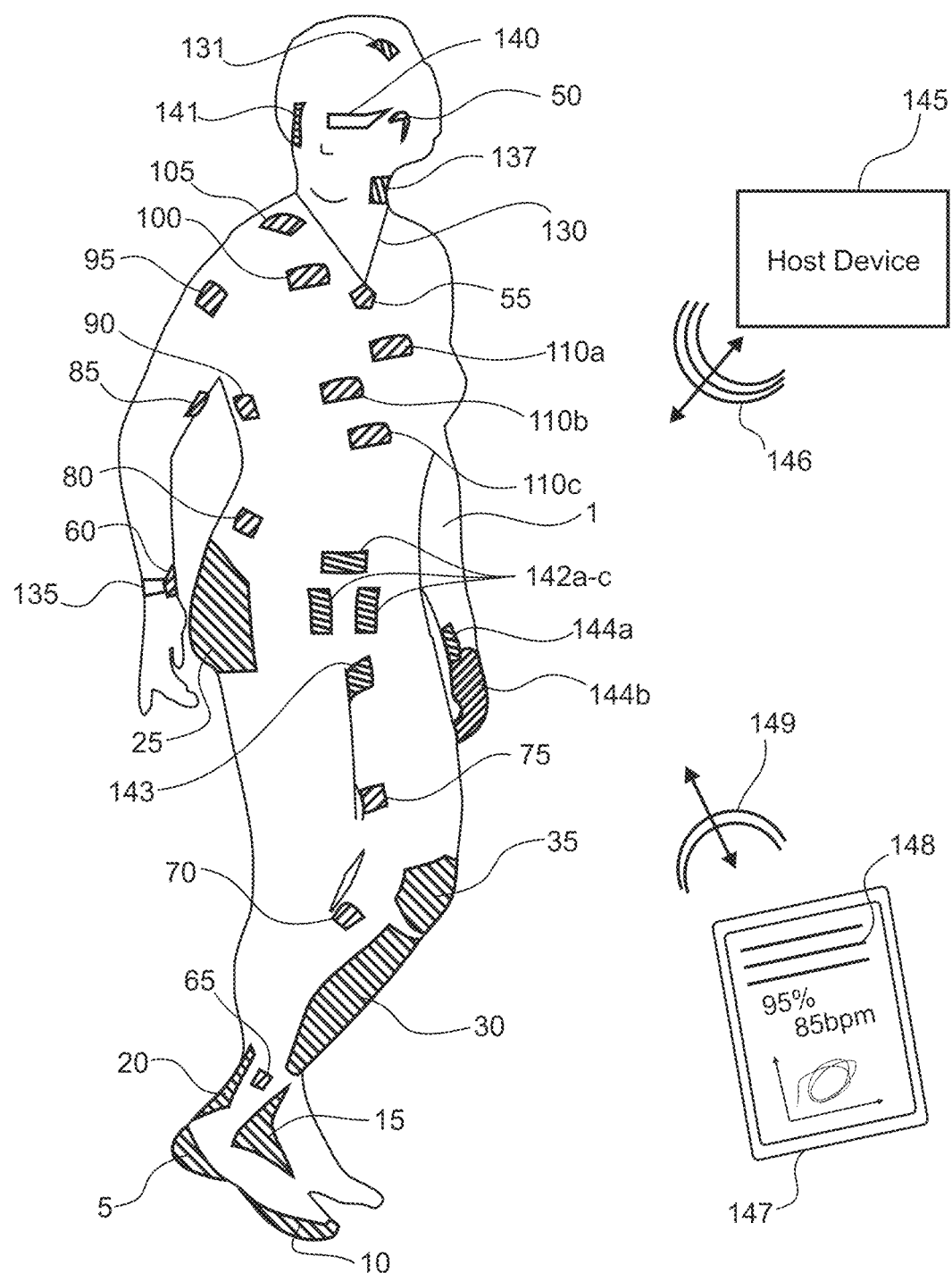
FIG. 1 illustrates aspects of a modular physiologic monitoring system, according to an embodiment of the invention.

Particular embodiments of the present disclosure are described herein below with reference to the accompanying drawings; however, the disclosed embodiments are merely examples of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures A modular physiologic monitoring system in accordance with the present disclosure for assessing one or more physiologic parameters of a subject (e.g., a human subject, a patient, an athlete, a trainer, an animal, such as equine, canine, porcine, bovine, etc.) with a body may include one or more patches, each patch adapted for attachment to the body of the subject (e.g., attachable to the skin thereof, reversibly attachable, adhesively attachable, with a disposable interface and a reusable module, etc.). In aspects, the physiologic monitoring system may include one or more modules, and each module may include a power source (e.g., a battery, a rechargeable battery, an energy harvesting transducer, microcircuit, and an energy reservoir, a thermal gradient harvesting transducer, a kinetic energy harvesting transducer, a radio frequency energy harvesting transducer, a fuel cell, a biofuel cell, etc.), signal conditioning circuitry, communication circuitry, one or more sensors, or the like, configured to generate one or more signals (e.g., physiologic and/or physical signals), stimulus, etc.

One or more of the patches may include one or more interconnects, configured and dimensioned so as to couple with one or more of the modules, said modules including a complimentary interconnect configured and dimensioned to couple with the corresponding patch. The patch may include a bioadhesive interface for attachment to the subject, the module retainable against the subject via interconnection with the patch.

In aspects, the patch may be configured so as to be single use (e.g., disposable). The patch may include a thin, breathable, stretchable laminate. In aspects, the laminate may include a substrate, a bioadhesive, one or more sensing or stimulating elements in accordance with the present disclosure, and one or more interconnects for coupling one or more of the sensing elements with a corresponding module.

In aspects, to retain a high degree of comfort and long term wear-ability of the patch on a subject, to limit interference with normal body function, to limit interference with joint movement, or the like, the patch may be sufficiently thin and frail, such that it may not substantially retain a predetermined shape while free standing. Such a definition is described in further detail below. The patch may be provided with a temporary stiffening film to retain the shape thereof prior to placement of the patch onto the body of a subject. Once adhered to the subject, the temporary stiffening film may be removed from the patch. While the patch is adhered to the subject, the shape and functionality of the patch may be substantially retained. Upon removal of the patch from the subject, the, now freestanding patch is sufficiently frail such that the patch can no longer substantially retain the predetermined shape (e.g., sufficiently frail such that the patch will not survive in a free standing state). In aspects, stretch applied to the patch while removing the patch from the subject may result in snap back once the patch is in a freestanding state that renders such a patch to crumple into a ball and no longer function.

In aspects, the patch may include a film (e.g., a substrate), with sufficiently high tear strength, such that, as the patch is peeled from the skin of a subject, the patch does not tear. In aspects, the ratio between the tear strength of the patch and the peel adhesion strength of the patch to skin (e.g., tear strength: peel adhesion strength), is greater than 8:1, greater than 4:1, greater than 2:1, or the like. Such a configuration may be advantageous so as to ensure the patch may be easily and reliably removed from the subject after use without tearing.

In aspects, the patch may include a bioadhesive with peel tack to mammalian skin of greater than 0.02 Newtons per millimeter (N/mm), greater than 0.1 N/mm, greater than 0.25 N/mm, greater than 0.50 N/mm, greater than 0.75 N/mm, greater than 2 N/mm, or the like. Such peel tack may be approximately determined using an American Society for Testing and Materials (ASTM) standard test, ASTM D3330: Standard test method for peel adhesion of pressure-sensitive tape.

In aspects, the patch may exhibit a tear strength of greater than 0.5 N/mm, greater than 1 N/mm, greater than 2 N/mm, greater than 8 N/mm, or the like. Such tear strength may be approximately determined using an ASTM standard test, ASTM D624: Standard test method for tear strength of conventional vulcanized rubber and thermoplastic elastomers.

In aspects, the patch may be provided with a characteristic thickness, of less than 50 micrometer (μm), less than 25 μm, less than 12 μm, less than 8 μm, less than 4 μm, or the like. Yet, in aspects, a balance between the thickness, stiffness, and tear strength may be obtained so as to maintain sufficiently high comfort levels for a subject, minimizing skin stresses during use (e.g., minimizing skin stretch related discomfort and extraneous signals as the body moves locally around the patch during use), minimizing impact on skin health, minimizing risk of nicking during use, and minimizing risk of maceration to the skin of a subject, while limiting risk of tearing of the patch during removal from a subject, etc.

In aspects, the properties of the patch may be further altered so as to balance the hydration levels of one or more hydrophilic or amphiphilic components of the patch while attached to a subject. Such adjustment may be advantageous to prevent over hydration or drying of an ionically conducting component of the patch, to manage heat transfer coefficients within one or more elements of the patch, to manage salt retention into a reservoir in accordance with the present disclosure, and/or migration during exercise, to prevent pooling of exudates, sweat, or the like into a fluid measuring sensor incorporated into the patch or associated module, etc. In aspects, the patch or a rate determining component thereof may be configured with a moisture vapor transmission rate of between 200 grams per meter squared per 24 hours ($g/m^2/24$ hrs) and 20,000 $g/m^2/24$ hrs, between 500 $g/m^2/24$ hrs and 12,000 $g/m^2/24$ hrs, between 2,000 $g/m^2/24$ hrs and 8,000 $g/m^2/24$ hrs, or the like.

Such a configuration may be advantageous for providing a comfortable wearable physiologic monitor for a subject, while reducing material waste and/or cost of goods, preventing contamination or disease spread through uncontrolled re-use, and the like.

In aspects, one or more patches and/or modules may be configured for electrically conducting interconnection, inductively coupled interconnection, capacitively coupled interconnection, with each other. In the case of an electrically conducting interconnect, each patch and module interconnect may include complimentary electrically conducting connectors, configured and dimensioned so as to mate together upon attachment. In the case of an inductively or capacitively coupled interconnect, the patch and module may include complimentary coils or electrodes configured and dimensioned so as to mate together upon attachment.

Each patch or patch-module pair may be configured as a sensing device to monitor one or more local physiologic and/or physical parameters of the attached subject (e.g., local to the site of attachment, etc.), local environment, combinations thereof, or the like, and to relay such information in the form of signals to a host device (e.g., via a wireless connection, via a body area network connection, or the like), one or more patches or modules on the subject, or the like. Each patch and/or patch-module pair may also or alternatively be configured as a stimulating device to apply a stimulus to the subject in response to signaling from the host device, the signaling being based on analysis of the physiologic and/or physical parameters of the subject measured by the sensing device(s).

In aspects, the host device may be configured to coordinate information exchange to/from each module and/or patch, and to generate one or more physiologic signals, physical signals, environmental signals, kinetic signals, diagnostic signals, alerts, reports, recommendation signals, commands, combinations thereof, or the like for the subject, a user, a network, an electronic health record (EHR), a database (e.g., as part of a data management center, an EHR, a social network, etc.), a processor, combinations thereof, or the like.

In aspects, a system in accordance with the present disclosure may include a plurality of substantially similar modules (e.g., generally interchangeable modules, but with unique identifiers), for coupling with a plurality of patches, each patch, optionally different from the other patches in the system (e.g., potentially including alternative sensors, sensor types, sensor configurations, electrodes, electrode configurations, etc.). Each patch may include an interconnect suitable for attachment to an associated module. Upon attachment of a module to a corresponding patch, the module may validate the type and operation of the patch to which it has been mated. In aspects, the module may then initiate monitoring operations on the subject via the attached patch, communicate with one or more patches on the subject, a hub, etc. The data collection from each module may be coordinated through one or more modules and/or with a host device in accordance with the present disclosure. The modules may report a time stamp along with the data in order to synchronize data collection across multiple patch-module pairs on the subject, between subjects, etc. Thus, if a module is to be replaced, a hot swappable replacement (e.g., replacement during a monitoring procedure) can be carried out easily by the subject, a caregiver, practitioner, etc. during the monitoring process. Such a configuration may be advantageous for performing redundant, continuous monitoring of a subject, and/or to obtain spatially relevant information from a plurality of locations on the subject during use.

In aspects, the modules and/or patches may include corresponding interconnects for coupling with each other during use. The interconnects may include one or more connectors, configured such that the modules and patches may only couple in a single unique orientation with respect to each other. In aspects, the modules may be color coded by function. A temporary stiffening element attached to a patch may include instructions, corresponding color coding, etc. so as to assist a user or subject with simplifying the process of monitoring.

In addition to physiologic monitoring, one or more patches and/or modules may be used to provide a stimulus to the subject, as will be described in further detail below.

A modular physiologic monitoring system, in some embodiments, includes one or more sensing devices, which may be placed or attached to one or more sites on the subject. Alternatively or additionally, one or more sensing devices may be placed "off" the subject, such as one or more sensors (e.g., cameras, acoustic sensors, etc.) that are not physically attached to the subject. The sensing devices are utilized to establish whether or not an event is occurring and to determine one or more characteristics of the event by monitoring and measuring physiologic parameters of the subject. The determination of whether an event has occurred or is occurring may be made by a device that is at least partially external and physically distinct from the one or more sensing devices, such as a host device in wired or wireless communication with the sensing devices as described below with respect to FIG. 1. The modular physiologic monitoring system includes one or more stimulating devices, which again may be any combination of devices that are attached to the subject or placed "off" the subject, to apply a stimulus to the subject to treat the event, to prevent the event from transition from a first form into a second form, to interrupt the event, to stimulate a type of input to the subject with an alternative form of energy (e.g., stimulating one or more of thermal input, vibration input, mechanical input, a compression or the like with an electrical input), etc.

The sensing devices of a modular physiologic monitoring system, such as patch-module pairs described below with respect to FIG. 1, may be used: to monitor one or more physiologic functions or parameters of a subject, to monitor one or more disease states of a subject; to monitor the state of one or more tissue sites (e.g., tissue health, pressure applied to the tissue, etc.) of a subject; to monitor one or more orientations of a region of a subject with respect to gravity, with respect to one or more other regions of the body of the subject (e.g., back posture, back orientation, neck orientation, spinal rotation, hip rotation, neck rotation, etc.); to monitor any of the above in combination with postural information (e.g., monitoring local muscle activity or spasm in combination with postural information), etc. The sensing devices of the modular physiologic monitoring system, or a host device configured to receive data or measurements from the sensing devices, may be utilized to monitor for one or more events (e.g., through analysis of signals measured by the sensing devices, from metrics derived from the signals, etc.). The stimulating devices of the modular physiologic monitoring system may be configured to deliver one or more stimuli (e.g., electrical, vibrational, acoustic, visual, etc.) to the subject. The stimulating devices may receive a signal from one or more of the sensing devices or a host device, and provide the stimulation in response to the received signal.

FIG. 1 shows aspects of a modular physiologic monitoring system in accordance with the present disclosure. FIG. 1 shows a subject 1 with a series of patches and/or patch-module pairs each in accordance with the present disclosure attached to the subject 1 at sites described below, a host device 145 in accordance with the present disclosure, a feedback/user device 147 in accordance with the present disclosure displaying some data 148 based upon signals obtained from the subject 1, and one or more feedback devices 135, 140, in accordance with the present disclosure configured to convey to the subject 1 one or more aspects of the signals or information gleaned therefrom. In some embodiments, the feedback devices 135, 140 may also or alternatively function as stimulating devices. The host device 145, the user device 147, the patches and/or patch-module pairs, and/or the feedback devices 135, 140 may be configured for wireless communication 146, 149 during a monitoring session.

In aspects, a patch-module pair may be adapted for placement almost anywhere on the body of a subject 1. As shown in FIG. 1, some sites may include attachment to the cranium or forehead 131, the temple, the ear or behind the ear 50, the neck, the front, side, or back of the neck 137, a shoulder 105, a chest region with minimal muscle mass 100, integrated into a piece of ornamental jewelry 55 (may be a host, a hub, a feedback device, etc.), arrangement on the torso 110a-c, arrangement on the abdomen 80 for monitoring movement or breathing, below the rib cage 90 for monitoring respiration (generally on the right side of the body to substantially reduce EKG influences on the measurements), on a muscle such as a bicep 85, on a wrist 135 or in combination with a wearable computing device 60 on the wrist (e.g., a smart watch, a fitness band, etc.), on a buttocks 25, on a thigh 75, on a calf muscle 70, on a knee 35 particularly for proprioception based studies and impact studies, on a shin 30 primarily for impact studies, on an ankle 65, over an Achilles tendon 20, on the front or top of the foot 15, on a heel 5, or around the bottom of a foot or toes 10. Other sites for placement of such devices are envisioned. Selection of the monitoring and/or stimulating sites is generally determined based upon the intended application of the patch-module pairs described herein.

Additional placement sites on the abdomen, perineal region 142a-c, genitals, urogenital triangle, anal triangle, sacral region, inner thigh 143, or the like may be advantageous in the assessment of autonomic neural function of a subject. Such placements regions may be advantageous for assessment of PNS activity, somatosensory function, assessment of SNS functionality, etc.

Placement sites on the wrist 144a, hand 144b or the like may advantageous for interacting with a subject, such as via performing a stress test, performing a thermal stress test, performing a tactile stress test, monitoring outflow, afferent traffic, efferent traffic, etc.

Placement sites on the nipples, areola, lips, labia, clitoris, penis, the anal sphincter, levator ani muscle, over the ischiocavernous muscle, deep transverse perineal muscle, labium minus, labium majus, one or more nerves near the surface thereof, posterior scrotal nerves, perineal membrane, perineal nerves, superficial transverse perineal nerves, dorsal nerves, inferior rectal nerves, etc. may be advantageous for assessment of autonomic neural ablation procedures, autonomic neural modulation procedures, assessment of the PNS of a subject, assessment of sexual dysfunction of a subject, etc.

Placement sites on the face 141, over ocular muscles, near the eye, over a facial muscle (e.g., a nasalis, temporalis, zygonaticus minor/major, orbicularis oculi, occipitofrontalis), near a nasal canal, over a facial bone (e.g., frontal process, zygomatic bone/surface, zygomaticofacial foreman, malar bone, nasal bone, frontal bone, maxilla, temporal bone, occipital bone, etc.), may be advantageous to assess ocular function, salivary function, sinus function, interaction with the lips, interaction with one or more nerves of the PNS (e.g., interacting with the vagus nerve within, on, and/or near the ear of the subject), etc.

In aspects, a system in accordance with the present disclosure may be configured to monitor one or more physiologic parameters of the subject 1 before, during, and/or after one or more of, a stress test, consumption of a medication, exercise, a rehabilitation session, a massage, driving, a movie, an amusement park ride, sleep, intercourse, a surgical, interventional, or non-invasive procedure, a neural remodeling procedure, a denervation procedure, a sympathectomy, a neural ablation, a peripheral nerve ablation, a radio-surgical procedure, an interventional procedure, a cardiac repair, administration of an analgesic, a combination thereof, or the like. In aspects, a system in accordance with the present disclosure may be configured to monitor one or more aspects of an autonomic neural response to a procedure, confirm completion of the procedure, select candidates for a procedure, follow up on a subject after having received procedure, assess the durability of a procedure, or the like (e.g., such as wherein the procedure is a renal denervation procedure, a carotid body denervation procedure, a hepatic artery denervation procedure, a LUTs treatment, a bladder denervation procedure, a urethral treatment, a prostate ablation, a prostate nerve denervation procedure, a cancer treatment, a pain block, a neural block, a bronchial denervation procedure, a carotid sinus neuromodulation procedure, implantation of a neuromodulation device, tuning of a neuromodulation device, etc.).

Additional details regarding modular physiologic monitoring systems, kits and methods are further described in PCT application serial no. PCT/US2014/041339, published as WO 2014/197822 and titled "Modular Physiologic Monitoring Systems, Kits, and Methods," and PCT application serial no. PCT/US2015/043123, published as WO 2016/019250 and titled "Modular Physiologic Monitoring Systems, Kits, and Methods, the disclosures of which are incorporated by reference herein in their entirety.

Various embodiments are described below with respect to utilizing a modular physiologic monitoring system, kits or methods for monitoring and management of sleep quality or one or other aspects of sleep of a subject and to monitoring and management of body temperature and systemic fatigue of a subject. It is to be appreciated, however, that embodiments are not limited to these specific use cases but are instead more broadly applicable to monitoring and management of one or more physiologic parameters of a subject.

In some embodiments, modular physiologic monitoring systems may be configured to treat sleep state disorders, such as sleep apnea. A modular physiologic monitoring system may utilize one or more sensing devices to detect an event or condition associated with sleep apnea and, in response to such detection, utilize one or more stimulating devices to apply therapy to the subject.

The sensing devices and the stimulating devices may be physically distinct, such as being physically attached to a subject at varying locations. For example, the sensing devices may be one or more of the patch-module pairs described above with respect to FIG. 1, such as the patch-module pair 137 adapted for placement on the chest, neck, or upper back of the subject 1 for assessing airway integrity and blockage, the patch-module pairs 110a-c adapted for placement on the torso for assessing an electrocardiogram (ECG) or respiratory electromyogram (EMG) of the subject 1, the patch-module pair 131 adapted for placement on the head or forehead for assessing electroencephalogram (EEG), electro-oculogram (EOG) or a sleep state of the subject 1, or various other patch-module pairs described above with respect to FIG. 1 which may be used to measure movement at one or more desired locations, patch-module pairs adapted for placement on a back, shoulders, lower back, etc. of the subject 1 for assessing muscle spasm or posture, two or more patch-module pairs on the subject 1 for assessing postural orientation, one or more patch-module pairs placed near the left or right sides of the torso at the base of the rib cage so as to monitor diaphragmatic breathing, etc. In addition, in some embodiments devices other than the patch-module pairs described above with respect to FIG. 1 may be used as sensing devices, such as devices for measuring a 12-lead ECG, one or more cameras for observing posture or postural orientation, one or more microphones or other acoustic sensors to detect changes in breathing, snoring, etc.

One or more of the patch-module pairs described above with respect to FIG. 1 may also or alternatively function as stimulating devices. For example, patch-module pairs 5, 10, 15 20 adapted for placement in various regions on and around the foot of the subject 1 may be used for applying a stimulus to the subject 1 in response to detecting a condition or event using one or more of the sensing devices. Similar to the sensing devices, the stimulating devices are not limited to being one of the patch-module pairs described above with respect to FIG. 1. In other embodiments, various other types of stimulating devices may be utilized as will be described in further detail below. For example, stimulating devices may take on various form factors in different embodiments. As described above with respect to FIG. 1, a stimulating device may be in the form of a patch-module pair, a wrist band or bracelet, ring, necklace, anklet, ocular feedback device, etc. A stimulating device may also or alternatively be provided in the form of a glove, sock, orthotic, etc. as will be described in further detail below.

As discussed above, embodiments are not limited to monitoring and management of the sleep state of a subject. In some embodiments, sensing devices may be used to detect impact or other conditions or events at a region of a subject which has no or little feeling, with the stimulating devices being utilized to apply a stimulus at another region of the subject which has comparatively greater feeling or sensation. As one example, one or more patch-module pairs 30 or 35 adapted for placement on the shin and knee of the subject 1 may be used as sensing devices to detect impact to the subject 1, with the patch-module pair 50 adapted for placement on or around the ear of the subject 1 being utilize to apply an auditory stimulus to the subject 1 on detecting impact to the knee or shin of the subject 1.

For managing sleep apnea, sleep state, exercise, physical assertion or other aspects of a subject, a number of therapeutic stimuli may be utilized by the stimulating devices in a modular physiologic monitoring system. Such stimuli may be positive (reinforcement) or negative (inhibitory). Electric discharge is one type of stimuli that may be utilized, whereby one or more of the stimulating devices in the modular physiologic monitoring system may deliver electrical energy to a body location in response to detecting an event such as an apneic episode or an obstructive apneic event using one or more of the sensing devices in the modular physiologic monitoring system. The sensing devices may measure any of a number of physiologic parameters of the subject, including but not limited to respiration depth or rate, respiration character, diaphragmatic movement or strength, EMG, extraocular muscles (EOM), acoustic or vibrational detection of obstruction, etc.

Once an event or condition is detected utilizing one or more of the sensing devices, the modular physiologic monitoring system can deliver a stimulus to a body part, such as the soles of the feet, the chest, the palms, the face/forehead, genitals, neck, ear, mastoid region, etc. using one or more of the stimulating devices. The stimulation may be electrical stimulation, such as a tactile sensation that avoids stimulating local pain fibers. The stimulation may have a short duration, such as 10-20 microseconds (µs) in some embodiments. The stimulation may also take the form of a pulse train having a variable or fixed repetition rate. The stimulating devices may utilize one or more monopolar, bipolar or multipolar electrodes to deliver the stimulus. In some embodiments, the stimulating devices are provided with a constant current supply, thus allowing the stimulating devices to have defined charge delivery, the capability of short duration pulses (e.g., 10-20 µs), and be configured to design the duration and charge delivery to stimulate tactile sensation while limiting or completely avoiding pain fiber stimulation. Pain fiber stimulation in some embodiments is limited or prevented through controlling the total charge of the electrical stimulation. The total charge, for example, may be limited to a maximum of 10-20 microcoulombs (µC). The electrical stimulation may also or alternatively be delivered as a multiple pulse train, a burst stimulation or other configuration. The low total charge to avoid pain fiber sensation is designed to be below the threshold for pain but enough to be sensed and reacted.

The sensing devices, as discussed above, may be configured to measure a wide variety of physiologic parameters of the subject including but not limited to ECG, EEG and/or EMG for measuring diaphragmatic parameters such as displacement, strength of contraction, EMG measurements, etc., hemoglobin (Hb) saturation, oxygen/carbon dioxide ($O_2/CO_2$) ratio from respiration, acoustic measurements (e.g., to sense airway obstruction, snoring, etc.), etc. The sensing devices may be in communication with an external sensing system or device, such as the host device 145 described above with respect to the FIG. 1 modular physiologic monitoring system. The host device 145 may also be in communication with one or more of the stimulating devices. Such a system may therefore provide closed loop sensing-stimulation, where the stimulus is based on algorithmic determination and/or classification of apnea events based on physiologic parameters measured by the sensing devices. In some embodiments, apnea events are detected based on respiration rate or period (e.g., time between breaths) and/or the depth of respiration and associated physiologic consequences based on data obtained using the sensing devices, followed by feedback or stimulus provided via the stimulating devices, where the feedback or stimulus is provided until data obtained using the sensing devices indicates that a satisfactory response has been achieved.

In some non-limiting examples, the sensing device(s) and the stimulating device(s) may be in direct communication with each other. In one non-limiting example, the stimulating device may provide a host wireless function while one or more sensing devices may include a peripheral wireless function, the stimulating device configured so as to manage communication with the plurality of sensing devices.

In some embodiments wherein the stimulating device includes one or more stimulating electrodes, the stimulation electrodes may be adapted for placement on the skin of a subject, such as skin at or near the foot (e.g., the sole or other dermatomes of the foot), at or near the auricle or posterior auricular nerves, at or near the internal auditory canal, etc. A stimulating device including one or more stimulating electrodes may be in the form of a patch and/or a patch-module pair or another device with an adhesive or other attachment for connection to the area or region of interest on the body. One or more stimulating electrodes may be monopolar, bipolar or multipolar.

The sensing and/or stimulating devices of a modular physiologic monitoring system may be configured for radio frequency (RF) or other wireless and/or wired connection with one another and/or a host device. Such RF or other connection may be used to transmit or receive feedback parameters or other signaling between the sensing and stimulating devices. The feedback, for example, may be provided based on measurements of physiologic parameters that are obtained using the sensing devices to determine when apneic or obstruction events are occurring. Various thresholds for stimulation that are applied by the stimulating devices may, in some embodiments, be determined based on such feedback. Thresholds may relate to the amplitude or frequency of electric or other stimulation. Thresholds may also be related to whether to initiate stimulation by the stimulating devices based on the feedback. For example, such thresholds may relate to physiologic consequences (e.g., such as low saturation).

Various stimulation algorithms may be activated based on the feedback. In some embodiments, the stimulating devices may act as a "respiratory pacemaker" with multiple modes, including sensing or on-demand stimulus or free running stimulus. In such embodiments, the respiration of the subject may be influenced by the stimulation provided by the stimulating device. Such capability may be advantageous to restart the breathing process of a subject, to pace the breathing of the subject, to awaken the subject, to avert an apneic event, or the like.

During and/or after stimulus is applied with the stimulating devices, the sensing devices may monitor the physiologic response of the subject. If stimulation is successful, stimulation may be discontinued. If apnea remains, stimulation may be continued and possibly altered (e.g., increasing a level or amplitude of an applied stimulus, etc.). The physiologic response may be monitored and the decision whether to continue or discontinue and/or whether to adjust stimulation may function on a breath by breath basis. The amplitude of stimulation may be adjusted if low stimulation levels are insufficient to achieve a desired response. As described above, it may be desired to provide electrical stimulation which stimulates tactile sensation while avoiding or limiting pain fiber sensation. Thus, in some embodiments, stimulus may start at a relatively low amplitude to limit pain fiber sensation and may be increased (either continuously or at discrete levels) until the electrical stimulus is sufficient to achieve the desired response. Thus, the electrical stimulus advantageously can provide tactile stimulation while limiting pain fiber sensation. In some embodiments, electrical stimulation may be in the form of electric shocks which are short, potent and repeat with increasing intensity until a desired response is achieved.

In some embodiments, a user of the modular physiologic monitoring system may set preferences for the stimulus type, level, and/or otherwise personalize the sensation during a setup period or at any point during use of the modular physiologic monitoring system. The user of the modular physiologic monitoring system may be the subject being monitored and stimulated by the sensing devices and stimulating devices, or a doctor, nurse, physical therapist, medical assistant, caregiver, etc. of the subject being monitored and stimulated. The user may also have the option to disconnect or shut down the modular physiologic monitoring system at any time, such as via operation of a switch, pressure sensation, voice operated instruction, etc.

Although described above with respect to measuring and managing sleep apnea, modular physiologic monitoring systems described herein may also be used more generally in measuring and managing sleep quality including non-apneic low quality sleep. The assessment of low sleep quality may be based on assessment of a number of physiologic parameters, such as EEG, EKG, EMG, respiratory rate or depth, etc. Low sleep quality events may be detected based on data obtained using the sensing devices and feedback or stimulus may be provided to the subject in response to detection of low sleep quality events utilizing the stimulating devices.

In one non-limiting embodiment, a system for treating bruxism may be formed, the system including one or more sensing devices placed onto the forehead, neck, jaw, or mastoid region of a subject, the sensing devices configured so as to monitor an electromyographic signal from the subject during use, the EMG signal pertaining to the grinding of teeth, clenching of the jaw of the subject, etc. The system may include one or more stimulating devices, the stimulating devices configured to stimulate the subject to avert a bruxism event, to alter a clenching or grinding event, or the like. In such a way, the feedback provided by the stimulation may affect the behavior of the subject, retrain the subject to avoid the unwanted behavior, etc.

In some embodiments, algorithms for determining whether a sleep apnea event or other type of event has occurred may be based on a number of inputs. The various inputs may be measured directly utilizing one or more of the sensing devices, or may be derived based at least in part using measurements from one of or a combination of sensing devices. Inputs used in some embodiments include respiratory rate, respiratory depth, diaphragm movement and excursion, apnea duration, $O_2$ saturation, grinding event, sleep state, dream state, snoring or obstruction, heart rate (HR) and/or HR variability, EEG (e.g., alpha, beta, delta, etc.), EOG, EOM, etc.

Based on detected events, a modular physiologic monitoring system may provide a number of outputs to one or more of the stimulating devices and/or one or more of the sensing devices. Outputs may include, by way of example, feedback or stimulus as described above, which may be positive and/or negative. Biofeedback output may be provided for better sleep, and various diagnostics may be used for determining sleep quality and possible remedial measures to improve sleep quality. Such diagnostics include EKG, EEG (e.g., such as synchronizing stimuli), EOM, sweating, motion or body positioning, EMG (e.g., to measure or quantify a relaxed state of a subject, activation of target muscle groups, eye movement, rapid eye movement, diaphragmatic activation, muscle tone, tongue movement, muscle twitching, etc.), dreaming, sympathetic-parasympathetic state and/or responses, core and vitals measurements, core temperature, sudomotor activity, etc.

Stimulus or feedback which may be provided via one or more stimulating devices in a modular physiologic monitoring system may be in various forms, including physical stimulus (e.g., electrical, thermal, vibrational, pressure, stroking, a combination thereof, or the like), optical stimulus, acoustic stimulus, etc.

Physical stimulus may be provided in the form of negative feedback, such as in a brief electric shock or impulse as described above. Data or knowledge from waveforms applied in conducted electrical weapons (CEWs), such as in electroshock devices, may be utilized to avoid painful stimulus. Physical stimulus may also be provided in the form of positive feedback, such as in evoking pleasurable sensations by combining non-painful electrical stimulus with pleasant sounds, lighting, smells, etc. Physical stimulus is not limited solely to electrical shock or impulses. In other embodiments, physical stimulus may be provided by adjusting temperature or other stimuli, such as in providing a burst of cool or warm air, a burst of mist, vibration, tension, stretch, pressure, etc.

Feedback provided via physical stimulus as well as other stimulus described herein may be synchronized with, initiated by or otherwise coordinated or controlled in conjunction with an apnea monitor. The apnea monitor, which may be in the form of a host device and/or one or more sensing devices, can be connected to the stimulating devices physically (e.g., via one or more wires or other connectors), wirelessly (e.g., via radio or other wireless communication), etc. Physical stimulus may be applied to various regions of a subject, including but not limited to the wrist, soles of the feet, palms of the hands, nipples, forehead, ear, mastoid region, the skin of the subject, etc.

Optical stimulus may be provided via one or more stimulating devices as various psychoacoustics. The optical stimulus may be positive or negative (e.g., by providing pleasant or unpleasant lighting or other visuals). Acoustic stimulus similarly may be provided via one or more stimulating devices, as positive or negative feedback (e.g., by providing pleasant or unpleasant sounds). Acoustic stimulus may take the form of spoken words, music, etc. Acoustic stimulus, in some embodiments may be provided via smart speakers or other electronic devices such as Alexa® by Amazon®, Google Home®, etc.

As described above, the modular physiologic monitoring system may operate in a therapeutic mode, in that stimulation is provided when respiration fails. The modular physiologic monitoring system, however, may also operate as or provide a respiratory pacemaker in other embodiments. In such embodiments, the modular physiologic monitoring system has the potential to reduce the frequency of apneic events and possibly avoid apneic events altogether. A cardiac pacemaker watches for a cardiac action potential, and if such cardiac action potential does not happen within an allotted time frame, the cardiac pacemaker initiates the pacing automatically. A modular physiologic monitoring system may provide a respiratory pacemaker to keep a subject breathing, even in the case that the subject stops breathing during a monitoring session in a similar manner by monitoring breathing and initiating stimulus if breathing is not regular or otherwise as desired.

In a therapeutic mode, the modular physiologic monitoring system may apply stimulus in response to detecting events, where the events are based on certain thresholds meeting the definitions for events. Examples of events include apneic events and hypopnea events. An apneic event may be defined as one in which air flow cessation is 10 seconds or longer. A hypopnea event may be defined as one in which there is reduced air flow for 10 seconds or longer. It is to be appreciated, however, that these event definitions may be altered as desired, and that numerous other event types may be defined as described herein. To determine whether these events have occurred, the modular physiologic monitoring system may measure a number of physiologic parameters of the subject using one or more sensing devices. Physiologic parameters may contribute to detection of an event based on thresholds, which may be pre-defined or programmable. Thresholds may relate to various physiologic parameters, including but not limited to: hemoglobin oxygen saturation (% HbSAT); end tidal $CO_2$ value; a respirator quotient value; snoring, thoracoabdominal paradoxic breathing or increased respiratory effort; EEG evidence of disturbance (e.g., Alpha intrusion, epileptiform activity, etc.); blood pressure criteria; parasomnias (e.g., sleep talking, sleep walking, bruxism, etc.); flattening of inspiratory nasal flow; apnea-hypopnea index; exceeding preset hypoxemic burden (e.g., cumulative percentage of time under 90% saturation); rapid eye movement (REM) sleep latency values; lack of physical activity; onset ventricular or atrial ectopy (e.g., bradycardia, tachycardia, arrhythmia such as atrial fibrillation, etc.); and time delay from the last breath, measured by a clock or other means. It is to be appreciated that embodiments may utilize any one of or combination of these and other thresholds described herein.

In a prophylactic mode, the modular physiologic monitoring system may apply stimulus continuously or at defined intervals, rather than (or in addition to) in response to detecting particular events. Regular stimulation may be provided via one or more stimulating devices so as to establish a regular breathing cycle. Prophylactic respiratory stimulation provides advantages for neural entrainment/neuroplasticity in keeping breathing constant and continuous. The stimulation may be provided regularly or at intervals, or with cyclic variation for physiologic matching (e.g., to match physiologic parameters or activity measured by sensing devices in a modular physiologic monitoring system). The stimulation, in some embodiments, may thus be continuous or near-continuous. Prophylactic respiratory stimulation de-emphasizes pathologic components of obstructive sleep apnea (OSA) and other diseases of respiration/drive.

Modular physiologic monitoring systems may also provide intermittent stimulation so as to avert or break an apneic event, or pace respiration of a subject in a less continuous method. In such applications, the stimulation may be provided on an as needed basis. Alternatively, the stimulation may be applied in a non-periodic way, so as to break a respiratory cycle, reset a breathing cycle, or the like. The timing of such intermittent stimulation may be influenced by one or more signals obtained by a sensing device in accordance with the present disclosure.

In some embodiments, modular physiologic monitoring systems may be utilized to provide preventative stimulus, such as providing stimulus in a pulse train with the goal of entrainment or programming neuroplasticity (e.g., central, peripheral) for normalizing or improving breathing in any sleep stage. While awake or under hypnosis, a specific stimulus may be associated with the need to take an unobstructed breath. Using the stimulating devices in the modular physiologic monitoring system, such stimulus may be applied. The stimulus may be applied during consciousness and/or during sleep. For example, stimulus may be applied while a subject is conscious for learning and teaching, with learning spillover from conscious learned behavior to the sleep state of the subject. The desired action (e.g., taking an unobstructed breath) becomes a learned reflex for application to the subject via the stimulating devices while the subject is asleep. Hypnosis, meditation or other teaching techniques may be used to facilitate the spillover from conscious learned behavior to the sleep state of the subject. In some embodiments, a goal is to teach the subject to take unobstructed breaths in response to the associated stimulus.

In some embodiments, stimulus may be provided using voice recordings. For example, the modular physiologic monitoring system may provide the stimulus via an audible command to the subject to perform an action while they are sleeping (e.g., taking an unobstructed breath, moving into a different position, etc.). In order to make the subject more open to suggestion, the modular physiologic monitoring system may allow the subject to individualize the commands to suit their preference, such as in allowing the subject to make an audio recording of his/her own voice or of a trusted voice (e.g., a spouse, parent, etc.). As one example, the subject may be prompted to record "BREATH <subject's name>", giving familiarity to the subject for the auditory stimulus. The auditory stimulus may be provided via an earpiece, a smart speaker, home audio system, alarm clock, smart phone, etc. The audible stimulus may also be utilized to facilitate or provide hypnosis.

In some embodiments, a modular physiologic monitoring system may be configured to provide multi-modal stimuli to a subject. Multi-modal approaches use one or more forms of stimulation (e.g., thermal and electrical, mechanical and electrical, etc.) in order to mimic another stimulus to trick local nerves into responding in the same manner to the mimicked stimulus. In addition, in some embodiments multi-modal stimulus or input may be used to enhance a particular stimulus. For example, the effect of a thermal stimulus may be enhanced by adding a mimicked electrical stimulus.

Modular physiologic monitoring systems may use pulses across space and time (e.g., frequency, pulse trains, relative amplitudes, etc.) to mimic vibration, comfort or discomfort, mild or greater pain, wet sensation, heat/cold, training neuroplasticity, taste (e.g., using a stimulating device placed in the mouth or on the tongue of a subject to mimic sour, sweet, salt, bitter or umami flavor), tension or stretching, sound or acoustics, sharp or dull pressure, light polarization (e.g., linear versus polar, the "Haidinger Brush"), light color or brightness, etc.

Stimulus amplification may also be provided by modular physiologic monitoring systems using multi-modal input. Stimulus amplification represents a hybrid approach, wherein a first type of stimulus may be applied and a second, different type of stimulus provided to enhance the effect of the first type of stimulus. As an example, a first stimulus may be provided via a heating element, where the heating element is augmented by nearby electrodes or other stimulating devices that amplify and augment the heating stimulus using electrical mimicry in a pacing pattern. Electrical stimulus may also be used as a supplement or to mimic various other types of stimulus, including but not limited to vibration, heat, cold, etc. Different, possibly unique, stimulation patterns may be applied to the subject, with the central nervous system (CNS) and peripheral nervous system (PNS) interpreting such different or unique stimulation patterns as different stimulus modalities.

Another example of stimulus augmentation is sensing a "real" stimulus, measuring the stimulus, and constructing a proportional response by mimicry such as using electric pulsation. The real stimulus, such as sensing heat or cold from a Peltier device, may be measured by electrical-thermal conversion. This real stimulus may then be amplified using virtual mimicry, which may provide energy savings and the possibility of modifying virtual stimulus to modify the perception of the real stimulus.

In some embodiments, the stimulating devices in a modular physiologic monitoring system include an electrode array that attaches (e.g., via an adhesive or which is otherwise held in place) to a preferred body part, such as the sole of a foot, the head or forehead, an inner wrist, etc. One or more of the stimulating devices may include a multiplicity of both sensing and stimulation electrodes, including different types of sensing and/or stimulation electrodes. The sensing electrodes on the stimulation devices, in some embodiments, may be distinct from the sensing devices in the modular physiologic monitoring system in that the sensing devices in the modular physiologic monitoring system may be used to measure physiologic parameters of the subject while the sensing electrodes on the stimulation devices in the modular physiologic monitoring system may be utilized to monitor the application of a stimulus to the subject.

A test stimulus may be initiated in a pattern in the electrode array, starting from application via one or a few of the stimulation electrodes and increasing in number over time to cover an entire or larger portion of the electrode array. The test stimulus may be used to determine the subject's response to the applied stimulation. Sensing electrodes on the stimulation devices may be used to monitor the application of the stimulus. The electrode array may also be used to record from desired output (e.g., initiate a breath). As such, one or more of the electrodes in the array may be configured so as to measure the local evoked response associated with the stimulus itself. Such an approach may be advantageous to confirm capture of the target nerves during use. By monitoring the neural response to the stimulus, the stimulus parameters including amplitude, duration, pulse number, etc. may be adjusted while ensuring that the target nerves are enlisted by the stimulus in use.

The test stimulus may migrate or be applied in a pattern to different electrodes at different locations in the electrode array. The response to the stimulus may be recorded or otherwise measured, using the sensing devices in the modular physiologic monitoring system and/or one or more of the sensing electrodes of the stimulating devices in the modular physiologic monitoring system. The response to the test stimulus may be recorded or analyzed to determine an optimal sensing or application site for the stimulus to achieve a desired effect or response in the subject. Thus, the test stimulus may be utilized to find optimal sensing (e.g., dermatome driver) location. This allows for powerful localization for optimal pacing or other application of stimulus, which may individualized for different subjects.

An electrode array provided by the stimulating devices in the modular physiologic monitoring system may include an electrode patch that is driven by another, possibly larger, device that is apposed to the patch. For example, for foot stimulation, the device may be an orthotic. The patch may be attached to the skin of the subject, possibly to the sole of a foot of the subject via a biologic adhesive. An orthotic may be attached to the patch via adhesive, magnetic, mechanical snap, a combination thereof, or other attachment means. The orthotic permits movement of the device as the physiologic source disappears. As sensing patterns are completed, areas which are optimal for stimulating breathing or another desired result (e.g., optimizing blood pressure (BP) parameters, etc.) may be identified and recorded. Such optimal areas can be used as the principal sites for subsequent stimulation. Over time, the optimal sites may change. Test stimulus may be periodically re-applied to adjust the optimal sites as desired. With a multiple electrode array, adjustments may be made for optimal sensing and stimulation via algorithmic changes in software, using the same hardware as the electrode array can permit a wide distribution of electrodes over a region of the subject. The orthotic may contain a power source, one or more processors, signal processing circuitry, one or more analog to digital converters, communications circuitry, etc.

A modular physiologic monitoring system which utilizes an electrode array in stimulating devices has a wide variety of potential applications. One such application, in treating OSA, is described above. Other non-limiting examples of potential applications are discussed below.

For epilepsy, the modular physiologic monitoring system may include one or more sensing devices configured to monitor brain activity. For example, if a sensing EEG records suspicious activity, the stimulating devices in the modular physiologic monitoring system can initiate therapeutic stimulus. Detected incidents may be used as sources for intervention, such as an algorithm for sensing, locating, processing, amplifying and acting to close the loop. Alternatively or additionally, a baseline stimulation level may be applied to keep desired patterns of breathing dominant. For epilepsy, the stimulus may sync with EEG, EOM/EMG of EOM musculature, HR, HRV, or the like. EMG may be used alone or as one of several inputs. The baseline stimulation may be used as a preventative measure to maintain desired BP characteristics, stable HR rhythms, to avoid or reduce seizures, etc. A normal or desired pattern may be maintained via entrainment and abnormal activity may be suppressed. The gain is as described above with respect to OSA, where a small geographic stimulus may be amplified by stimulus from surrounding electrodes, including multi-modal stimulus. The stimulus may be driven by sensing an initial physiologic response to the small geographic stimulus. The modular physiologic monitoring system may also be used to find optimal stimulus sites, such as those of acupuncture, reflexology or other dermal stimulation that moderates and/or modulates hypertension (HTN), HR or other autonomic functions. Several stimulation sites may also be used in parallel with one another via timed or synchronized stimulation, such as via stimulation sites on the head/forehead of the subject, soles of the feet of the subject, wrist of the subject, etc.

A number of combinations of sensing devices and stimulating devices which may be used in some embodiments will now be described. It is to be appreciated, however, that these combinations are provided by way of example only, and that embodiments are not limited to the specific combinations of sensing and/or stimulating devices described below.

In a first example, a sensing device is placed on the torso of the subject near enough to the esophagus so as to monitor both an ECG and to listen to internal lung/esophagus audible noises. The sensing device may also be configured to monitor skin temperature as well as to predict core temperature, to monitor movement and to monitor external audible sounds (e.g., such as sounds related to speech, snoring, etc.).

In a second example, a first sensing device is placed on the lower back of the subject near to one or more muscle groups so as to measure one or more EMG signals from local muscles. The first sensing device may also be configured to monitor one or more orientation parameters (e.g., to measure an orientation of the first sensing device with respect to gravity, with respect to a second sensing device or one or more other devices placed on or near the subject, etc.). The second sensing device is placed on the neck, torso, face, etc. of the subject, configured to measure a range of physiological signals as well as the one or more orientation parameters (e.g., to measure an orientation of the second sensing device with respect to gravity, with respect to the first sensing device or one or more other devices placed on or near the subject, etc.). One or more algorithms are used to collect orientation parameters from the first sensing device and the second sensing device to determine the orientation between the first sensing device and the second sensing device.

In a third example, a sensing device is placed on the neck of a subject, where the sensing device includes at least one set of electrodes coupled to the neck of the subject as well as a down-facing microphone and/or other acoustic sensor. The sensing device may include an additional outfacing microphone. The set of electrodes are configured to measure at least one EMG signal from the neck of the subject (e.g., muscles associated with tongue movement, with throat muscle activity, etc.). The set of electrodes may also include one or more electrodes that are oriented so as to measure an ECG of the subject (e.g., so as to pick-up cardiographic information possibly using the same electrodes that measure the EMG signal). The down-facing microphone or other acoustic sensor is configured to monitor for occlusion of the esophagus of the subject, and to listen for airway sounds of the subject. Optionally, the outfacing microphone may be configured to monitor audible snoring, choking, and other sounds associated with the airway of the subject. Collectively, the set of electrodes and the down-facing microphone or other acoustic sensor are used to determine if the subject is experiencing an airway obstruction, has stopped breathing, etc.

In a fourth example, a sensing device is placed on a location of the subject (e.g., on the skin of the subject). The sensing device includes one or more stretch and/or interfacial pressure sensors, such that the sensing device is configured to measure one or more of pressure application and tissue stretch locally at the site of application of the sensing device. A stimulating device is optionally placed onto another site on the subject, or at a site on the body of a caregiver, with the stimulating device being configured to apply a stimulus to the subject based upon one or more signals measured by the sensing device. The stimulating device may also or alternatively be configured to provide one or more alerts to the subject and/or caregiver based on the signals measured by the sensing device.

In a fifth example, a stimulating device is placed on a target site on a subject (e.g., sole of the foot, genitals, peroneal tissue, ear, outer ear, mastoid region, palm of hand, temple, forehead, jaw, neck, etc.). The stimulating device is configured to provide one or more stimuli (e.g., electrical stimulus, thermal stimulus, vibrational stimulus, stretch action, pinch action, combinations thereof, etc.) to the subject. The stimulating device may take on a number of form factors, such as a patch-module or patch/hub pair, an adhesively applied device, a sock, an insole, a sandal or shoe, etc., a glove, a wrap (e.g., on a foot, hand, wrist, ankle, genital, etc.), a ring, an earbud or earphone which optionally access the mastoid region as a site for stimulus input, a face cover for audio and/or visual stimulus input, a non-contacting stimulating device such as an audio and/or visual system, a system integrated into a bed, chair, exercise equipment, etc. Possible implementations of these and other form factors are described below.

A stimulating device applied to the subject via an adhesive (e.g., an adhesively applied stimulating device), may be in the form of a disposable or reusable unit, such as a patch and or patch-module or patch/hub pair as described above with respect to FIG. 1. An adhesively applied stimulating device, in some embodiments, includes a disposable interface configured so as to be thin, stretchable, able to conform to the skin of the subject, and sufficiently soft for comfortable wear. The disposable interface may be built from very thin, stretchable and/or breathable materials, such that the subject generally does not feel the device on his or her body.

The adhesively applied stimulating device also includes a means for interfacing with the subject through an adhesive interface and/or a window in the adhesive interface. Such means may include a plurality of electrodes that are coupled with a reusable component of the adhesively applied stimulating device and that are coupled to the body of the subject through the adhesive interface. The means may also or alternatively include: a vibrating actuator to provide vibration normal to and/or transverse to the surface of the skin on which the adhesively applied stimulating device is attached to the subject; a thermal device such as a Peltier device, a heating element, a cooling element, an RF heating circuit, an ultrasound source, etc.; a means for stroking the skin such as a shape memory actuator, an electroactive polymer actuator, etc.; a means for applying pressure to the skin such as a pneumatic actuator, a hydraulic actuator, etc.

Actuation means of the adhesively applied stimulating device may be applied over a small region of the applied area of the subject, such that the adhesive interface provides the biasing force necessary to counter the actuation of the actuation means against the skin of the subject.

Adhesively applied stimulating devices may be provided as two components—a disposable body interface and a reusable component. The disposable body interface may be applied so as to conform to the desired anatomy of the subject, and wrap around the body such that the reusable component may interface with the disposable component in a region that is open and free from a natural interface between the subject and another surface. As an example, the disposable body interface may include a thin, breathable and disposable element including a plurality of electrodes that is applied over the base of a foot of a subject such that the plurality of electrodes are biased against the medial plantar, lateral plantar, saphenous, tibial, and/or sural dermatomes of the foot, with one or more regions of the disposable body interface extending around from the plantar to the dorsal surface of the foot or to the ankle. Over the region of the patch on the dorsal surface or ankle region, the reusable component such as a module or hub may be applied such that the electrode interface, power, etc. may be provided by a sealed, reusable device through the disposable interface. By locating the device attachment region on the dorsal region of the foot or near the ankle, a more repeatable attachment location may be achieved.

An adhesively applied stimulating device may also be a single component, rather than a two component or other multi-component arrangement. Such a device implemented as a single component may include an adhesive interface to the subject including two or more electrodes that is applied to the subject. Adhesively applied stimulating devices embodied as a single component provide potential advantages such as easier application to the body of the subject, but may come at a disadvantage with regards to one or more of breathability, conformity, access to challenging interfaces, etc. relative to two component or multi-component arrangements.

Figure 2:
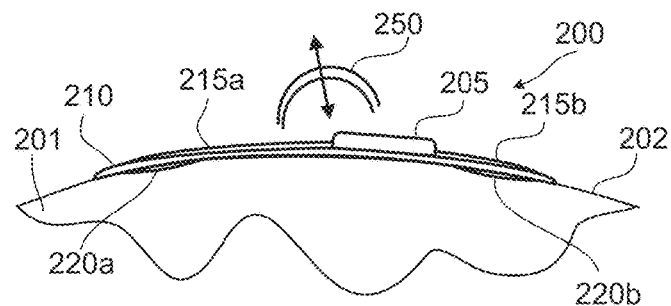
FIG. 2 illustrates an adhesively-applied stimulating device comprising a patch-module pair, according to an embodiment of the invention.

FIG. 2 illustrates an example of an adhesively applied stimulating device embodied as a patch-module pair 200. As shown, the patch-module pair 200, including module 205 coupled to patch 210, is applied to a skin surface 202 of a subject 201. It is to be appreciated that the patch-module pair 200 may function as a sensing device in addition to or instead of a stimulating device depending on the functionality of the electrodes 215a, 215b, 220a, 220b included in the patch 210. Electrodes 215a, 215b are outwardly facing (e.g., away from the skin surface 202 of the subject 201). Electrodes 220a, 220b interface with the skin surface 202 of the subject 201. One or more of the electrodes 215a, 215b, 220a, 220b may be used as sensors to sense physiologic parameters associated with the subject 201 and/or the ambient environment around the subject 201. One or more of the electrodes may also or alternatively be configured to apply stimuli to the subject 201.

The patch-module pair 200 is in wireless communication 250 with one or more other devices in a modular physiologic monitoring system, such as one or more other stimulating devices, one or more sensing devices and/or a host device. Advantageously, patch 210 may be stretchy so as to maintain monitoring and/or application of stimuli to the subject 201 in light of movements, changes in shape or stretching along the skin surface 202 of the subject 201. The patch-module pair 200 is an example of a multi-component adhesively applied device, in that the patch-module pair 200 includes a low cost disposable patch 210 and a miniature reusable module 205. Such a configuration may be advantageous to provide a soft and comfortable sensing and/or stimulating device for a modular physiologic monitoring system.

Figure 3:
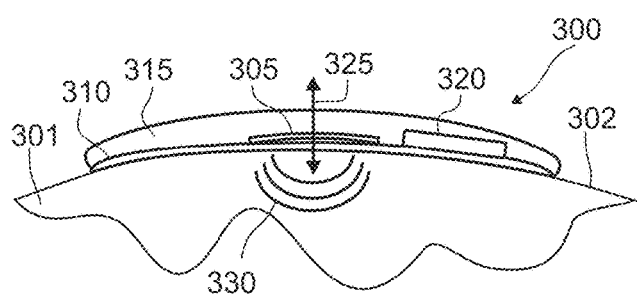
FIG. 3 illustrates a patch-module pair with vibratory stimulus means, according to an embodiment of the invention.
Figure 4:
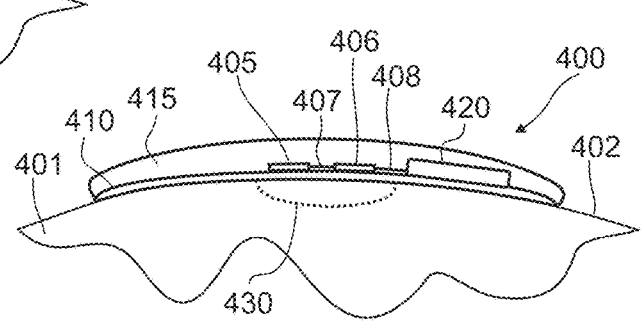
FIG. 4 illustrates a patch-module pair with thermal stimulus means, according to an embodiment of the invention.
Figure 5:
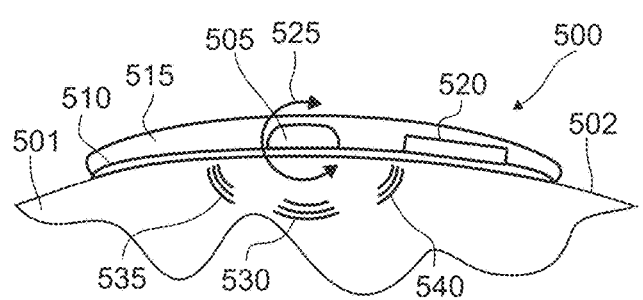
FIG. 5 illustrates a patch-module pair with tactile stimulus means, according to an embodiment of the invention.

As discussed above, various types of input or stimulus may be applied to a subject with a stimulating device. In some embodiments, the stimulus is in the form of electrical shock. For example, the skin-interfacing electrodes 220a, 220b of patch 210 may be configured to apply electrical energy to the subject 201. FIGS. 3-5 show examples of adhesively applied stimulating devices which utilize other means for applying other types of stimulus.

FIG. 3 illustrates a patch-module pair 300 configured to apply vibrational energy or stimulus 325 to the skin surface 302 of subject 301. The patch-module pair 300 includes an adhesive layer 310 (e.g., potentially forming part of a patch) and a module 315. The adhesive layer 310 secures the patch-module pair 300 to the skin surface 302 of the subject 301. The module 315 includes a transducer 305 configured to generate vibrational energy 325 for transfer 330 into the subject 301. The transducer 305 may be controlled and/or powered by an electronics unit 320 included in the module 315. In the non-limiting example shown, the transducer 305 may be piezoelectric material (e.g., a polymer, ceramic, etc.).

FIG. 4 illustrates a patch-module pair 400 for applying thermal energy or stimulus 430 to a subject 401. The patch-module pair 400 includes an adhesive layer 410 (e.g., potentially forming part of a patch) and a module 415. The adhesive layer 410 secures the patch-module pair 400 to the skin surface 402 of the subject 401. The module 415 includes one or more heater bands 405 or RF heating circuits, and thermocouples 406 coupled to an electronics unit 420 including a power source, a microcircuit, etc. via one or more electronic interconnects 408.

FIG. 5 illustrates a patch-module pair 500 for applying a tactile input or stimulus 525 to a subject 501. The patch-module pair 500 includes an adhesive layer 510 (e.g., potentially forming part of a patch) and a module 515. The adhesive layer 510 secures the patch-module pair 500 to the skin surface 502 of the subject 501. The module 515 includes a transducer 505 configured to generate torsional energy 525 for transfer 530, 535, 540 into the subject 501. The transducer 505 may be controlled and/or powered by an electronics unit 520 included in the module 515. In the non-limiting example shown, the transducer 505 may be an electric motor with an eccentricity on the output shaft thereof. The transfer 530, 535, 540 of energy into the skin surface 502 of the subject 501 may induce a range of sensations (e.g., poking, rubbing, etc.) dependent upon the amplitude, frequency, duration, duty cycle, etc. of the transducer 505 as well as the physical configuration of the patch-module pair 500 and the choice of adhesive layer 510, if such a layer is used in the embodiment in question.

It is to be appreciated that the means described with respect to FIGS. 2-5 for applying stimulus to a subject are not limited to use solely in stimulating devices which utilize an adhesively applied form factor. Similar means may be utilized in other form factors described below.

For the sock form factor, the stimulating device or a disposable component thereof may be integrated into a sock. The sock may include one or more electrodes (e.g., dry electrodes, wet electrodes, electrodes with adhesives and/or slick gel-like interfaces, etc.) and one or more leads connecting the electrodes with a coupling region located elsewhere on the sock. A reusable component of the stimulating device, such as a module or hub, may interface with the coupling region to provide electrical or other stimuli to the subject through the one or more electrodes.

In some embodiments, stimulus is focused for application to the foot of a subject. Sock-based approaches for stimulating devices for example, can be used to provide an interface with the bottom of the foot to provide stimuli to the subject. Specifically, a sock-based stimulating device may apply stimuli to the plantar region on the foot of a subject.

A sock-based stimulating device may include fabric that is formed into a generally tube-like structure so as to conform to feature(s) of a foot when pulled thereon. The sock may include a plurality of electrodes, facing towards an interior thereof. One or more of these electrodes may include an ionically conducting gel medium for providing electrical communication with the tissues of a subject when biased towards the tissues thereof. The sock may include a plurality of electrical interconnects and a coupling region, with the interconnects providing electrical connections between features in the coupling region and the electrodes. The coupling region is arranged so as to receive a module, with the module electrically coupling to the electrodes via the features in the coupling region upon connection to the sock. The module is configured so as to deliver one or more electrical signals to the subject via one or more of the electrodes based upon a signal received from a monitoring means, such as the sensing devices or a host device coupled to the sensing devices.

In some embodiments, stimulus is focused for application to the foot of a subject. Orthotic-based approaches for stimulating devices for example, can be used to provide an interface with the bottom of the foot to provide stimuli to the subject. Specifically, an orthotic-based stimulating device may apply stimuli to the plantar region on the foot of a subject. The orthotic may be provided with similar size and shape as an insole, the orthotic including one or more stimulating electrodes, arranged along a surface thereof such that the electrodes are biased against the tissue of the foot during use. The orthotic may be inserted into a slipper, a sandal, a shoe, or the like. The electrodes may be provided with a conductive gel applied over the electrode regions so as to electrically interface with the subject during use. Unlike an adhesively applied device, the conductive gel may be slick or rubber-like so as to provide the necessary electrical interface, but not adhere to the adjacent tissues during use.

The sensing devices in a modular physiologic monitoring system, or a host device in communication with the sensing devices and the stimulating devices, are configured to monitor the state of the subject and to deliver signals to the stimulating devices in response to the monitoring.

In some embodiments, the signals may be generated by a local sensory arrangement on a sock-based stimulating device and/or a module attached thereto so as to determine a local blood oxygen level (e.g., saturation of peripheral oxygen (SpO2)) of the subject, movement of the appendage, or a signal related thereto. The signal may be used to stimulate the subject related to the monitored SpO2 levels. In some embodiments, a local assessment of the blood oxygen of the subject is performed with the module attached to the sock-based stimulating device to determine whether the levels are found to change from that of a normal person or a normal level determined for a particular subject to a depressed level. A stimulus is then provided to the actuators and/or electrodes in the sock-based stimulating devices to stimulate sensors in the plantar region of the foot of the subject. Feedback from the sensory input may be used to determine if the stimulus was effective at correcting the event.

Figure 6:
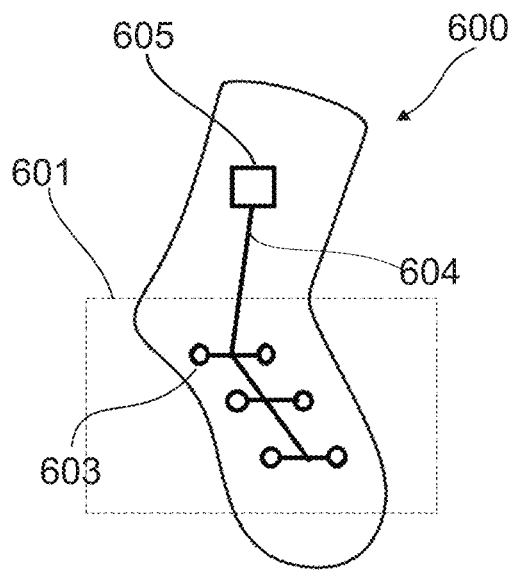
FIG. 6 illustrates a sock-like stimulating device, according to an embodiment of the invention.

FIG. 6 illustrates a sock-like stimulating device 600. As shown in the cut-out region 601, a number of electrodes, actuators and/or power modules 603 may be affixed to an interior surface of the sock 600 so as to interface with the sole of a foot of a subject when the sock 600 is worn by the subject. While FIG. 6 illustrates an arrangement wherein the electrodes 603 are on the bottom of the interior surface of the sock 600 so as to interface with the sole of the foot of a subject, one or more electrodes, power modules or other sensing or stimulus means may be placed elsewhere on the sock, such as on a top of the interior surface of the sock 600 so as to interface with a top of the foot rather than or in addition to the sole of the foot when the sock 600 is worn. Unless otherwise noted, electrodes 603 and other electrodes referred to herein may refer to electrically stimulating electrodes or various other types of stimulating means including but not limited to the means described above with respect to FIGS. 3-5. Interconnects 604 couple the electrodes 603 to one another and/or to a module 605 attached to a coupling region of the sock 600.

The stimulating device may be integrated into an insole, a sandal, a shoe, etc., where the stimulating device is attached to the subject with an interface region mounted onto an orthotic, insole, etc. The orthotic or insole may house one or more reusable components or hardware. The stimulating device or a disposable component thereof is thus easy to attach or remove. The disposable component of the stimulating device may be easily removed, with the reusable component kept within the orthotic, insole, shoe, etc. for longer term use with the subject. In some embodiments, the orthotic, insole, shoe, etc. is form fitted to the anatomy of a particular subject, the body interface attached there over, and the hardware embedded therein.

Figure 7:
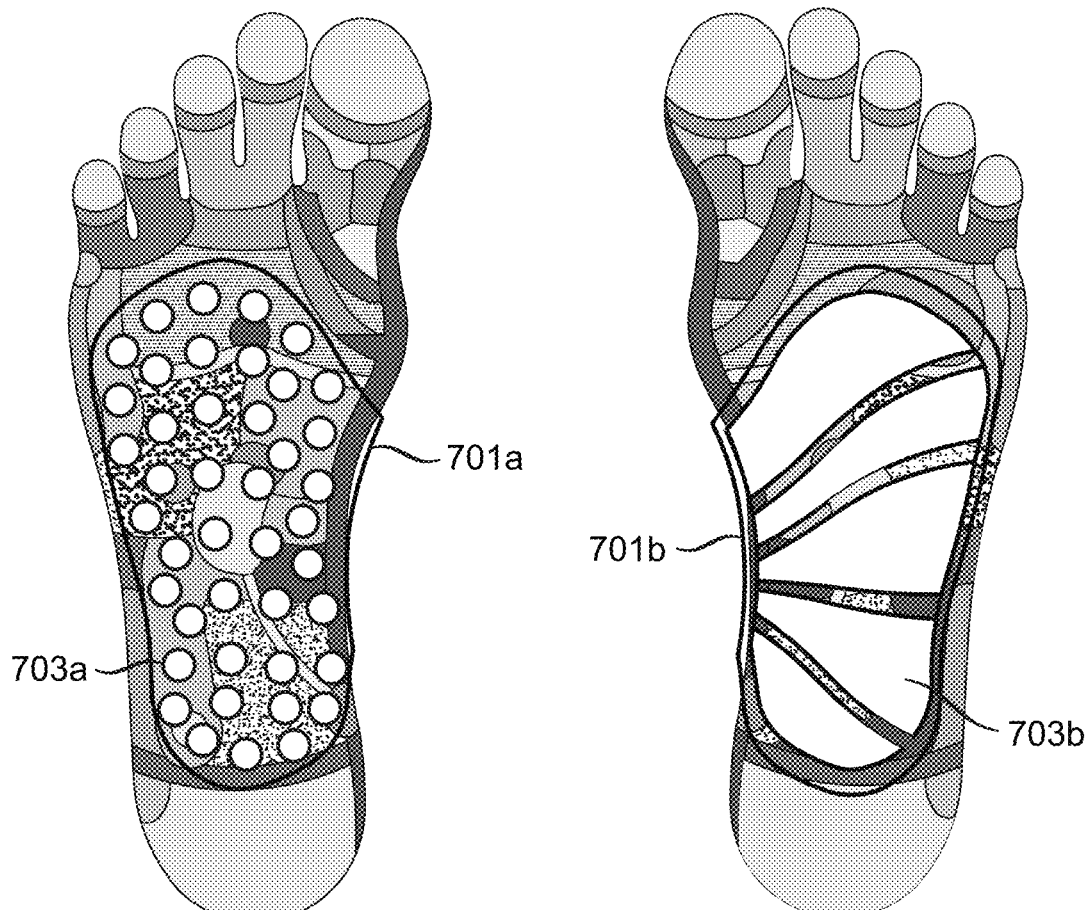
FIG. 7 illustrates arrangements of electrodes for a stimulating device configured to interface with a foot of a subject, according to an embodiment of the invention.
Figure 8:
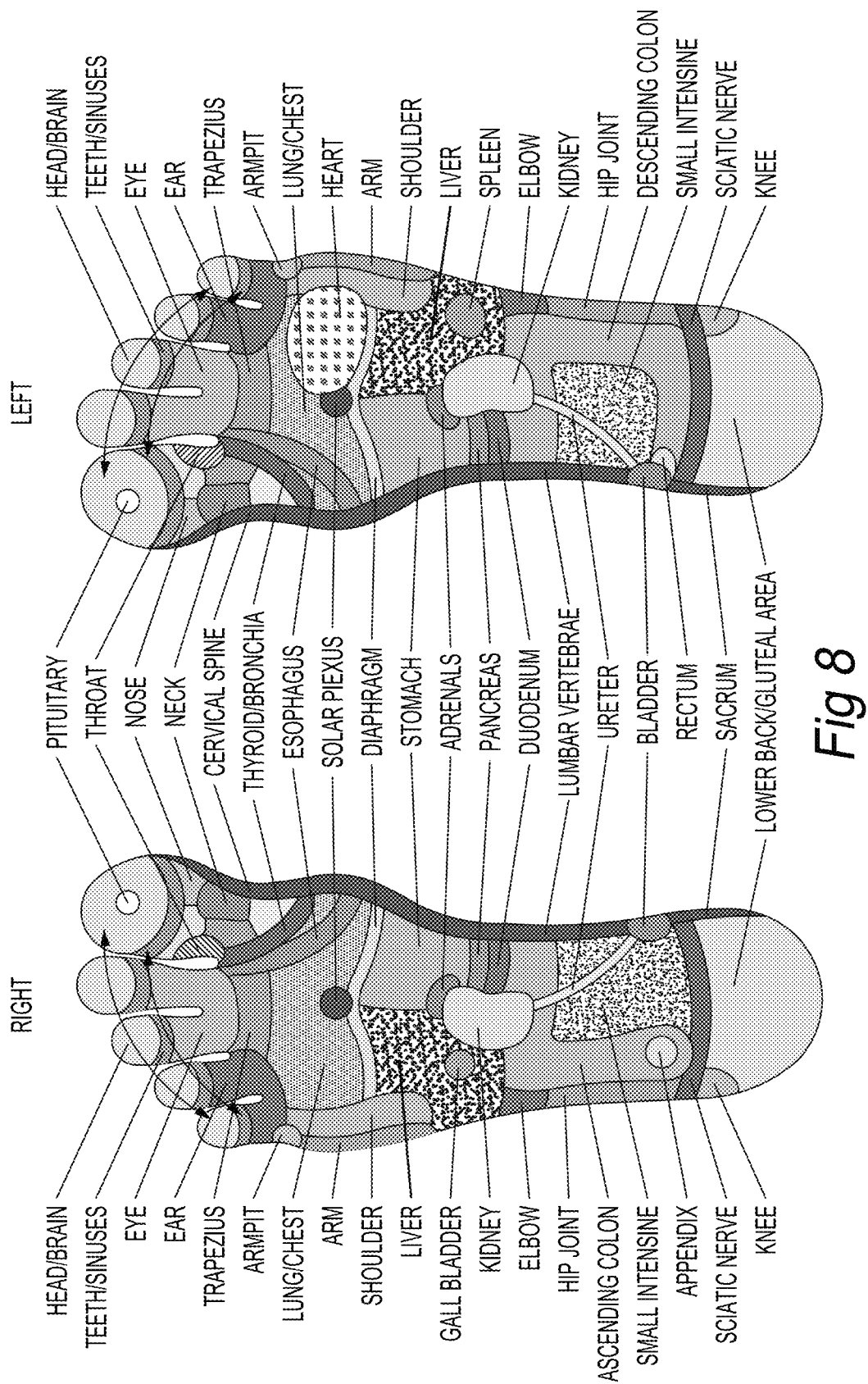
FIG. 8 illustrates regions of the foot for application of stimulus, according to an embodiment of the invention.
Figure 9:
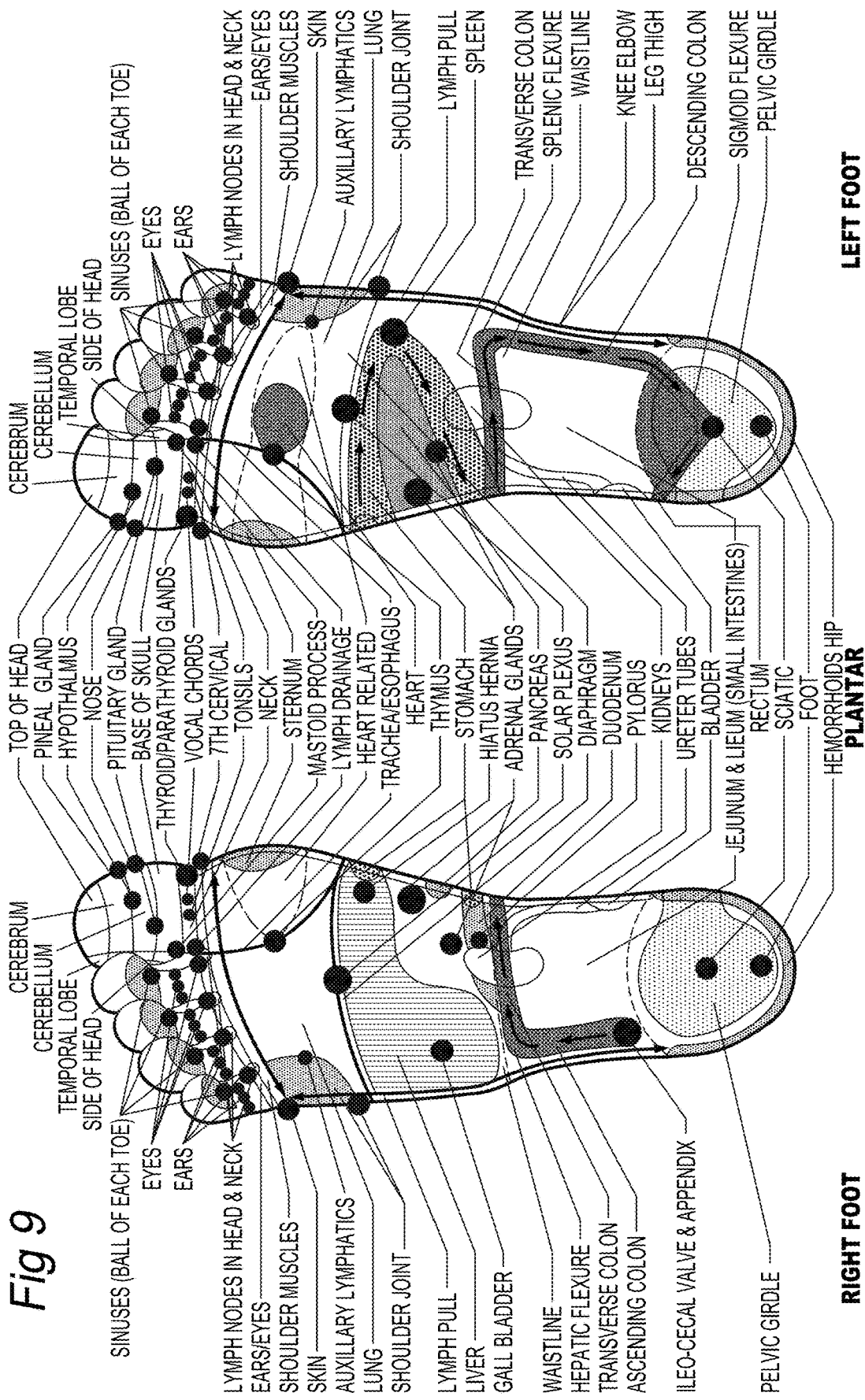
FIG. 9 illustrates regions of the foot for application of stimulus, according to an embodiment of the invention.

FIG. 7 illustrates example arrangements of electrodes or other stimulating or sensing means which may be integrated into an insole, sandal, a shoe, an orthotic, etc. The electrode arrangements shown may also be used for the interior surface of a sock form factor, the wrap form factor or other form factors configured for attachment to the foot of a subject. On the left-hand side of FIG. 7, a first electrode arrangement 701a is illustrated, with a number of smaller electrodes 703a positioned as shown. On the right-hand side of FIG. 7, a second electrode arrangement 701b is illustrated, with a number of larger electrodes 703b. The electrodes may be positioned so as to provide stimulus or input at defined regions of the foot to provide corresponding effects at various parts or regions of the body. FIGS. 8 and 9 illustrate examples of regions of the foot which may be stimulated to effect corresponding regions of the body of the subject. Although shown as distinct, in some embodiments a stimulating device, such as a sock, insole, sandal, shoe, etc. may use combinations of electrodes 703a, 703b shown in the first and second electrode arrangements 701a, 701b. For example, in some embodiments smaller electrodes 703a may be interspersed with larger electrodes 703b.

Inputs can be provided to cover various areas of the foot, including but not limited to the toes, heel, areas with dense arrays of electrodes or actuators (e.g., electrode arrangements 701a, 701b), etc. In some cases, combinations of the electrodes or actuators 703a, 703b may be used to provide multi-modal input or stimulus to the subject, such as temperature and electrical stimulation to amplify the response of one of the stimuli with a subject. In some embodiments, stimulus applied via one or more of the electrodes 703a, 703b may be monitored using one or more sensing devices in a modular physiologic monitoring system, so that the system can determine if the stimulus is of the right magnitude or spectrum, if it is generating a desired response, etc.

Figure 10:
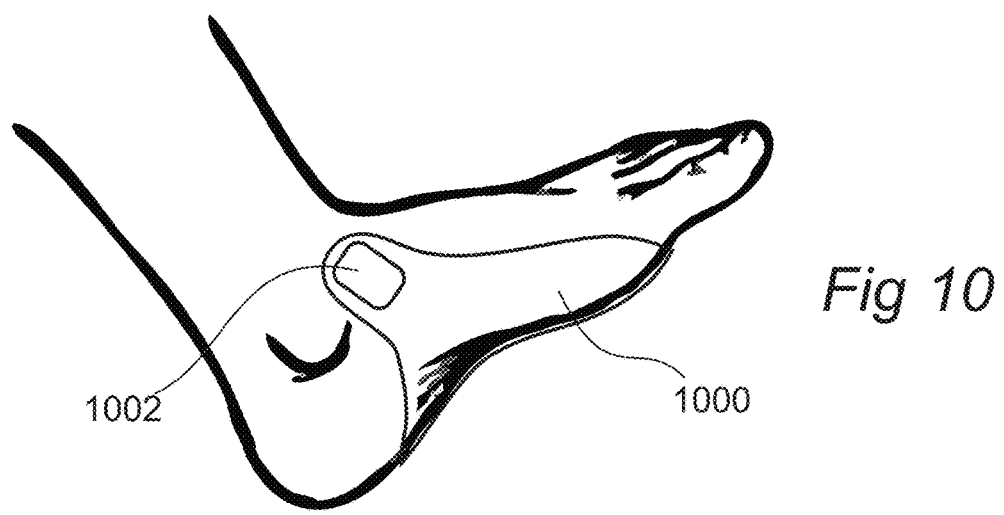
FIG. 10 illustrates a stimulating device with a disposable component and a reusable component, according to an embodiment of the invention.

In the FIG. 7 example, interconnects connecting the electrodes 703a, 703b may run up the side of the foot to electronics located on the top of the foot or on the ankle. FIG. 10 illustrates such an arrangement including a patch 1000 with a reusable module 1002 attached to the patch 1000. The patch-based stimulating device shown in FIG. 10 may be used to apply electrical stimuli to the plantar region of the foot of a subject in response to physiologic information collected from the subject using one or more sensing devices as described herein. The patch 1000 may include an electrode arrangement, such as electrode arrangements 701a and/or 701b, to interact with desired dermatomes on the foot. The reusable module 1002 can be attached and removed from the patch 1000, and is configured for communication with other devices in a modular physiologic monitoring system. The module 1002, for example, may receive signaling from a host device or from one or more sensing devices which causes the module 1002 to direct electrodes on the patch 1000 to apply stimuli to target regions of the foot of the subject.

FIGS. 11a-e illustrate non-limiting examples of patch electrode layouts.

Figure 11A:
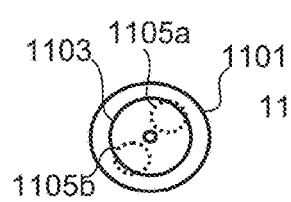
FIGS. 11a-11e illustrate electrode layouts, according to an embodiment of the invention.

FIG. 11a shows a patch 1101 coupled to a module 1103. The patch 1101 includes a plurality of electrodes 1105a, 1105b for interfacing with a subject. The electrodes 1105a, 1105b are arranged in a very tight bipolar arrangement suitable for obtaining a bipolar electrical reading from the surface of a subject with a very small profile. In aspects, one or more of the electrodes 1105a,b may include an electrode feature for enhancing the electrical coupling between the module 1103 and the underlying tissues of a subject. In aspects, pressure applied to the top of an attached module 1103 may be suitable for engaging such an electrode feature with the underlying tissue of the subject. Such an arrangement may be advantageous for providing an ultra-miniature heart-rate monitor, a pediatric heart-rate monitor, an EMG sensor for placement near a sexual organ, an electrophysiological monitor behind an ear, on a neck, etc., and/or to provide a stimulating device as described herein.

Figure 11C:
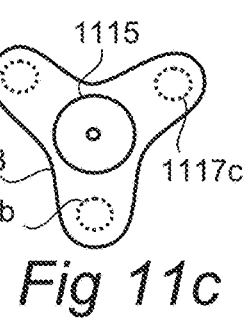
Figure 11E:
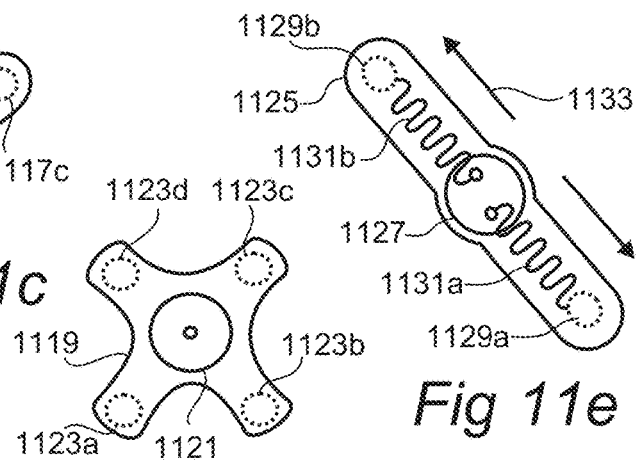
Figure 11B:
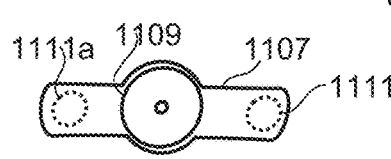

FIG. 11b shows a patch 1107 coupled to a module 1109. The patch 1107 includes a bipolar electrode arrangement 1111a, 1111b for interfacing with a subject. Such an arrangement may be advantageous for monitoring heart-rate, a signal channel EKG, respiration rate, etc. of a subject as part of a monitoring session, and/or to provide a stimulating device as described herein. A plurality of such patches 1107 may be applied to a subject to simultaneously extract a higher level or spatially distributed electrical field over the body of the subject.

FIG. 11c shows a patch 1113 coupled to a module 1115. The patch 1113 includes three electrodes 1117a, 1117b, 1117c for interfacing with a subject. The electrodes 1117a, 1117b, 1117c may be arranged so as to allow for multi-site capture of electrophysiological activity on the subject. Such an arrangement may be advantageous for generating a field vector in the vicinity of the patch 1113, and/or for applying a stimulus to the subject.

Figure 11D:

FIG. 11d shows a patch 1119 coupled to a module 1121 each in accordance with the present disclosure. The patch 1119 includes a quadripolar electrode arrangement 1123a, 1123b, 11123c, 1123d for interfacing with a subject. The quadripolar electrodes 1123a, 1123b, 1123c, 1123d may be arranged so as to allow for multi-site capture of electrophysiological activity on the subject, and/or for applying stimuli to the subject. Such an arrangement may be advantageous for generating a field vector in the vicinity of the patch 1119, for mapping electric field propagation across the surface of the subject, etc.

FIG. 11e shows a patch 1125 coupled to a module 1127 each in accordance with the present disclosure. The patch 1125 includes a plurality of electrodes 1129a, 1129b for interfacing with a subject. The electrodes 1129a, 1129b are shown in a bipolar arrangement connected to stretchable conducting elements 1131a, 1132b. In aspects, such a configuration may be advantageous to freely flex and stretch 1133 along with the nearby tissues of the subject during a monitoring and/or stimulating session. The stretchable conducting elements 1131*a*, 1131*b* may be arranged so as to repeatably change impedance during stretch. Such a configuration may be advantageous for assessing movement under the patch (e.g., due to muscle movement, breathing, etc.) in conjunction with one or more physiologic signals (e.g., such as electrophysiological signals, stretch related artifact, etc.) in accordance with the present disclosure. Such a configuration may be suitable for physiotherapy monitoring sessions (e.g., combined proprioceptive monitoring in conjunction with EMG, assessing breathing in conjunction with EKG, gait assessment, a running gait correction system, etc.).

Figure 12A:
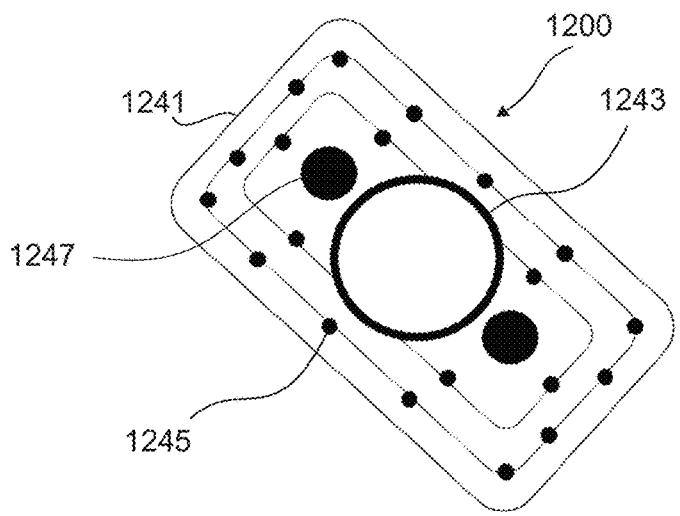
FIGS. 12a-12c illustrates a patch-module pair that is applied to the sole of a foot of a subject, according to an embodiment of the invention.

FIG. 12*a* shows a patch-module pair 1200 including a patch 1241 coupled to a module 1243. The patch 1241 is substantially rectangular, and suited for attachment to the foot of a subject. The patch 1241 includes a number of sensing electrodes 1245 and a number of stimulating electrodes 1247. The module 1243 includes various electronics, including but not limited to a battery. Each of the electrodes 1245, 1247 may be monopolar, bipolar or multipolar as desired.

Figure 12B:
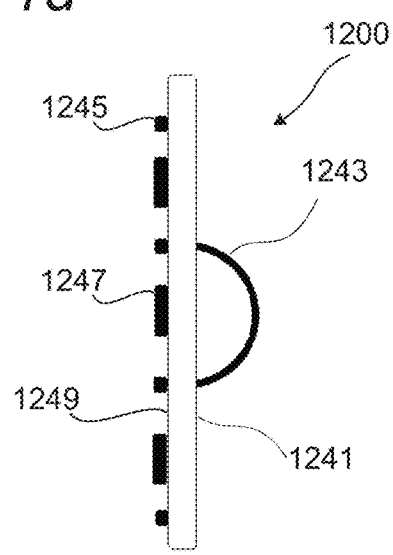

FIG. 12*b* shows a side view of the patch-module pair 1200, illustrating that the electrodes 1245, 1247 and an adhesive 1249 are on a first side of the patch 1241 while the electronics of module 1243 are on an opposite side of the patch 1241. It is to be appreciated, however, that in some embodiments electronics such as module 1243 may be on the same side of a patch as electrodes 1245, 1247.

Figure 12C:
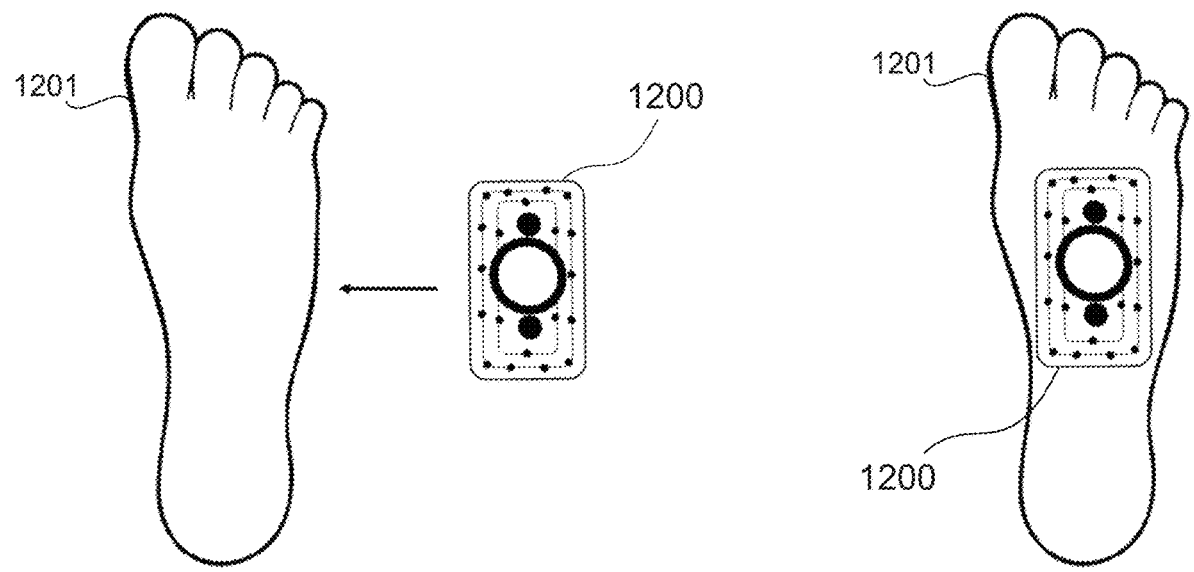

FIG. 12*c* shows the patch-module pair 1200 applied to the sole of a foot of a subject 1201. FIG. 12*c* shows the patch-module pair 1200 before and after attachment to the sole of the foot of the subject 1201.

In a glove form factor, the stimulating device may be integrated into the glove such that stimulus is provided to a region of the palm of the hand on which the glove is worn or to a wrist, a finger or the like. The glove may include one or more stimulus generating components (e.g., thermomechanical devices, electrodes, etc.) coupled with one or more other hardware components. In some embodiments, a flexible interface may be incorporated into the glove so as to provide the interface along with coupling elements to couple the interface with reusable hardware components.

Figure 13:
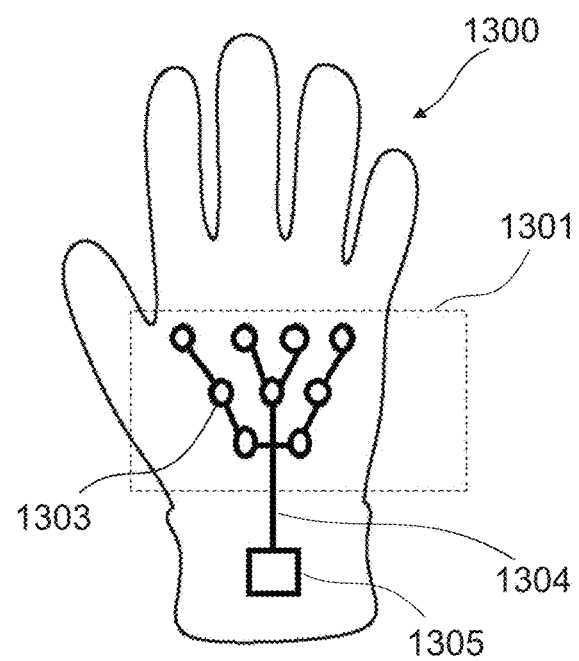
FIG. 13 illustrates a glove-like stimulating device, according to an embodiment of the invention.

FIG. 13 illustrates a glove-like stimulating device 1300. As shown in the cut-out region 1301, a number of electrodes and/or power modules 1303 may be affixed to an interior surface of the glove 1300 so as to interface with the palm of a hand of a subject when the glove 1300 is worn by the subject. It is to be appreciated that electrodes 1303 may be placed as desired within the glove 1300, so as to interface with one or more fingers of the subject when the glove 1300 is worn, the back of the hand of the subject when the glove 1300 is worn, etc. in addition to or in place of electrodes configured to interface with the palm of the hand of the subject. Interconnects 1304 couple the electrodes 1303 to one another and/or to a module 1305 attached to the glove 1300.

The stimulating device may also take the form of a wrap, as opposed to a sock, glove sandal, etc. The wrap may be configured for application to various regions of the body of the subject, including but not limited to the feet, hands, wrists, ankles, genitals, etc. The wrap may be configured with a region having one or more stimulating elements (e.g., electrodes, etc.) oriented such that, when wrapped around the target anatomy, the stimulating elements interface with target tissues. The wrap may include stretchable conducting interconnects coupling the stimulating elements to reusable hardware elements or components. The wrap may be single-use disposable or multiple-use disposable, while the hardware may be reused indefinitely.

A stimulating device may be provided as an earbud or earphone, optionally with access to the mastoid region as a site for input of stimulus to the subject. Such a device may include one or more means for providing audible stimuli to the subject. The device may also or alternatively include one or more actuators for orientation along the ear canal and/or along the mastoid region so as to provide vibrational and/or mechanical stroking type input or stimulus to the subject along key dermatomes.

Figure 14:
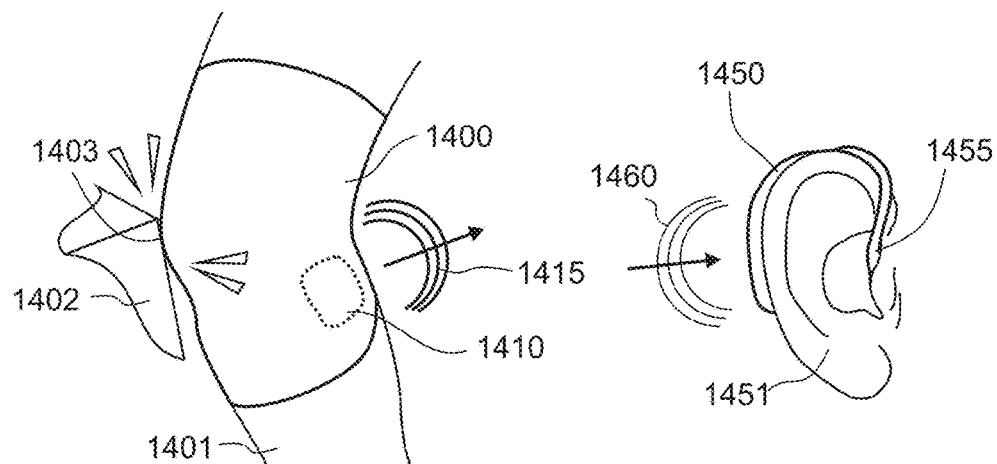
FIG. 14 illustrates wrap-like and earbud sensing and stimulating devices, according to an embodiment of the invention.

FIG. 14 illustrates stimulating and sensing devices in the form of wrap 1400 and earbud 1450. The wrap 1400 provides an impact sensing patch integrated into a knee brace on a subject 1401. The wrap 1400 may include one or more piezoresistive materials (e.g., materials that change electrical properties or charge storage thereupon in relation to strains placed thereupon), a capacitive stretch sensor, a pressure sensitive nano-composite structure, or the like. Upon impact 1403 of the wrap 1400 with an object 1402, a coupled module 1410 may send one or more signals 1415 to earbud 1450, a host device, etc.

The earbud 1450 is attached to the ear 1451 of the subject or to another individual associated with the subject such as a caregiver. The earbud may receive signaling 1460 (e.g., directly from wrap 1400, one or more other sensing devices, a host device, etc.) and produce a feedback signal or other input or stimulus (e.g., an audio signal, a vibration signal, a tactile signal, a visual signal, etc.) for delivery to the subject. In the FIG. 14 example, the earbud 1450 produces audible feedback or stimulus to the ear 1451 via a loudspeaker 1455.

The combination of wrap 1400 and earbud 1450 may be advantageous for monitoring impacts on a subject with neuropathy (e.g., lack of sensation in an extremity, for assistance with gait analysis, for providing feedback during exercise, etc.) and providing feedback or stimulus in response thereto, such as by providing the subject with a transferred sensation of touch in a region of their body that still has sensation (e.g., via a tactile feedback component, audible cue, visual cue, etc.), or for formation of a feedback loop to a touch related event.

The wrap 1400 can measure interfacial pressure information and provide it to the earbud 1450 or another stimulating device. As mentioned above, such an arrangement is useful for helping a subject feel in a region of the body that has no feeling, assisting with recovery of feeling in a region during physiotherapy, etc. Although FIG. 14 illustrates an example wherein the wrap 1400 acts as a sensing device, in other embodiments wrap-like devices may function as stimulating devices. In addition, the use of earbud 1450 as a stimulating device is presented by way of example only, and a wide variety of other types of stimulating devices may be used in conjunction with wrap 1400 as described herein.

For a ring or band form factor, the ring or band may be applied to one or more fingers, toes, genitals, wrist or the like so as to interface with nerves in the vicinity thereof. The ring or band may include a plurality of electrodes on the underside thereof, one or more vibrating elements, one or more thermal elements or other stimulating hardware components. The ring or band may include additional hardware components to wirelessly receive signals from an external device, the external device generating the signals to apply stimulus to the subject through the interface via the electrodes, vibrating elements, thermal elements or other stimulating hardware components.

Figure 15:
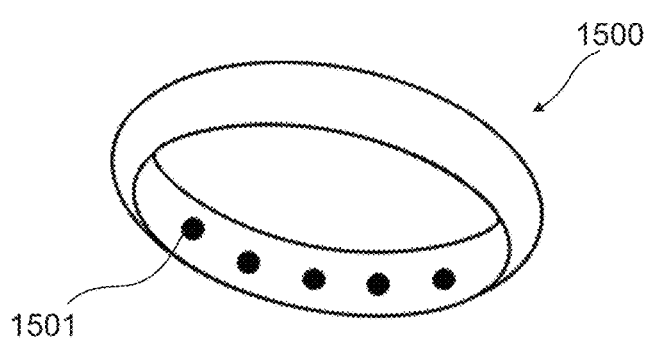
FIG. 15 illustrates a ring- or band-like stimulating device, according to an embodiment of the invention.

FIG. 15 illustrates a ring- or band-like stimulating device 1500. As shown, the ring 1500 includes a number of electrodes 1501 on an interior surface thereof, configured to interface with the skin of a subject when the ring 1500 is worn. Although not explicitly shown, the electrodes 1501 may be coupled to one another and/or to a module configured for attachment to or communication with the ring 1500.

A face cover may provide a form factor for audio and/or visual input to the subject. The face cover may be, for example a wearable sleep mask with audio and/or visual means to provide stimuli to the subject during sleep. The mask may be wirelessly coupled with an external system or host device, with the external system providing signals to direct stimulation by the audio and/or visual means of the mask. In aspects, the mask or other face cover may include one or more sensors for interfacing with the subject to provide for monitoring of EEG, EOG, facial EMG, or the like, in combination with the ability to provide stimuli to the subject when an event occurs.

Figure 16:
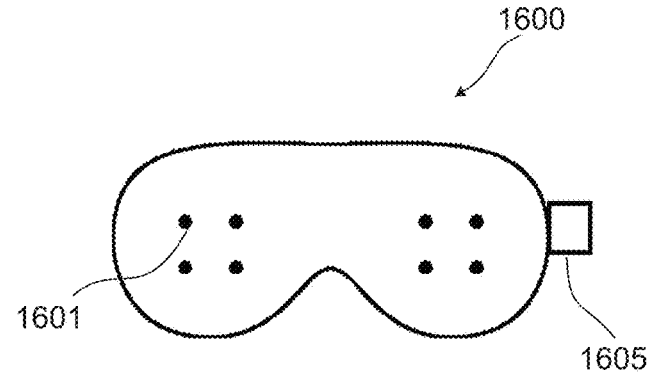
FIG. 16 illustrates a face cover stimulating device, according to an embodiment of the invention.

FIG. 16 illustrates a face cover stimulating device in the form of a sleep mask 1600. As shown, the sleep mask 1600 includes a number of elements 1601 on an interior surface thereof, such that when the sleep mask 1600 is worn by a subject the elements 1601 may provide a stimulus (e.g., an audible stimulus, a visual stimulus, etc.) to the subject. The elements 1601 may be speakers, light-emitting devices such as light-emitting diodes (LEDs), etc. In some embodiments, the elements 1601 may represent pixels on a video screen for displaying images to the subject. A module 1605 is shown attached to the face cover 1600. The module 1605 may be coupled to one or more of the elements 1601.

A non-contacting stimulating device may be, for example and audio and/or visual system, a heating or cooling system, etc. Smart speakers and smart televisions or other displays are examples of audio and/or visual non-contacting stimulation devices. A smart speaker, for example, may be used to provide audible stimulus to the subject in the form of an alert, a suggestion, a command, music, other sounds, etc. Other examples of non-contacting stimulation devices include means for controlling temperature such as fans, air conditioners, heaters, etc.

One or more stimulating devices may also be incorporated in other systems, such as stimulating devices integrated into a bed, chair, operating table, exercise equipment, etc. that a subject interfaces with. A bed, for example, may include one or more pneumatic actuators, vibration actuators, shakers, or the like to provide a stimulus to the subject in response to a command, feedback signal or control signal generated based on measurement of one or more physiologic parameters of the subject utilizing one or more sensing devices.

Although the disclosure has discussed devices attached to the body for monitoring aspects of the subject's disorder and/or physiologic information, as well as providing a stimulus, therapeutic stimulus, etc. alternative devices may be considered. Non-contacting devices may be used to obtain movement information, audible information (such as snoring), skin blood flow changes (e.g., such as by monitoring subtle skin tone changes which correlate with heart rate), respiration (e.g., audible sounds and movement related to respiration), and the like. Such non-contacting devices may be used to supplement an on-body system or for the monitoring of certain conditions (e.g., such as snoring, an obvious apneic event, etc.) be a source of alert or event information, stimulus, etc. Information captured by non-contacting devices may, on its own or in combination with information gathered from sensing devices on the body, be used to direct the application of stimulus to the subject, via one or more stimulating devices on the body and/or via one or more non-contacting stimulating devices.

In some embodiments, aspects of monitoring the subject utilizing sensing devices in the modular physiologic monitoring system may utilize sensing devices that are affixed to or embodied within one or more contact surfaces, such as surfaces on a piece of furniture on which a subject is positioned (e.g., the surface of a bed, a recliner, a car seat, etc.). The surface may be equipped with one or more sensors to monitor the movement, respiration, HR, etc. of the subject. To achieve reliable recordings, it as advantageous to have such surfaces be well positioned against the subject. It is also advantageous to build such surfaces to take into account comfort level of the subject to keep the subject from feeling the sensing surfaces and to maintain use of the sensing surface over time.

Stimulating devices, as discussed above, may take the form of audio, visual or audiovisual systems or devices in the sleep space of the subject. Examples of such stimulating devices include smart speakers. Such stimulating devices provide a means for instruction a subject to alter the sleep state thereof. The input or stimulus may take the form of a message, suggestion, command, audible alert, musical input, change in musical input, a visual alert, one or more lights, a combination of light and sound, etc. Examples of such non-contacting stimulating devices include systems such as Amazon Echo®, Google Home® and the like.

Figure 17:
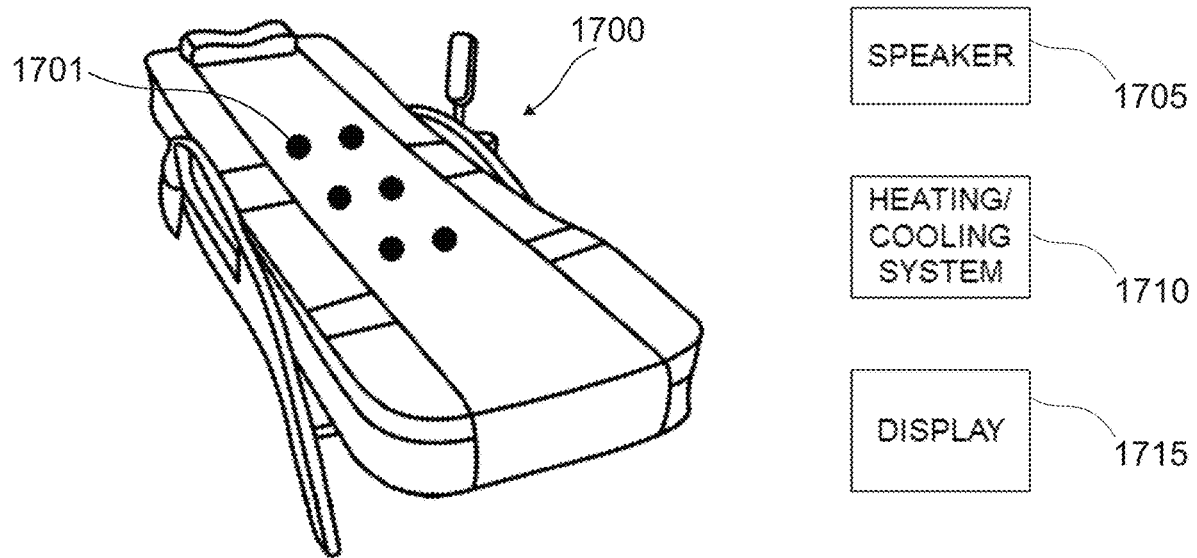
FIG. 17 illustrates a stimulating device incorporated into a contact surface and non-contacting stimulating devices, according to an embodiment of the invention.

FIG. 17 illustrates a stimulating device incorporated into a bed 1700, along with a number of non-contacting stimulating devices such as a speaker 1705, a heating and cooling system 1710 and a display 1715. The bed 1700 includes one or more electrodes 1701. As shown, the electrodes 1701 are configured to interface with a back of the subject while the subject lies on the bed 1700. The non-contacting stimulating devices may be arranged so as to provide stimuli to the subject while the subject is lying on the bed. For example, the speaker 1705 may be placed as desired to provide audible stimulus. The heating and cooling system 1710 may take the form of a general air conditioning unit in a room in which the bed 1700 is placed, a heater in the room in which the bed is placed, a vent or fan in the room configured to blow cool or hot air at one or more desired areas of the bed 1700, etc. The display 1715 may take the form of a television, projector, etc. positioned so as to be viewed by the subject while the subject lays on the bed 1700.

Figure 18:
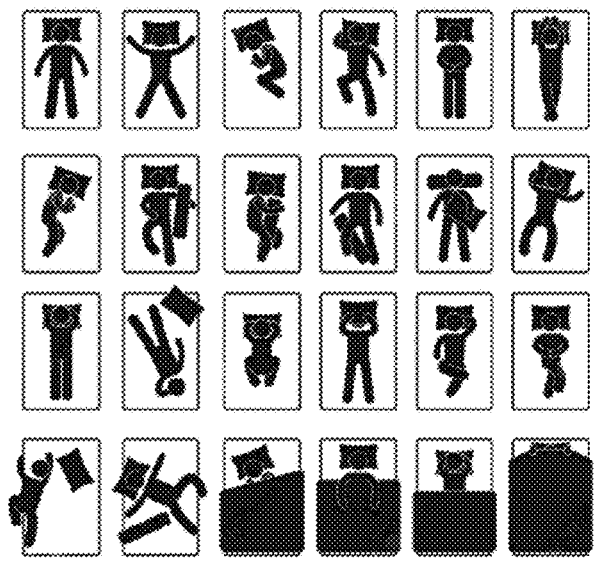
FIG. 18 illustrates sleep postures, according to an embodiment of the invention.

As described above, a modular physiologic monitoring system may include a number of sensing devices which may be utilized to determine posture or relative positioning of different region of the body of a subject. FIG. 18 illustrates various sleep postures, for example. Sensing devices may be arranged on the subject, in or on contacting surfaces such as a bed of the subject, or on a non-contacting device such as cameras which can record images of the subject, etc. Such sensing devices can be used to determine sleep posture at a macro level (e.g., which side of the body is "up" or "down"), whether a region of the body is covered or uncovered, etc. The macro sleep posture may be used to assess positioning of the subject with respect to events detected during sleep. If a sleep event (e.g., an apneic event, snoring, etc.) is postural in nature, corrective stimuli can be sent such that when the subject moves into a different sleep posture, either to avoid a sleep event before it happens or to correct an ongoing sleep event. Sleep posture may also be adjusted via corrective stimuli to encourage better postures to increase sleep quality, avoid pain (e.g., back pain from sleeping in certain positions, etc.).

Figure 19:
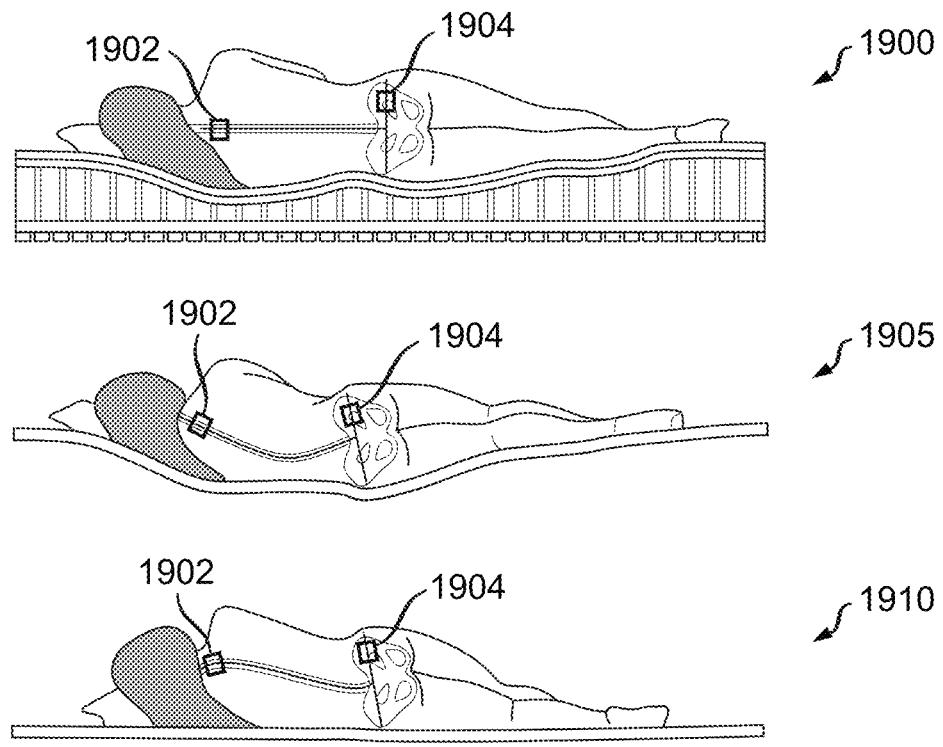
FIG. 19 illustrates multiple sensing devices attached to a subject for measuring orientation, according to an embodiment of the invention.

Multiple sensing devices in a modular physiologic monitoring system may also be used to obtain information relating to the relative orientation or positioning of different regions or parts of the body of a subject. FIG. 19, for example, illustrates two sensing devices 1902 and 1904 placed on the neck and lower back of a subject, respectively, as the subject moves between positions 1900, 1905 and 1910. Information obtained from the sensors 1902 and 1904 may be used to compare posture of different regions of the body in various ways (e.g., using orientation vectors with respect to gravity, obtaining inter-device orientation information in combination with barometers to determine height differences between devices in a gravitational field, etc.). Collectively, multiple sensing devices may be utilized to determine spinal alignment, neck alignment, pelvic alignment, etc. during sleep. The sensing devices 1902 and 1904, in some embodiments, may also be configured to monitor local EMG to determine local muscle spasms during monitoring of a subject in conjunction with posture.

Figure 20:
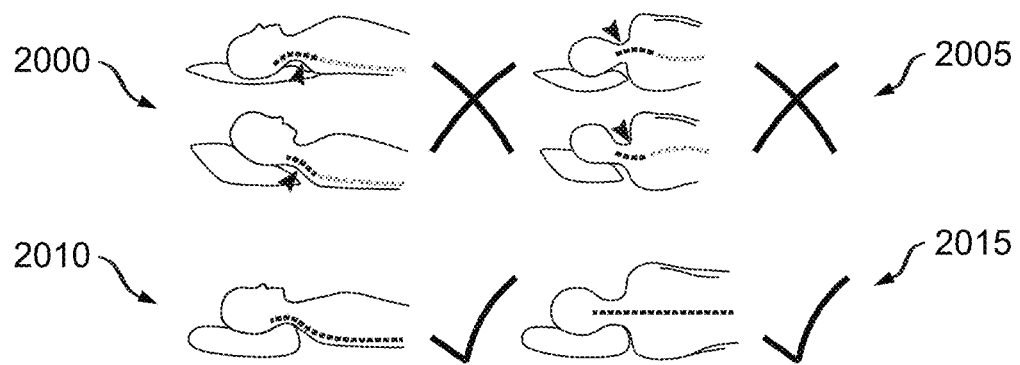
FIG. 20 illustrates sensing devices for measuring neck alignment, according to an embodiment of the invention.

FIG. 20 illustrates an example wherein sensing devices placed on the head/neck and torso of a subject (not explicitly shown) may be used to monitor neck alignment of a subject. Positions 2000 and 2005 show examples of neck misalignment while positions 2010 and 2015 show examples of proper neck alignment.

A modular physiologic monitoring system may be used to sense physiologic parameters associated with physical exertion. A number of physiologic parameters may be combined or integrated to determine a state of physical status of a subject. For example, one or more sensing devices may be used to provide levels of heat stress, or information which may be utilized to derive levels of heat stress, where the levels of heat stress and possibly other parameters are integrated to provide a real-time assessment of the current state of the subject and to measure progress to a state associated with more or less physical stress. The modular physiologic monitoring system may provide warnings, either analog or digital (e.g., numbers, colors shapes) as feedback or stimulus (e.g., telemetry including wireless telemetry) to the subject or to a remote monitoring system, physician, caregiver, etc.

To monitor physical exertion, such as body temperature and fatigue, a modular physiologic monitoring system in some embodiments utilizes an adhesive patch with multiple sensing capabilities as the sensing device(s). A patch may be configured with several components with differing specific heat conduction characteristics. The patch may include or be configured with one or more insulating regions with low heat transmission, one or more thermally conducting regions, a plurality of temperature sensors, one or more environmental sensors, combinations thereof and the like.

An insulating region of the patch is placed over the skin, and is configured to limit local heat transfer from the skin to the surroundings (e.g., to form a local region with warm skin and/or to limit skin heat loss). The insulating region may cause arteriolar or vascular vasodilation. One or more thermal sensors may be positioned at the skin site under insulating regions of the patch. Blood temperature under the insulating region will be close to the core body temperature of the subject, and thus permits superficial measurement of core body temperature. The insulating region of the patch may also cause sweating or perspiration of the subject. As sweat is derived from blood, the sweat temperature, if prevented from cooling, can provide a good measure of core body temperature and/or blood temperature.

A thermally conducting region of the patch is placed over the skin, and is configured to allow for maximal heat transfer from the skin to the environment. The conducting region will have a strong tendency to remain at a basic skin temperature.

A plurality of temperature sensors may be arranged in the various insulating and/or thermally conducting regions of the patch, and configured to measure temperature in such regions. The plurality of temperature sensors may also include one or more sensors arranged along a vector substantially normal to the skin surface so as to measure a thermal gradient there along.

Environmental sensors on the patch may be configured to estimate thermal properties of the immediate surroundings of the patch. Such thermal properties include but are not limited to humidity (e.g., measured with an onboard and/or remote sensors), local air temperature, local air velocity and/or turbidity, a barometer to give local ambient pressure changes, an immediate light vicinity sensor (e.g., for measurement of ambient light or infrared to a region of the patch), etc.

The patch, a module attached thereto, or a host device in communication with the patch and/or module is configured with a thermal difference algorithm configured to derive thermal gradients from the multiple temperature sensor readings and to make a prediction or estimation of core body temperature, heat loss, metabolism, etc. The patch may also include one or more physiologic sensors, with measurements therefrom being used to derive parameters such as heat loss, metabolism, efficiency or the like from the subject.

In one embodiment, the system may include a plurality of temperature sensors, each temperature sensor situated in/on the patch or hub module. Each temperature sensor may be positioned such that it has a substantially known thermal transfer characteristic with respect to one or more surfaces of the module and/or the patch. In one embodiment, the module includes a plurality of temperature sensors, one or more sensors being situated substantially near the top surface of the module (e.g., the surface that faces outward from the subject and towards the surrounding environment during use) and one or more temperature sensors being situated substantially near the bottom surface of the module (e.g., the surface that is biased against a patch and/or skin surface of a subject during use). The temperature readings obtained by the sensors located nearest to the skin of the subject are more reflective of the skin temperature of the subject at the site of application to the subject, while the temperature readings obtained by the sensors located nearest to the environment of the subject are more reflective of the environmental temperature surrounding the location of application of the module to the subject. Collectively, the temperature readings from the plurality of sensors may be used to determine the skin temperature of the subject as well as the local heat loss from the subject during use.

In addition to temperature sensing, one or more humidity sensors, fluid velocity sensors (e.g., an anemometer, a microelectromechanical system (MEMS) based anemometer, a MEMS hotwire anemometer, etc.), and/or barometers may be added to the module or the patch so as to increase the environmental information obtained during usage. In one non-limiting example, a humidity sensor may be located in the module near to the top surface thereof, the humidity sensor used to determine the local humidity around the module during use, the thermal transfer characteristic to the surrounding environment determined at least in part with the assistance of the humidity sensor. In another non-limiting example, a MEMS based micro-anemometer is placed into the module near to the upper surface thereof, the local airflow velocity and/or heat transfer characteristics to the surrounding environment in the vicinity of the module determined at least in part with measurements obtained from the micro-anemometer.

In one non-limiting example, a temperature sensor may be integrated into the patch. The integrated temperature sensor may have a thickness of less than 0.2 mm, less than 0.1 mm, less than 0.05 mm, or the like. The sensor may be coupled to one or more conducting traces in the patch, so as to provide an electrical interface thereto. The temperature sensor may be used to determine the temperature and/or heat transfer characteristic at a site on the subject, substantially removed from the vicinity of the module.

In one non-limiting example, a plurality of temperature sensors may be integrated into the module and/or patch, and one or more thermally controlled features may be added there-over or there-under so as to influence a heat transfer characteristic and/or heat capacity in the vicinity thereof. In one non-limiting example, a thermally insulating material (e.g., a fibrous material, an aerogel, a porous foam material, or the like), or a thermally conducting material (e.g., a metallic composite, a thermally conducting ink, a metal foil, or the like), may be added as the thermally controlled feature. In aspects, the thermally controlled feature may be inserted so as to bias the temperature reading obtained by the temperature sensor to be closer to that of the local skin temperature, and in aspects the thermally controlled feature may be inserted so as to bias the temperature reading obtained by the temperature sensor so as to be closer to that of the surroundings. In aspects, matched temperature sensors may be placed into the patch in close vicinity to one another, and one or more thermally controlled features applied such that a differential reading may be obtained from otherwise calibrated sensors. The differential reading may be used to determine the local heat flux from the skin of the subject during use.

The thermal transfer characteristics (e.g., the heat transfer characteristics, the heat capacity, the internal thermal source characteristics of the module, etc.) may be determined a priori or during a calibration procedure. The heat transfer through the module may be determined by the temperature differences of the temperature sensors located near to the top surface and near to the bottom surface of the device.

In some usage scenarios, one or more current sensors in the device may be used to determine the extent of one or more thermal sources within the module and/or patch of the subject. In one non-limiting example, the thermal sources may include inefficiency in the battery, the power management circuitry, the radio, and one or more components in the device. In aspects, a thermal source map may be generated a priori from the layout and power consumption information (e.g., power consumption determined by one or more current readings), so as to determine the location of the heat sources, and, in particular, any dominant thermal source within the module during use. Such thermal source information may be added to a thermal model of the module so as to more precisely predict the heat transfer through the device during use. In one usage scenario, a controlled heating of one or more components may be used as part of a calibration procedure.

In some usage scenarios, the insulation of the clothing, blanket, etc. on the subject may influence the heat transfer from the subject to the environment. Thus the heat flux through the module may change along with this level of insulation. In one non-limiting example, when the heat flux through the module approaches zero, the skin temperature may approach that of the core temperature of the subject.

In one non-limiting usage scenario, the module and/or patch may include one or more electromyographic sensors so as to determine local muscle activity during use. Optionally, the module and/or patch may also include one or more stretch sensors and/or one or more inertial sensors so as to determine movement of one or more nearby muscle groups during use. During a period of physical activity, the extent and type of muscle activity may be determined by the EMG sensor, the activity sensor, and/or the stretch sensor. Simultaneously, one or more of the temperature sensors may be monitored before, during, and/or after the physical activity to determine the local temperature increase and/or heat transfer from the muscle during use. Collectively, such information may be combined so as to determine the energy expenditure of the muscle group as well as the efficiency of the muscle group to the physical activity under test. Such information may be used to guide training, demonstrate changes in the capability and/or efficiency of a muscle group over time, to determine the extent of muscle strength improvements, etc. during use. Such information may be advantageous for determining/guiding progress of a subject during physiotherapy, during training, for evaluating the athletic capability of a subject, etc.

In one non-limiting usage scenario, in particular directed towards care of an infant or a premature infant in a Kangaroo care setting, a patch-module pair may be placed onto the torso of the infant. In aspects, the device may include a plurality of temperature sensors, one or more inertial sensors, one or more orientation sensors, one or more pulse oximetry sensors, one or more electrocardiographic sensors, one or more respiratory sensors, one or more humidity sensors, or the like.

The plurality of temperature sensors may be used to determine the state of contact between the infant and the mother. In particular, when the infant is optimally oriented against the body of the mother, the thermal gradient measured by the plurality of the temperature sensors may approach zero, the temperature measurements obtained from the sensors may approach the body temperature collectively of the mother and the infant, the orientation sensors may indicate that the head of the infant is correctly oriented with respect to gravity (e.g., the head of the infant is oriented up with respect to gravity), the heart rate of the infant is in a normal range, the humidity of the environment around the infant is high, the SpO2 reading of the infant is within a normal range (e.g., greater than 96%). When the orientation and/or positioning of the infant with respect to the parent is sub-optimal, one or more of the subsystems may provide corresponding information, and an alert may be made, a feedback signal to the parent figure to assist with correcting the positioning of the infant, or the like may be made. Such a system may be advantageous to assist a parent figure with performing of Kangaroo care in a general usage environment.

In one non-limiting embodiment, a patch used in a Kangaroo care scenario may be configured with a plurality of electrophysiologic sensors (e.g., electrodes). The plurality of electrodes may include two or more down facing electrodes positioned so as to contact the skin of the infant during use, and two or more up facing electrodes positioned so as to contact the skin of the parental figure during proper implementation of Kangaroo care. In one usage scenario, when the infant is properly positioned against the skin of the parental figure, the up facing electrodes may contact the skin of the parental figure. The up facing electrodes may be coupled to one or more circuits used to determine the skin impedance of the parental figure, one or more electrophysiologic signals from the parental figure, and/or one or more electrodermal signals from the parental figure. In aspects, the down facing electrodes may be used to determine one or more similar signals from the infant. During proper implementation of the Kangaroo care procedure, the electrophysiologic information from both parent and child may be determined. In aspects, the characteristics of the electrocardiographic signal obtained from the up facing electrodes may be used to determine the position of the infant against the torso (e.g., with respect to orientation of the heart) of the parent figure during use. Such information may be combined with the orientation information obtained from the orientation sensors to determine the orientation state of the infant with respect to gravity as well as with respect to the torso of the parental figure during use.

In one non-limiting application, an embodiment in accordance with the present disclosure may be used to monitor a subject for heat exhaustion, dehydration, fatigue, or the like. In such usage scenarios, the embodiment may include a plurality of sensor types including one or more temperature sensors, one or more electrophysiologic sensors, one or more activity sensors, one or more orientation sensors, or the like. During use, a data set may be generated from data collected with each sensor system, the data set collectively containing data related to the physiologic state of the subject, the orientation of the subject, and the state of the environment in the vicinity of the subject. Some non-limiting examples of collected data may include ECG, heart-rate, heart-rate-variability, Q-T period, ST segment amplitude, QRS amplitude, respiration rate, respiration depth, respiration character, skin temperature, core temperature, local heat flux, local orientation, local inertial information, local humidity, low air temperature, local airflow rate, and the like. The changes of the physiologic data (e.g., ECG, heart rate, respiration, etc.) in combination with movement, and environmental information, may be correlated to assess the fatigue state, hydration state, and/or heat exhaustive state of the subject.

In one non-limiting example, the correlation may be determined by comparing the heart rate recovery (HRR) and/or temperature recovery of the subject after a period of physical activity. As the subject becomes exhausted, the HRR changes, temperature recovery changes, and HRV changes with respect to the relationships observed during a normal state of the subject. Thus it may be advantageous to monitor the interaction of the ECG, respiration, and thermal changes in a subject measured in real-time during activity to determine the fatigue state, and/or hydration state of the subject.

Figure 21:
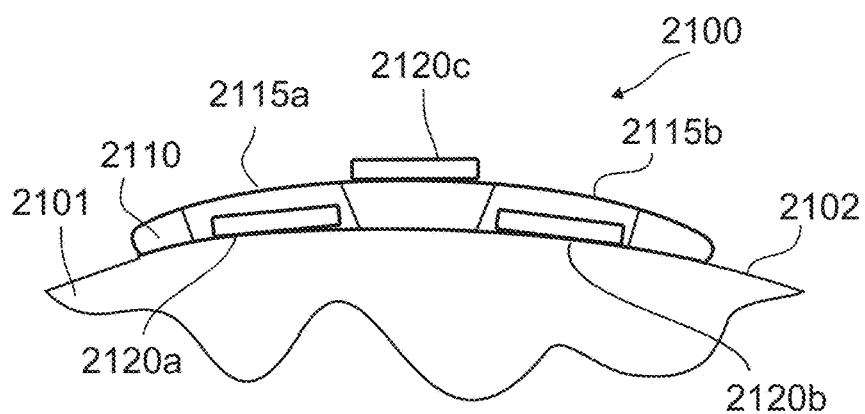
FIG. 21 illustrates a patch sensing device for measuring core temperature, according to an embodiment of the invention.

FIG. 21 shows an example of such a patch 2100 attached to a subject 2101. The patch 2100 includes an adhesive layer or substrate 2110, having regions 2115a and 2115b as shown. The regions 2115a and 2115b may be insulating and thermally conducting regions, respectively. The patch 2100 includes sensors 2120a, 2120b, 2120c. Sensor 2120a is configured to interface with the skin 2102 of the subject 2101 in the insulating region 2115a, while sensor 2120b is configured to interface with the skin 2102 of the subject 2101 in the thermally conducting region 2115b. Sensor 2120c is placed opposite the skin-interfacing side of the patch 2100 and is configured to measure ambient or environmental properties. While FIG. 21 shows an example wherein the patch 2100 includes a single insulating region 2115a and a single thermally conducting region 2115b, embodiments are not limited to this arrangement. A patch or other sensing device may more generally include multiple insulating and/or thermally conducting regions. In addition, while patch 2100 shows the insulating region 2115a and thermally conducting region 2115b on left and right sides of the patch 2100, this is not a requirement. In some cases, an insulating region may surround a thermally conducting region, or vice versa.

A number of use cases for measuring body temperature, physiologic effects of dehydration, and fatigue with a modular physiologic monitoring system including a patch or sensor as described above are presented below. It is to be appreciated, however, that these illustrative use cases are provided by way of example only and that embodiments are not limited solely to these specific use cases.

The patch may be placed on the subject while the subject is exercising in an outdoor environment. Although the environmental conditions and the exertion of the subject may change dramatically during the workout, the system as configured is capable of making core temperature measurements and heat loss measurements with improved precision relative to basic skin temperature measurements.

The patch may be placed on the subject while the subject goes to sleep under covers of a bed. Under the covers, the humidity may increase dramatically during the night, and the thermal gradient may be markedly reduced. A modular physiologic monitoring system including the patch or sensor is capable of tracking the core temperature of the subject with improved precision over basic skin temperature measurements.

The patch may be placed on the subject while the subject goes to the beach on a hot, sunny day. In addition to temperature, thermal gradient and local environmental conditions, the sensors in the patch can measure light-based information, such as exposure to ultraviolet (UV) or infrared (IR). The system can thus track core temperature of the subject and heat loss, as well as light exposure during the trip.

In some embodiments, measurements or data received from sensors in the patch may be used to measure temperature, sweat flux, respiration rate, ECG, respiration depth, acceleration or activity sensing, pulmonary compliance as per congestive heart failure (CHF) protocols, sweat rate, etc.

Temperature may be measured with temperature sensors, and may be associated with one or more of skin under thermal vasodilation, skin ambient temperature, environmental ambient temperature, sweat temperature, etc.

Sweat flux may be a volumetric measure, such as milliliters per minute (mL/min). The patch may be configured with features to facilitate polymer wicking and/or cooling. The volumetric rate of sweat may be correlated with temperature, activity, ambient temperature, etc.

Respiration rate of the subject may be correlated with activity sensors, recorded after activity, etc.

ECG may be measured with one or more hubs/electrodes connected to the patch or patches. ECG may be used to identify HR recovery and activity (HR acceleration) relationships. Rate and variability may also be measured with ECG. The ST segment of the ECG may be correlated with strain.

Respiration depth may be measured via diaphragmatic extension and/or contraction using localized EMG and spatial tracking.

Acceleration and activity sensing may be measured with sensors placed on the body to identify movement of or change in center of mass, appendages (e.g., legs, arms, hands, etc.).

Pulmonary compliance, per CHF protocols, may be used for flow estimation by pressure and gradient. External and handheld sensors, such as calibrated tubes, may be used to measure pressure gradients. Intraoral or intranasal sensors include mouthpiece barometers, tooth or intranasal stent barometers, etc. Measurements from intraoral and/or intranasal sensors may be referenced to ambient pressure on a hub or patch connected elsewhere on the body of the subject. Barometry may be used to measure pressure gradients, such as intranasal versus ambient pressure. Barometry may also or alternatively be used to sense inhalation and/or exhalation force, to make approximate conversions to flow, etc. Inhalation and/or exhalation force may be increased with low pulmonary compliance. Time averages of barometer readings and other sensor readings may be utilized.

Measuring or predicting the sweat rate of a subject may include measuring or estimating core temperature of the subject, skin temperature, breathing (e.g., depth, rate, duty cycle, etc.), subject activity, ECG information, or other physiologic parameters described above. One or more aspects of the environment around the subject may also be measured in conjunction with the physiologic parameters of the subject. Ambient or environmental parameters which may be measured include but are not limited to local temperature, humidity, sun intensity, altitude including changes in altitude (e.g., such as changes occurring during stair or hill climbing, etc.), heat transfer coefficients between the subject and the surroundings of the subject, etc. Heat transfer coefficients may be a key parameter that can take the place of or be representative of various ambient or environmental parameters.

The weight of the subject may be precisely measured at intervals, including but not limited to before and after a workout, before and after defecation, before and after sleep, before and after resting in a controlled climate (e.g., a sauna, a bathtub, etc.), or the like. The weight of the subject may be utilized to estimate or predict sweat rate of the subject.

Relationships between temperature measurements, ambient or environmental measurements, weight measurements, etc. may be correlated with exertion levels and environmental effects. From the determined relationships, which may be collected over one or multiple sessions, types of workouts, climate types, etc., the sweat rate prediction algorithm is generated. The sweat rate prediction algorithm looks to and compares physiologic state, activity state and environmental state with a database to predict a sweating rate of the subject. The sweat rate may be used to predict hydration needs of the subject during current activities to maintain optimal hydration.

A modular physiologic monitoring system for monitoring and management of body temperature and systemic fatigue may include a heating element, a moisture collection element, etc. whereby the sweating response of the subject in the region of the body to which the patch is attached may be determined as it correlated to skin temperature, and to skin temperature versus central mediating aspects such as core temperature, blood salt concentration, etc.

Modular physiologic monitoring systems for monitoring and management of body temperature and systemic fatigue may further include various stimulating devices, which may be used to apply stimulus including multi-modal stimulus to the subject in response to measurements from the sensing device or patch attached to the subject. Such stimulus may be in the form of heating or cooling the subject, triggering alarms or alerts (e.g., visual or audible) upon detecting events such as thresholds for core temperature, sweating rate, etc. where the alarms or alerts are provided directly to the subject, to a caregiver or other individual associated with the subject such as a coach or medical staff, etc.

Figure 22:
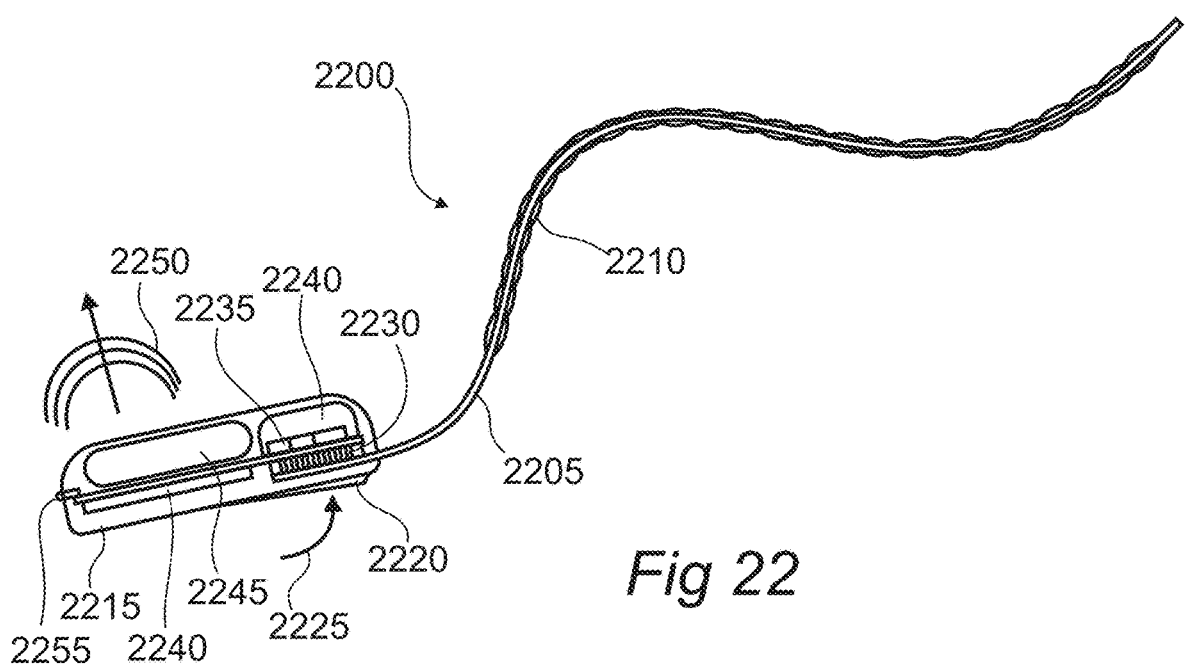
FIG. 22 illustrates a patch with a reusable component for monitoring pressure along a region of a subject, according to an embodiment of the invention.

FIG. 22 shows a patch 2200 with reusable component 2225 for monitoring interfacial pressure along a region of a subject. The patch 2200 includes a plurality of microcells 2210 arranged in a thin, flexible laminate 2205. The patch 2200 may include an adhesive for attachment to the body of a subject. The patch 2200 is attachable to the reusable component 2225 via a connector 2230. The patch 2200 may include a plurality of electrical traces arranged so as to connect the microcells 2210 to the connector 2230. The connector 2230 includes a manifold 2240 to direct a fluid to one or more of the microcells 2210 as well as one or more pressure sensors 2235 to measure local pressure in one or more of the microcells 2210. The reusable component 2225 includes a micropump 2245 for directing fluid flow to/from the microcells 2210 and a power source 2240 such as battery. The reusable component 2225 may also include a vent 2255 to adjust the internal pressure of the reusable component 2225 with the surroundings. The connector 2230 may interface with a locking mechanism 2220 so as to secure the reusable component 2225 to the patch 2200. The reusable component 2225 may include a wireless communication 2250 subsystem, the subsystem configured so as to convey an interfacial pressure reading as monitored by one or more of the microcells 2210 to a host, stimulating device, or the like. Such a system may be advantageous for monitoring a local interfacial pressure in real-time, determining the duration of pressure application to a local region of a subject, determining when pressure application to a region of a subject exceeds a predetermined level or duration, etc.

Figure 23:
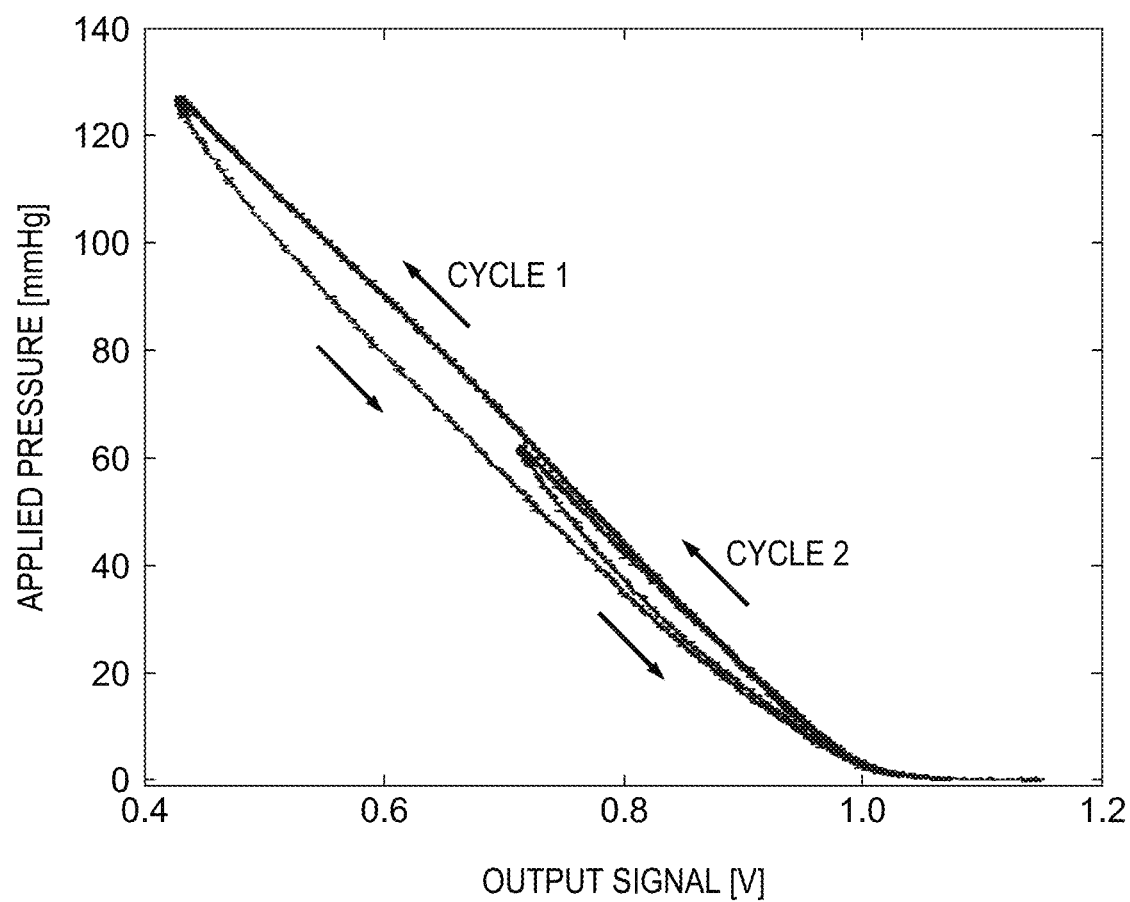
FIG. 23 illustrates a plot of applied pressure, according to an embodiment of the invention.

FIG. 23 shows a plot of output measured by the reusable component 2225 to interfacial pressure application to a microcell 2210 in the patch 2200. The pressure level in the microcell 2210 is substantially linear and with minimal hysteresis so as to precisely determine the pressure applied to the microcell 2210 on the subject. The patch 2200 is provided as a thin, soft laminate with stable microchannels coupling the microcells 2210 to the connector 2230. The patch 2200 may be provided as a substantially thin and stretchable laminate film, the patch 2200 may have a total thickness of less than 100 µm, less than 50 µm, less than 25 µm, or the like.

Figure 24A:
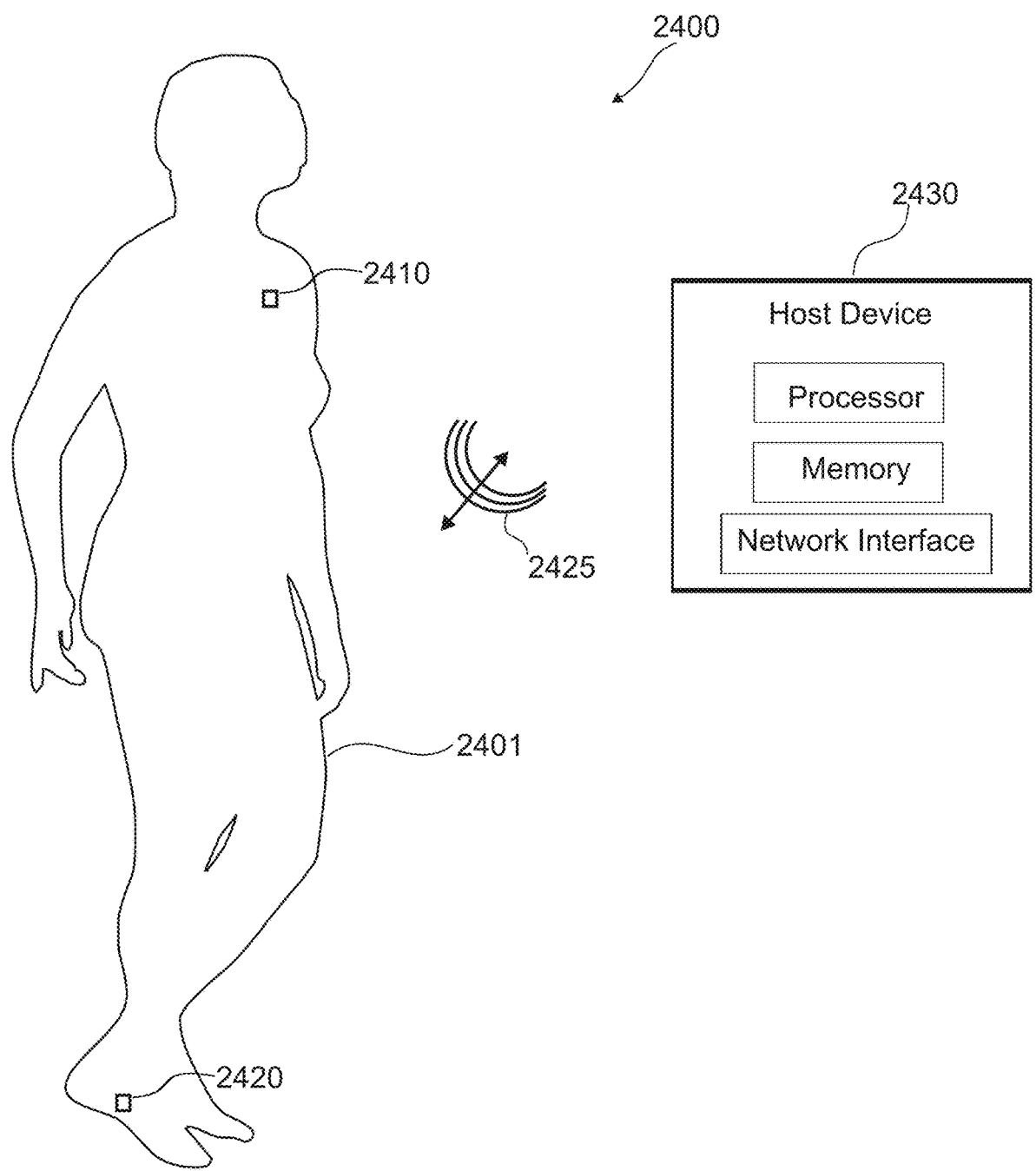
FIGS. 24a-24c illustrates a modular physiologic monitoring system, according to an embodiment of the invention.
Figure 24B:
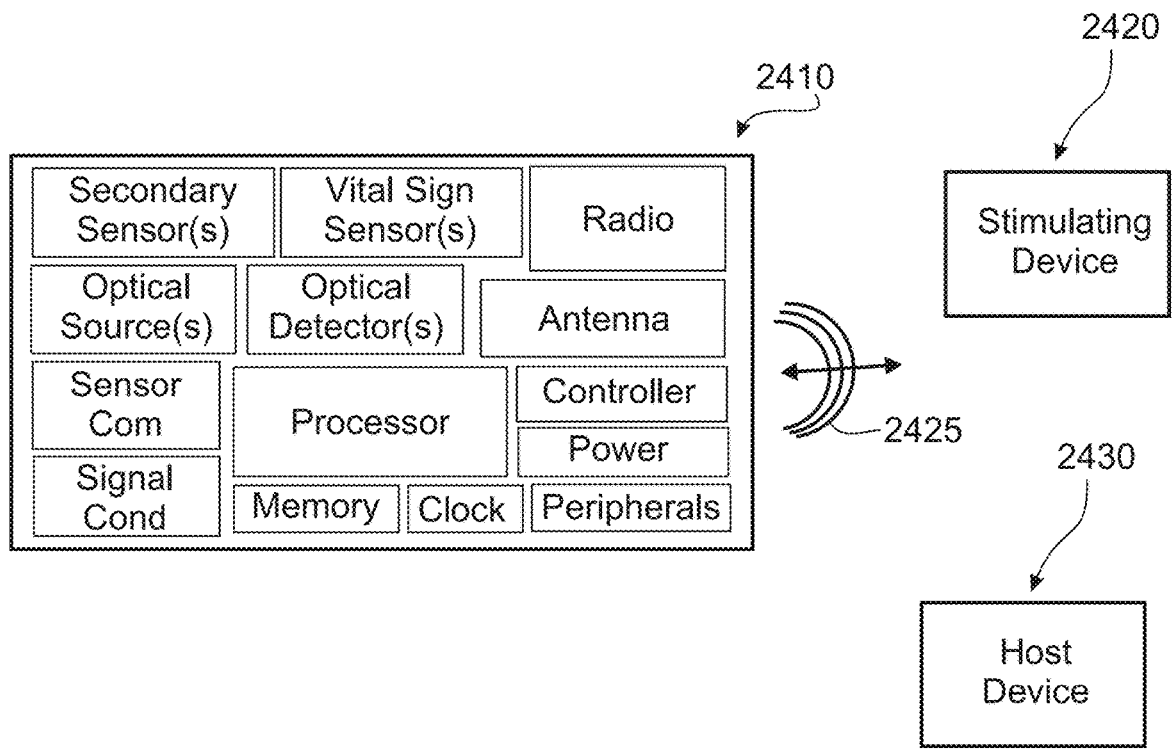
Figure 24C:
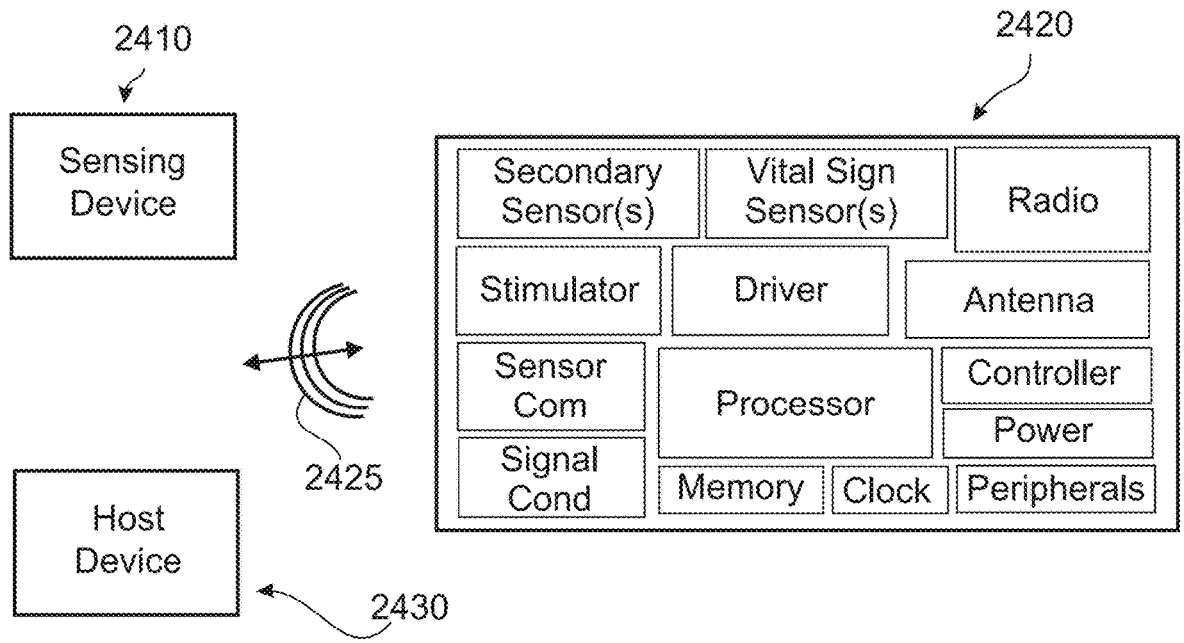

FIGS. 24a-24c shows a modular physiologic monitoring system 2400. The modular physiologic monitoring system 2400 includes a sensing device 2410 and a stimulating device 2420 attached to a subject 2401 that are in wireless communication 2425 with a host device 2430. The host device 2430 includes a process, a memory and a network interface.

The processor may comprise a microprocessor, a microcontroller, an application-specific integrated circuit (ASIC), a field-programmable gate array (FPGA) or other type of processing circuitry, as well as portions or combinations of such circuitry elements.

The memory may comprise random access memory (RAM), read-only memory (ROM) or other types of memory, in any combination. The memory and other memories disclosed herein may be viewed as examples of what are more generally referred to as "processor-readable storage media" storing executable computer program code or other types of software programs. Articles of manufacture comprising such processor-readable storage media are considered embodiments of the invention. A given such article of manufacture may comprise, for example, a storage device such as a storage disk, a storage array or an integrated circuit containing memory. The processor may load the computer program code from the memory and execute the code to provide the functionalities of the host device 2430.

The network interface provides circuitry enabling wireless communication between the host device 2430, the sensing device 2410 and the stimulating device 2420.

FIG. 24a illustrates a modular physiologic monitoring system 2400 that includes only a single instance of the sensing device 2410 and the stimulating device 2420 for clarity. It is to be appreciated, however, that modular physiologic monitoring system 2400 may include multiple sensing devices and/or multiple stimulating devices. In addition, although FIG. 24a illustrates a modular physiologic monitoring system 2400 in which the sensing device 2410 and the stimulating device 2420 are attached to the subject 2401, embodiments are not limited to such arrangements. As described above, one or more sensing and/or stimulating devices may be part of contacting surfaces or non-contacting devices. In addition, the placement of sensing device 2410 and stimulating device 2420 on the subject 2401 may vary as described above. Also, the host device 2430 may be worn by the subject 2401, such as being incorporated into a smartwatch or other wearable computing device. The functionality provided by host device 2430 may also be provided, in some embodiments, by one or more of the sensing device 2410 and the stimulating device 2420.

FIG. 24b shows a schematic of aspects of the sensing device 2410 in modular physiologic monitoring system 2400. The sensing device 2410 includes one or more of a processor, a memory device, a controller, a power supply, a power management and/or energy harvesting circuit, one or more peripherals, a clock, an antenna, a radio, a signal conditioning circuit, optical source(s), optical detector(s), a sensor communication circuit, vital sign sensor(s), and secondary sensor(s). The sensing device 2410 is configured for wireless communication 2425 with the stimulating device 2420 and host device 2430.

FIG. 24c shows a schematic of aspects of the stimulating device 2420 in modular physiologic monitoring system 2400. The stimulating device 2420 includes one or more of a processor, a memory device, a controller, a power supply, a power management and/or energy harvesting circuit, one or more peripherals, a clock, an antenna, a radio, a signal conditioning circuit, a driver, a stimulator, vital sign sensor(s), and secondary sensor(s). The stimulating device 2420 is configured for wireless communication 2425 with the sensing device 2410 and host device 2430.

Figure 25:
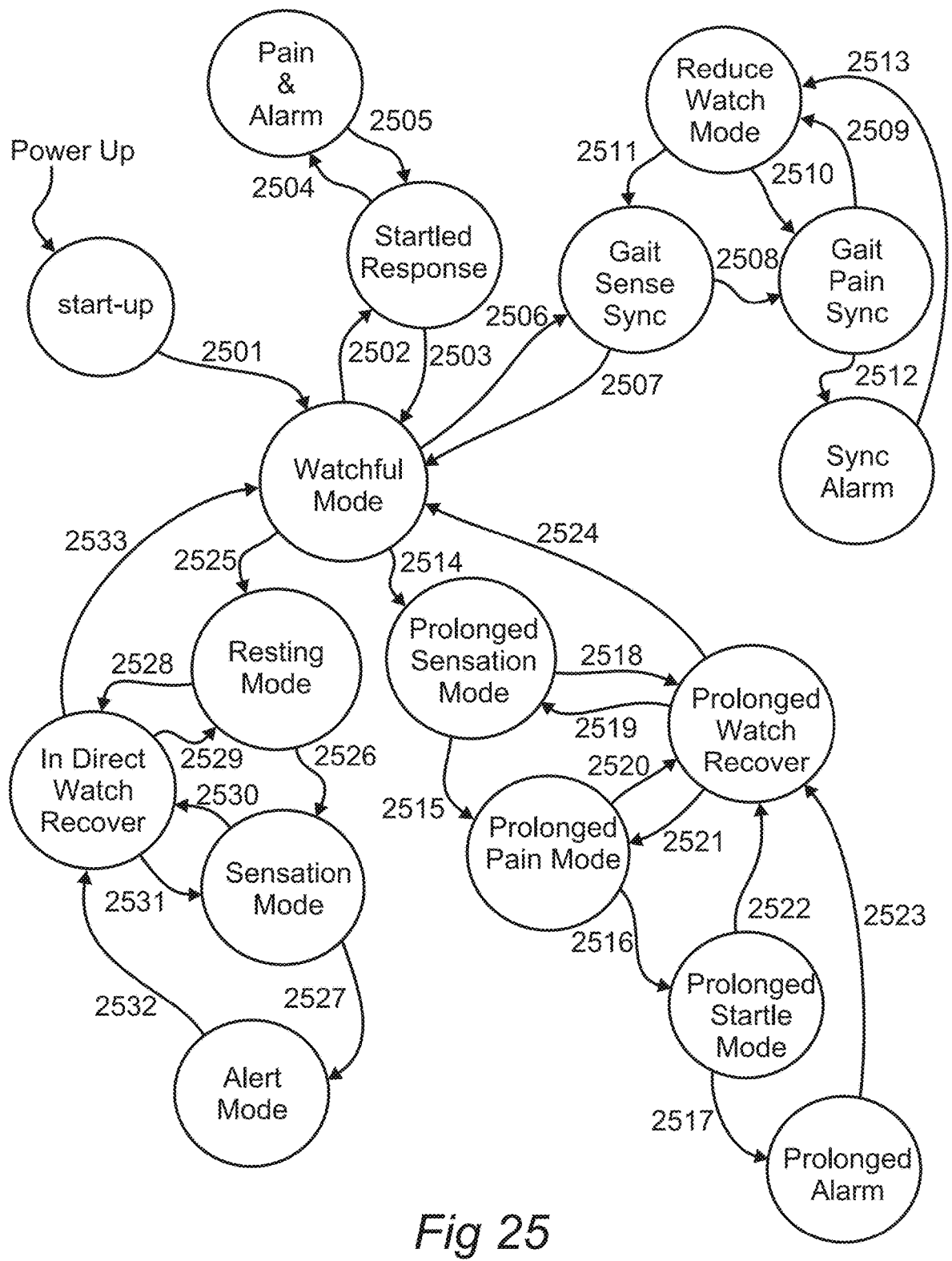
FIG. 25 illustrates a state diagram for monitoring a subject, according to an embodiment of the invention.

FIG. 25 illustrates a state diagram for monitoring the interfacial pressure of a region of a subject during use. The state diagram illustrates a non-limiting methodology for abstracting the movement state of the subject and the corresponding state of the region of interest. The methodology may be used to translate a touch and/or pain sensation from the region of interest of the subject to another region of the subject (e.g., a region of the subject with functioning neural receptors). In one non-limiting example, such a system may be used to transfer touch and pain related information from a region of a subject suffering from peripheral neuropathy to a region of a subject that is unaffected by the condition. In such a scenario, the information gathered may be used to make the user aware of unexpected impacts to the affected region, touch sensation on the region, prolonged pressure application to the region (e.g., making that region vulnerable to pressure ulcer formation), to assist with gait, to assist with correcting and/or relearning gait in a physiotherapy setting, etc.

The system starts in a watchful mode after transitioning 2501 from a start-up mode after power up. The system transitions to one or more states depending on the inputs monitored by the system. The system may transition 2502, 2506, 2514, 2525 to an abstracted state relating to the state of the subject, such as: a startled response mode (e.g., wherein an impact is registered on a region of interest) via transition 2502; a gait sense sync mode wherein gait sensing is detected (e.g., walking related movement) via transition 2506; a prolonged sensation mode (e.g., wherein substantially steady pressure is applied to the region of interest) via transition 2514; and a resting mode (e.g., wherein the subject or the region of interest thereof is not moving or has movement below a specified threshold) via transition 2525.

In the startled response mode, the system may transition 2504 to a pain and alarm mode on determining that applied pressure exceeds a threshold. The system transitions 2505 back to the startled response mode and then transitions 2503 back to the watchful mode on determining that the applied pressure reaches a normal level, after a specified time following impact to the region of interest, etc.

In the gait sense sync mode, the movement of the subject and periodic pressure application to the monitored region are collectively used to time a stimulus response to the subject via a corresponding stimulating device. During movement associated with the gait, the system may monitor for pressure levels on the monitored region that may exceed pain thresholds, whereby if such an occurrence happens, the system may transition 2508 into a gait pain sync mode, whereby the stimulus amplitude, duration, or type of nerves elicited (e.g., altering the stimulus protocol so as to activate pain fibers at the stimulating device site), is altered to signify a pain response to the subject. In the case that an impact or exceedingly high pressure is applied to the monitored region, the system may transition 2512 into a sync alarm mode to provide an aggressive stimulus to the subject to prompt immediate response to an excessive pressure application or impact to the monitored region. From the gait pain sync mode and the sync alarm mode, the system may transition 2509, 2513 to a reduce watch mode after remediation. From the reduce watch mode, the system may transition 2510 back to the gait pain sync mode if the pressure levels on the monitored region again exceed pain thresholds, or transition 2511 back to the gait sense sync mode and from the gait sense sync mode transition 2507 back to the watchful mode after a specified time, after determining that the subject is no longer in a walking mode or other gait sensing activity, etc.

In the prolonged sensation mode, the system may transition 2515 to a prolonged pain mode if an applied pressure to the region of interest exceeds a threshold, indicating that the applied pressure should be eliciting a pain response from the monitored region (e.g., if the neural functionality in the affected region was normal, the subject would have registered pain in the monitored region). The system may transition to a prolonged watch recover mode (e.g., via a direct transition 2518 from the prolonged sensation mode or via a transition 2520 from the prolonged pain mode) when pressure application is sufficiently low. The system may transition 2516 to a prolonged startle mode, wherein a corresponding stimulating device may begin stimulating the subject so as to prompt the subject to move or otherwise to adjust pressure on the monitored region. If the subject does not respond, the system may transition 2517 to an alarm state, activating one or more alerts to more aggressively prompt the user to alleviate pressure from the monitored region. In a hospital or other managed care setting, alerts may be provided to a caregiver so as to prompt the caregiver to take action if the pressure application to the affected area has exceeded a safe threshold for a prolonged period of time. The system may transition 2522 or 2523 from the prolonged startle mode or alter mode, respectively, following remediation (e.g., adjusting the pressure on the monitored region). The system may transition 2521 from the prolonged watch recover mode to the prolonged pain mode following determination that the applied pressure has exceeded the threshold. The system may transition 2519 back to the prolonged sensation mode or transition 2524 back to the watchful mode from the prolonged watch recover mode after a specified time, after determining that the applied pressure reaches a normal state, etc.

In the resting mode, the system may transition 2526 to a sensation detection mode if pressure application is detected on the region of interest or transition 2528 to an indirect watch mode if movement has stopped for a prolonged period of time. In either case, the system may transition to an alert mode if a time/pressure metric has been exceeded (e.g., a direct transition 2527 from the sensation mode or a transition 2531 to the sensation mode from the indirect watch recover mode followed by the transition 2527 from the sensation mode to the alert mode). Transitions 2532, 2530, 2529 and 2533 may be used to return to the indirect watch recover mode, resting mode and/or watchful mode if pressure is removed or movement is restored within an allotted timeframe.

Figure 26:
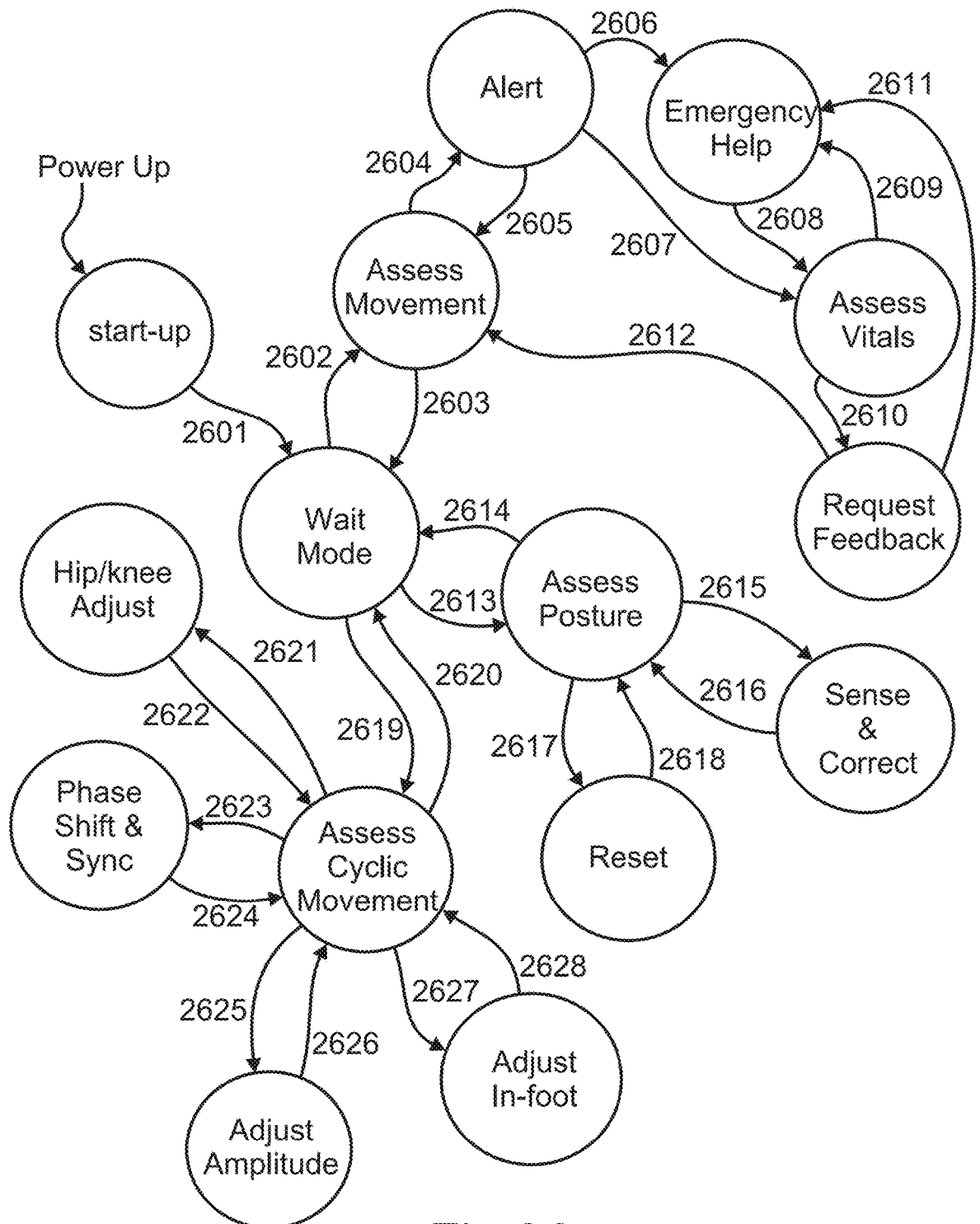
FIG. 26 illustrates a state diagram for monitoring a subject, according to an embodiment of the invention.

FIG. 26 illustrates a state diagram for monitoring the posture and vitals of a subject during a usage procedure. On power up, the system enters a start-up mode and then transitions 2601 to a wait mode, where the system generally waits for the user to enter a state such as a movement state, a change in posture, a cyclic movement state, etc.

In response to detecting defined types of movement of the subject or a region of interest thereof, the system transitions 2602 to an assess movement mode. In the movement assessment mode, the system monitors the movement of the subject to look for certain types of movement events, such as unusually wandering, periodic movements, a fall, etc. If a dangerous movement is detected, the system may enter the request feedback mode (e.g., via transitions 2604/2606/2608/2610 or via transitions 2604/2607/2610) and/or the assess vitals mode (e.g., via transitions 2604/2607 or 2604/2606/2608). Although not explicitly shown in FIG. 26, there may also be direct transitions from the assess movement mode to the request feedback mode and the assess vitals mode, which do not pass through the alert, emergency help and/or assess vitals modes. In the feedback mode, the system may prompt the subject or a caregiver for feedback, such as via a microphone embedded in one or more sensing devices. In the assess user vitals mode, the system may utilize one or more of the sensing devices to assess one or more physiologic parameters of the subject. If the subject is in a fallen state or other undesired state but the vital signs are substantially normal, the system may transition to alert mode wherein one or more stimulating devices provide stimulus alerting the subject to correct the undesired state. If the subject is in the undesired state and the vital signs are dangerous or otherwise not normal, the system may transition to the emergency help state whereby outside help is contacted. In the emergency help state, the system may communicate the location of the subject (e.g., via location information provided by a location service or via location information obtained from one or more of the sensing devices), the posture of the subject, vital sign information, etc. so as to assist a caregiver or emergency personnel. Various transitions 2604 through 2611 may be used to move between the assess movement mode, alert mode, emergency help mode, assess vitals mode and request feedback mode as illustrated in FIG. 26. As indicated above, however, the system may also include direct transitions between certain modes, such as a direct transition from the assess movement mode to the request feedback mode or from the assess movement mode directly to the assess vitals mode, etc. which are not shown for clarity of illustration.

In response to detecting a change in posture, the system transitions 2613 to the assess posture state. The state of the posture of the subject is then monitored and, if the subject's posture is outside predetermined bounds, the system may transition 2615/2616 to/from a sense and correct mode where one or more stimulating devices are activated to send a stimulus to the subject so as to correct the posture of the subject. The system may alternatively transition 2617/2618 to/from a reset mode, wherein one or more stimulating devices provide stimulus to cause the subject to reset his or her posture, or wherein one or more sensing devices are configured to re-determine a posture of the subject. On remediating postural issues, the system may transition 2614 back to the wait mode.

In response to detecting cyclic movement seen on a subject, the system transitions 2619 to an assess cyclic movement mode. Based on assessment of the cyclic movement, the system may: transition 2621/2622 to/from a hip or knee adjust mode; transition 2623/2624 to/from a phase shift and sync mode; transition 2625/2626 to/from an adjust amplitude mode; or transition 2627/2628 to/from an adjust in-foot mode. In the hip or knee adjust mode, phase shift and sync mode, adjust amplitude mode and adjust in-foot mode one or more corresponding stimulating devices apply stimulus to the subject, such as stimulus to direct the subject to make changes to their gait or other cyclic movement. If cyclic movement is no longer detected, the system may transition 2620 back to the wait mode.

Figure 27:
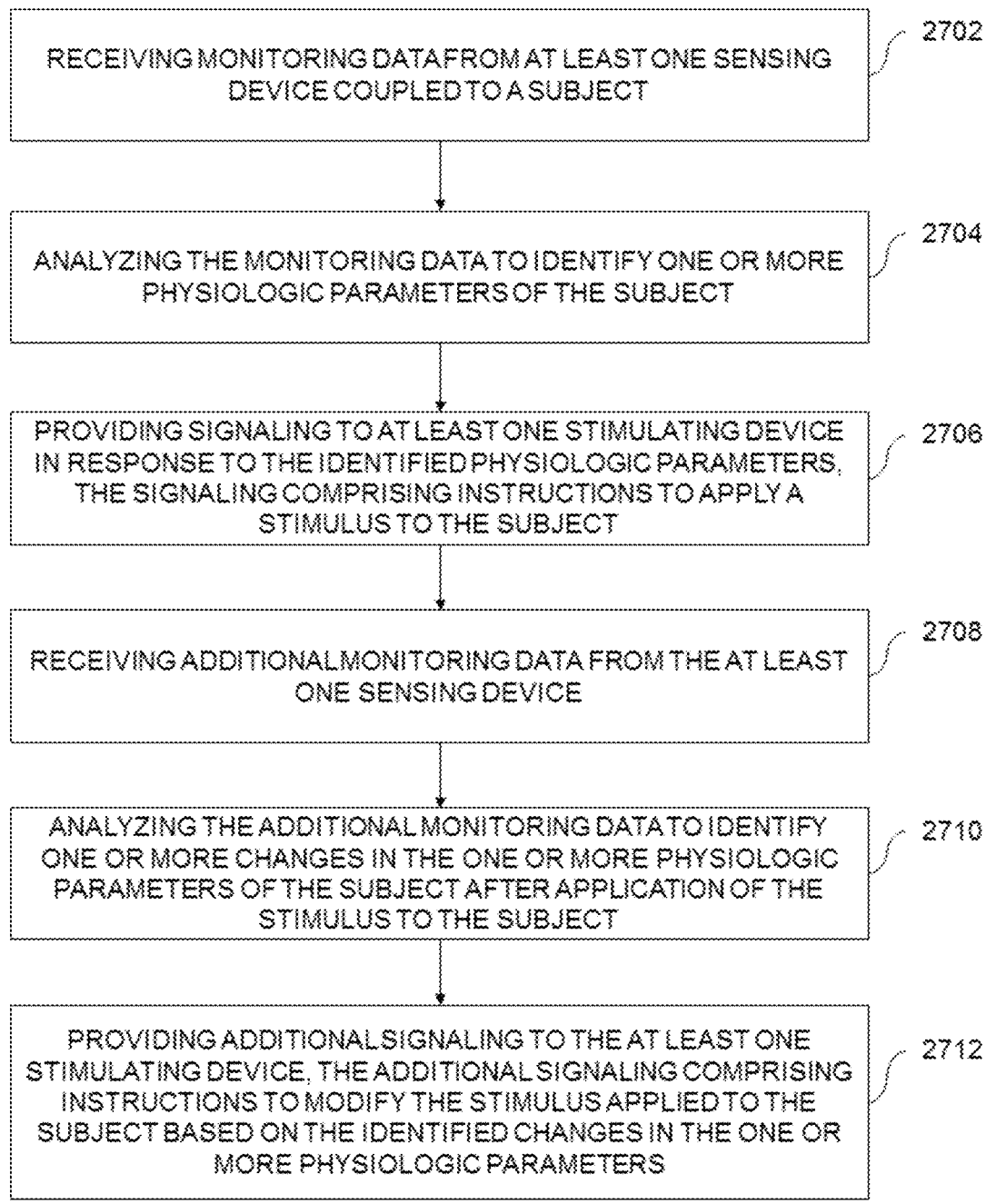
FIG. 27 illustrates a method for monitoring and management of physiologic parameters of a subject, according to an embodiment of the invention.

FIG. 27 illustrates a method which may be performed utilizing a modular physiologic monitoring system as described herein. The method illustrated in FIG. 27 may be considered a method from the perspective of a host device in a modular physiologic monitoring system. It is to be appreciated, however, that the host device may be implemented at least in part utilizing one or more sensing and/or stimulating devices of a modular physiologic monitoring system as described elsewhere herein.

The method begins with step 2702, receiving monitoring data from at least one sensing device coupled to a subject. In step 2704, the monitoring data is analyzed to identify one or more physiologic parameters of the subject. Signaling is provided to at least one stimulating device in response to the identified physiologic parameters in step 2706. The signaling comprises instructions to apply a stimulus to the subject.

The method continues with step 2708, receiving additional monitoring data form the at least one sensing device, such as additional monitoring data after application of the stimulus to the subject. The additional monitoring data is analyzed in step 2710 to identify one or more changes in the one or more physiologic parameters of the subject after application of the stimulus to the subject. In step 2712, additional signaling is provided to the at least one stimulating device. The additional signaling comprises instructions to modify the stimulus applied to the subject based on the identified changes in the one or more physiologic parameters. Modifying the stimulus may include ending application of the stimulus, adjusting a frequency, amplitude or strength of the stimulus, changing the type of stimulus applied to the subject, etc.

Modular physiologic monitoring systems described herein can monitor and save or store various types of data, including data relating to a wide variety of physiological parameters of a subject. The particular parameters which are measured may vary depending on the configuration and/or placement of the one or more sensing devices. The one or more sensing devices may include various types of sensors, including but not limited to sensors for measuring EEG, EOG, EMG of various muscle groups, audible inputs (e.g., internal body sounds from down facing microphones, external audible sounds from outfacing microphones), kinematics including orientations, movements, movements associated with respiration, respiration efforts, etc. In addition, one or more sensing devices may be configured to monitor local tissue stretch, which can be used as an independent respiratory monitor, respiratory depth monitor, etc. Based on placement of the one or more sensing devices, electrophysiological signals may be monitored at any desired location. Such electrophysiological signals include but are not limited to basic myography (e.g., ECG, EMG, neuro, etc.) along with the sudomotor, neural receptor field, and vasomotor additions. Described below are various examples of data which may be obtained using one or more sensing devices during a monitoring session. Unless otherwise noted, the data described below and shown in the accompanying figures represents raw data. As described elsewhere herein, the sensing devices and/or the host device may be configured to format or combine multiple types of raw data to establish relevant information associated with a particular event, such as an apneic event.

During testing, sensing devices may monitor one or more of the following outputs: ECG (with any desired lead configuration); EMG (with any desired lead configuration); sudomotor function (anywhere, including glabrous or non-glabrous tissues); vasomotor function (anywhere, including glabrous or non-glabrous tissues); receptor field measurements (such as using multi-electrode patches and chips); optical measurements; blood pressure trends; cardiac index; cardiac output; oxygen delivery; indexed oxygen delivery; maximum pressure slope during systole; finger arterial blood pressure waveform; hydrostatic compensation reference system (good for tilt testing, posture changes, etc.); inter beat interval; stroke volume; stroke volume index; systemic vascular resistance; systemic vascular resistance index; stroke volume variation; plethysmogram; non-invasive arterial oxygen saturation; perfusion index; pulse pressure variation; total hemoglobin; etc.

Captured physiologic data, including data relating to BP and ECG may be further analyzed to capture various parameters. For BP analysis, parameters such as systolic pressure, diastolic pressure, dicrotic notch timing and pressure, mean pressure, pulse pressure, ejection duration, non-ejection duration, cycle duration or HR from BP, time to peak, mean diastolic pressure, etc. may be assessed. Cycle-to-cycle waveforms may also be analyzed, such as comparing waveforms at different times in a test, etc. Dynamic metrics may also be generated from temporal curves. For ECG analysis, parameters such as R-R interval(s), heart rate (BPM), PR interval(s), P duration(s), QRS interval(s), QT interval(s), QTc(s), JT interval(s), Tpeak Tend interval(s), P amplitude (in millivolts (mV)), Q amplitude (in mV), R amplitude (in mV), S amplitude (in mV), ST height (in mV), T amplitude (in mV), etc. Higher frequency analysis may also be performed, such as extracting EMG baselines, which may be useful as certain electrodes that are not close to contracted muscles may show a significant change in higher frequency content which may be related to sympathetic nerve activity (SNA).

Various sensing devices of a modular physiologic monitoring system may measure various parameters of a subject to monitor for various conditions, such as sleep apneic events as described herein. The particular physiologic parameters or other metrics that are measured using the sensing devices may be selected based on the number and/or type of sensing devices available, for comfort of the subject, based on which autonomic changes are most relevant for detecting a particular event, etc.

In some embodiments, sensing devices in a modular physiologic monitoring system may provide raw data, or data which includes only basic filtering, to a host device. Further filtering may be performed, with feature extraction algorithms to pull out information from the raw data associated with the state and actions of the subject. The filtering may be performed by the sensing devices in a modular physiologic monitoring system, or by a host device or one or more stimulating devices in the modular physiologic monitoring system configured for communication with the sensing devices. In some embodiments, it is desired to offload filtering, feature extraction and other processing to the host device so as to reduce a processing burden on the sensing devices, which may increase the battery life of the sensing and/or stimulating devices, decrease the cost associated with the sensing and/or stimulating devices by not requiring powerful or sophisticated processing and/or memory components, etc.

Signals associated with physiologic parameters of a subject may be collected in real time, combined and analyzed as part of a multiple input multiple output (MIMO) modular physiologic monitoring system to determine the state of the subject (e.g., utilizing one or more sensing devices), identify if an event is happening and the event type (e.g., utilizing a host device, the one or more sensing devices and/or one or more stimulating devices) and then provide a stimulus to the subject (e.g., utilizing one or more stimulating devices).

In some embodiments, a modular physiologic monitoring system may be configured to remotely communicate the health status of a subject. The system can provide multi-modal measurement of physiologic parameters such as HR, skin temperature, respiration, clinical ECG, thermal gradients for core temperature predictions, movement, posture, etc. The system may utilize one or more patches and/or patch-module pairs. The patches are ultra-wearable, including hypoallergenic and stretchable microelectronic components and bioadhesives. Such patches and/or patch-module pairs are configured to remotely monitor and transmit health data from a subject to a command post, such as a host device, over the duration of a mission or wear period.

A modular physiologic monitoring system may be designed for use in high stress applications, and is configured to continue operation under various conditions including high sweat, dynamic movement, during showering, and the like. The modular physiologic monitoring system can also be built to be skin safe, breathable and incredibly comfortable for the subject. Such comfort is provided, in some embodiments, through the use of thin and stretchable patches that act as an extension of the skin, and as such a subject does not substantially feel that the patch or patch-module pair is being worn. The patch or patch-module pair is lightweight and does not cause skin irritation. Skin safety is provided, in some embodiments, by the design of the patches and/or patch-module pairs for chronic wear with all adhesive components being hypoallergenic, breathable (e.g., with minimal maceration risks) and stretchable, so as to limit pull on attached tissues during dynamic usage scenarios. Sensors included in the patches and/or patch-module pairs are design such that they can be placed on the subject without requiring the subject to remove clothing.

Communication of data from the patches and/or patch-module pairs may be performed via a local personal communication device (PCD). Such communication in some embodiments takes place in two parts: (1) local communication between a patch and/or patch-module pair (e.g., via a hub or module of a patch-module pair) and the PCD; and (2) remote communication from the PCD to a back-end server. The PCD and back-end server may collectively provide functionality of the host device as described elsewhere herein.

In some embodiments, the modular physiologic monitoring system utilizes one or more patch-module pairs. The patch, as described elsewhere herein, may provide a disposable subject interface. The module or hub, as described elsewhere herein, may provide a reusable hardware component. The hub may have a diameter of approximately 20 mm at its longest width, with a thickness of approximately 5.5 mm at its thickest point. The hub may weigh approximately 2.1 grams. The hub is hermetically sealed, rechargeable, and has a life expectancy in service of at least one year. The patch is disposable, breathable and tailored to wear times ranging from 1 day to 1 week. The wear times may be based on usage scenarios, climate, etc. The system may be built to accommodate a range of usage cases, including showering, hot environments, extreme sweating, etc.

To apply a patch-module pair, the subject can peel a liner off of an adhesive portion of the patch, and adhere the patch firmly to the skin at a desired measurement site (e.g., a sternum for ECG). The attachment process is analogous to that of attaching a small bandage. The subject then attaches the hub/module to the patch to start recording and wireless data transfer. Necessary or desired metrics representing the health of the subject are generated locally. System accuracy may vary based on the usage case and attachment location.

The patch in some embodiments is designed to be soft and stretchable, such that the subject generally does not feel that the patch is being worn. The patch moves intimately with the skin of the subject without appreciably pulling on the skin during use. In some embodiments, electrodes on the patch are configured to locally hydrate the adjacent tissues to quickly lower epidermal impedance. Fluid balance at the electrodes may be maintained through vapor transfer through the electrode films.

Skin-electrode interfaces and interconnects are isolated from surroundings via hydrophobic bioadhesives and hydrophobic films in the patches. Thus, the patches will not succumb to water breach in usage scenarios such as showering, extreme humidity, rain, water soaked clothing, etc.

Movement artifacts are dramatically reduced by the soft mechanical nature of the stretchable interconnects and the minimal relative movement between the hub/module hardware and the adjacent tissues. Furthermore, strategic placement of the patch-module pairs away from large muscles helps to passively reduce EMG artifacts. In one usage scenario, patch-module pairs may be placed on the upper torso near the sternum to help reduce EMG related artifacts.

Preamplifiers are located immediately at measurement sites, and with minimal relative movement therebetween. Current pathways are also locally balanced. There is no or very limited movement between the patch-module pair and the skin of the subject, thus eliminating or reducing lead movement artifacts.

Hubs/modules are tough, hermetically sealed and attached to an accompanying patch via a combination of magnetic interconnects and an adhesive gasket. The gasket provides a hermetic seal around the interconnects and has a high peel strength, while the magnetic interconnects maintain secure electrical contact between the hub/module and patch during use. The attachment between the patch and the hub/module can be tailored to balance removal of the hub/module for hot-swapping and reuse and secure holding during dynamic movement of the subject. In some embodiments, the hub/module attaches securely to the patch with a holding force of greater than 0.5 kilogram-force (kgf), greater than 1 kgf, greater than 2 kgf, greater than 3 kgf, or the like.

Figure 28:
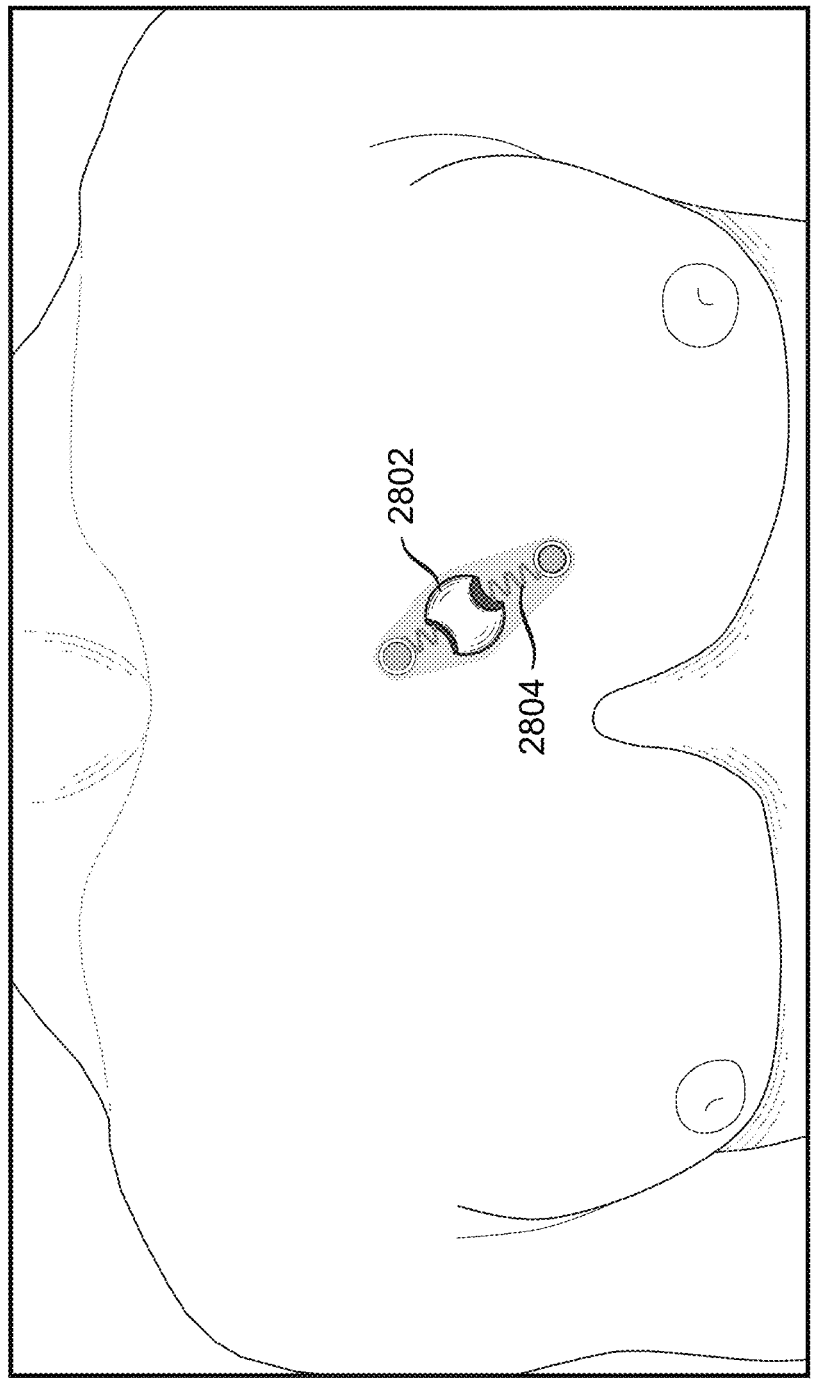
FIG. 28 illustrates a patch-module pair attached to the skin of a subject, according to an embodiment of the invention.
Figure 29A:
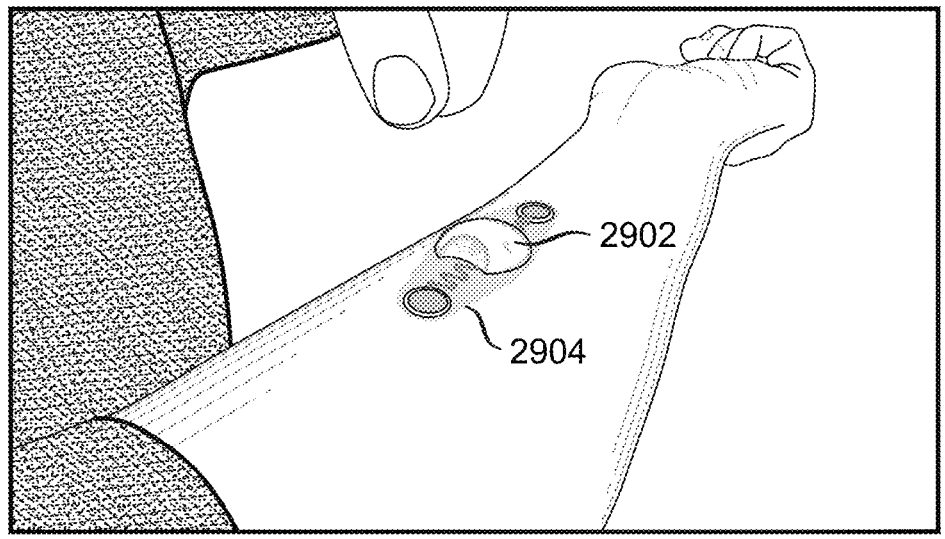
FIGS. 29a and 29b illustrate holding force of a patch-module pair attached to the skin of a subject, according to an embodiment of the invention.
Figure 29B:
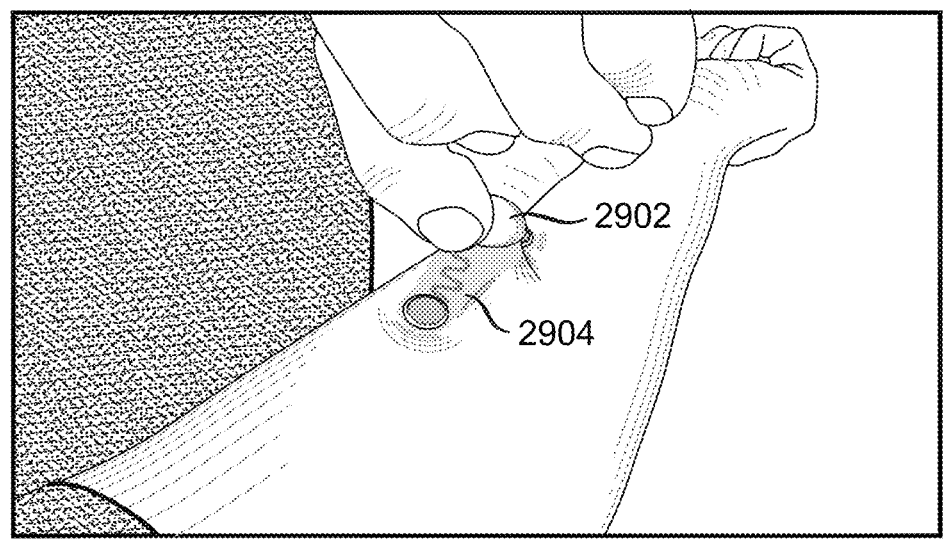

FIG. 28 illustrates a patch-module pair attached to the skin of a subject, including a hub/module 2802 and a patch 2804. The hub/module 2802 provides a wearable unit, and the patch 2804 provides an ultra-breathable and wearable skin interface. FIG. 28 illustrates the patch-module pair attached to a torso of a subject. Demonstration of the holding force is illustrated via a patch-module pair including hub 2902 and patch 2904 attached to the forearm of a subject in FIGS. 29a and 29b.

When placed on the torso, patch-module pairs may collect a diagnostic grade ECG of the subject during use. By collecting the full ECG, a signal quality metric may be created along with a confidence interval relating to the quality of the captured signal. In addition to the ECG, further physiologic information associated with the subject's health state may be collected by the hub/module in the form of secondary sensor readings. This provides significant advantages to conventional techniques, which may only record an average R-R interval as an estimate of heart rate (e.g., conventional arrangements may only generally estimate the R-R interval via a hardware comparator or via peak analysis on an SpO2 reading, and thus the entire ECG is not available for further analysis). Such an approach may be advantageous to provide a confidence interval around an ECG generated metric, such as heart-rate. Such a confidence interval may be used to determine if the data collected is of suitable quality so as to trust it (e.g., so as to confirm it is actually related to the R-R interval of the ECG of the subject, and not due to a movement artifact, respiration, EMI, etc.).

Figure 30:
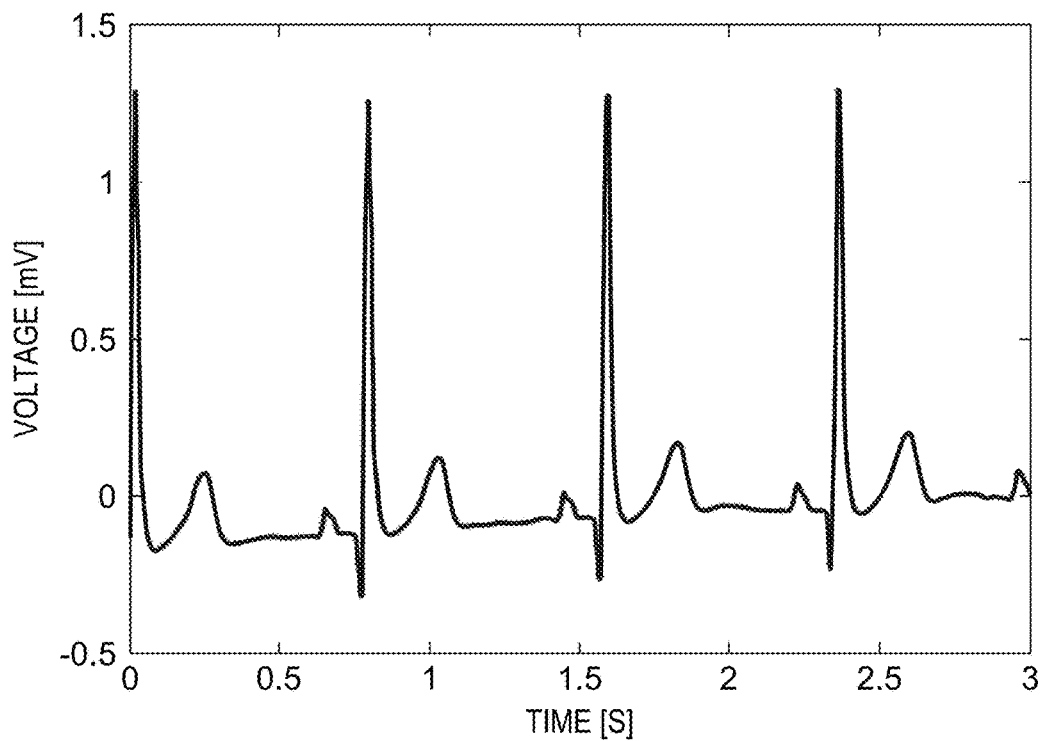
FIGS. 30 and 31 illustrate raw data obtained from a patch-module pair, according to an embodiment of the invention.
Figure 31:
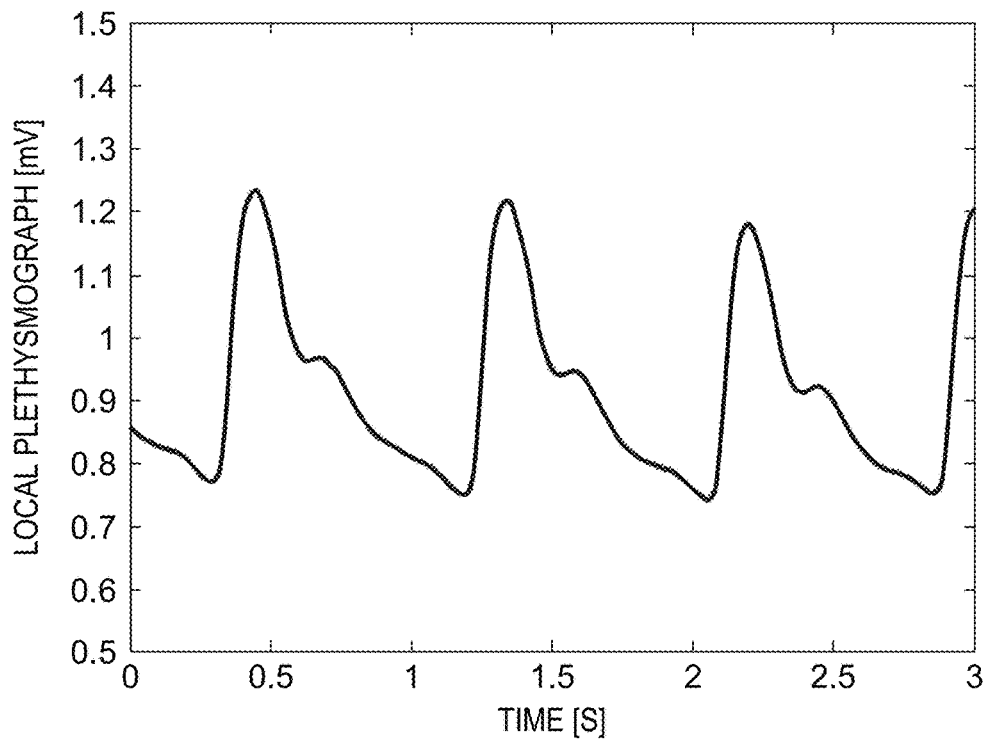

FIGS. 30 and 31 show examples of raw data associated with collected physiologic signals using a patch-module pair. The raw data was taken from a stationary subject, and show initial tracings. FIG. 30 shows a recorded ECG, and FIG. 31 shows a PPG tracing. The PPG in this example is used as a secondary sensing modality. In the context of PPG, the patch-module pairs allow for controlled force application to adjacent tissues and minimization or relative movement, which often plagues PPG readings using conventional techniques. Thus, illustrative embodiments provide for more consistent PPG recordings relative to conventional arrangements.

In addition to measuring electrophysiologic signals, a patch-module pair may be configured to obtain various temperature-related measurements. The hub/module, for example, may include several temperature sensors. One sensor, which may be locally insulated from the environment by the hub/module, may be positioned to monitor temperature directly at the skin of the subject. Another sensor, locally insulated from the skin by the hub/module, may be positioned to monitor temperature at the top of the hub/module. Additional sensors may be placed throughout the hub/module to assist with calibration, heat flux calculations and the like. By measuring temperature at multiple strategic sites, a better estimate of core temperature of the subject may be generated, along with thermal gradients, ambient temperature and humidity changes, etc. A modular physiologic monitoring system may thus be configured to generate improved predictions of core temperature, and provide a confidence metric on core temperature readings during normal usage scenarios. Additional details regarding patches, hubs/modules and patch-module pairs configured for such measurements of core temperature are discussed above.

In some embodiments, a wide variety of types of secondary sensors may be used in a hub/module, including but not limited to temperature sensors for measuring body temperature, ambient temperature, thermal gradients, local humidity, etc., top and/or down facing microphones, dead reckoning kinematic sensing to back up physiologic measurements and improve robustness (e.g., allowing for postural assessment, movement assessment, secondary breathing assessment, etc.). Further positional data and near-field locational data may be obtained from the patch in a patch-module pair.

A communication profile which may be used in a modular physiologic monitoring system will now be described, wherein a PCD performs host functions a hub/module acts as a peripheral. A wireless communication link between the hub/module and the PCD may be established over one or more networks, such as an encrypted 2.4 GHz Bluetooth low energy (BLE) connection. The hub/module and the PCD may initially pair using BLE 4.2 LE secure connections feature, which includes Federal Information Processing Standards (FIPS)-approved Advanced Encryption Standard (AES) Cipherbased Message Authentication Code (CMAC), or AES-CMAS and P-256 elliptic curve Diffie-Hellman (ECDH) algorithms on the BLE physical transport layer. The link between the hub/module and the PCD may be encrypted using security mode 4, link level encored security with encrypted key exchange, and secure simple pairing with short and long term 128-bit keys. The particular pairing method used may vary as desired. In some embodiments, numeric comparison, passkey entry or out-of-band (OOB) pairing methods may be used. The pairing will generally include exchanging of security initialization messages, creation of link keys and enabling encryption. Local keys may be stored in encrypted form in ferroelectric memory to increase the level of security.

The PCD provides a simple user interface to display global positioning system (GPS) data or other location data, health data, to receive local push notifications relating to debugging (e.g., lost links, low confidence metrics, etc.), physiologic state warnings, etc. If the communication link is lost, health metrics, confidence metrics and timestamps can be stored in local memory on hubs/modules until such time as the link with the PCD can be reestablished. Link loss may be handled by a BLE link loss service (LLS). Data itself may be transmitted through different profiles, such as a BLE health device profile (HDP) and/or a BLE message access profile MAP). The HDP approach allows for communication of information directly to the PCD, which can allow for sending more information and for offloading computational burden to the PCD, and gives more robust data storage. The MAP approach allows the hub/module to directly take advantage of the messaging capability of the PCD to efficiently send health and confidence data in the form of messages through to a remote network or remote network server without overly burdening the PCD (e.g., to conserve power or battery for a PCD implemented using a mobile device such as a smartphone, smartwatch, wearable, etc.). In some embodiments, both HDP and MAP approaches are utilized.

Figure 32:
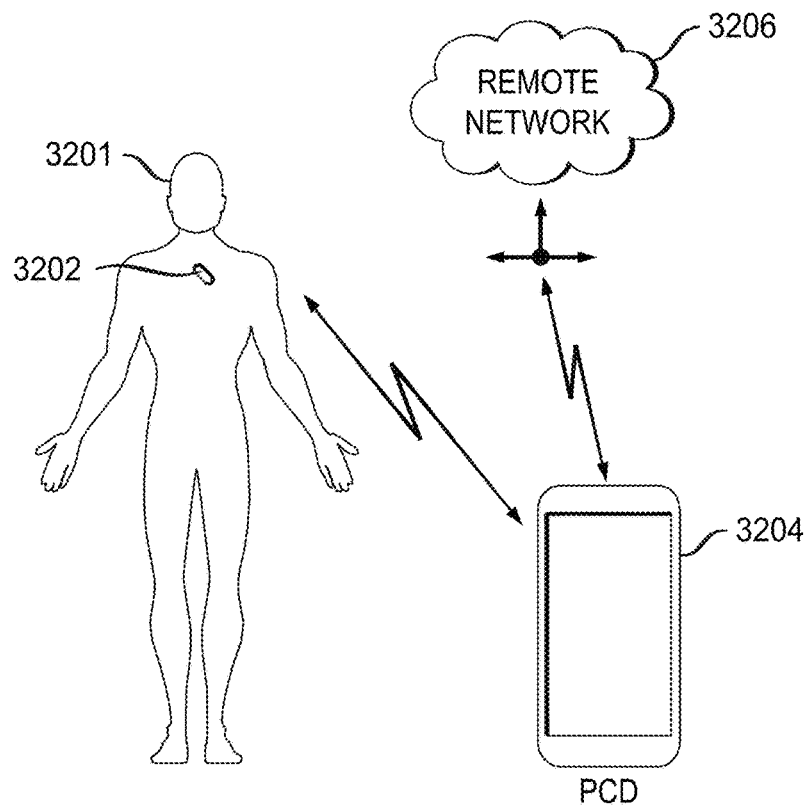
FIG. 32 illustrates communications in a modular physiologic monitoring system, according to an embodiment of the invention.

FIG. 32 shows an example modular physiologic monitoring system, illustrating a structure for communicating to a remote server (shown as remote network 3206) through a PCD 3204 configured for communication with a sensing/stimulating device 3202 on subject 3201. The sensing/stimulating device 3202 may be implemented as a patch/module pair 3202.

Figure 33:
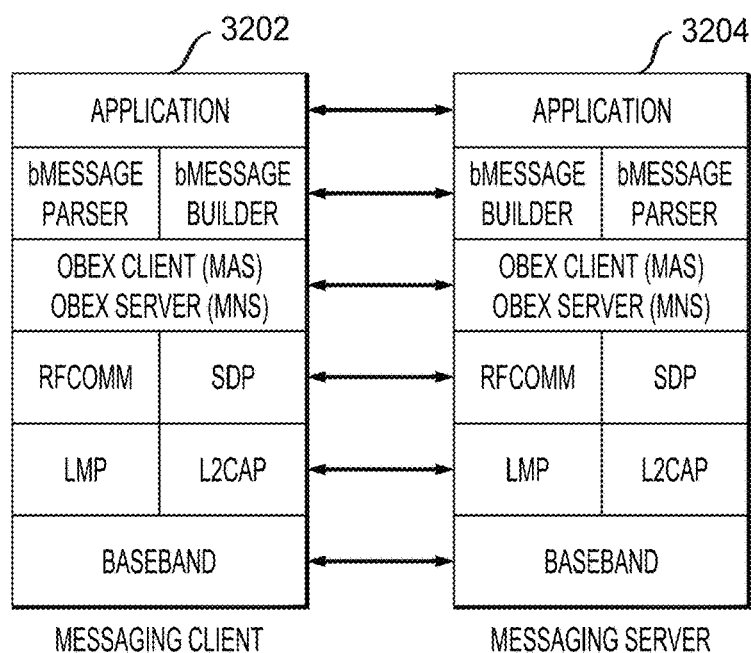
FIG. 33 illustrates a profile stack used for communications in a modular physiologic monitoring system, according to an embodiment of the invention.

FIG. 33 shows an example profile stack for communication between the patch-module pair 3202 and the PCD 3204. In this embodiment, the patch-module pair 3202 acts as the messaging client, while the PCD 3204 acts as the messaging server. It is to be appreciated, however, that in certain communications the PCD 3204 may act as a messaging client while the patch-module pair 3202 acts as the messaging server. More generally, the profile stack shown in FIG. 33 may be used in a body area network (BAN) including multiple patch-module pairs and a host device such as PCD 3204. It is also to be appreciated that while a BLE profile stack is illustrated, various other protocols including other types of short-range wireless communication protocols may be used in other embodiments. Each of the PCD 3204 and the remote server 3202 implements a profile stack including a baseband, a link manager protocol (LMP), a logical link control and adaptation protocol (L2CAP), radio frequency communication (RFCOMM), service discovery protocol (SDP), an object exchange (OBEX) client for message access service (MAS) and an OBEX server for message notification service (MNS), bMessage parser and bMessage builder application objects used by message access profile (MAP) for message transport and an application.

While FIGS. 32 and 33 illustrate an example implementation with a single patch-module pair 3202, in other embodiments multiple patch-module pairs may be used in a common BAN. Each patch-module pair may be configured for direct communication with the PCD 3204, such as using a BLE or other Bluetooth or short-range wireless communication protocol. In some embodiments, the patch-module pairs may also or alternatively be configured for communication with one another via a mesh network. The remote link between the PCD 3204 and the remote server 3206 may utilize a different type of network more suitable for long-range communication.

While FIG. 33 shows an example of profile stacks built in accordance with a Bluetooth protocol, communications between the PCD 3204 and the remote server 3202 may be over various types of wireless networks, including cellular networks, non-cellular networks such as satellite communication, etc. The selection of the type of wireless communication used may be based, at least in part, on a tradeoff between battery life and ease of communication with optimal wearability in the field.

Modular physiologic monitoring systems described herein may be used in a number of application areas, including with various types of end users. Examples of end users include but are not limited to incident responders (e.g., military officers, troops, police officers, fireman, dignitaries, physiotherapists, in military training, etc.). Modular physiologic monitoring systems as described herein provide approaches for physiological monitoring and/or management which is precise and user friendly (e.g., comfortable, long-term wearable, etc.) and cost optimal. In some embodiments, metrics relating to autonomic activity derived from precise cardiac monitoring permit modular physiologic monitoring systems to allow for new ways to quantitatively assess, monitor and treat subjects in a wide variety of application areas including but not limited to post-traumatic stress disorder (PTSD), depression, anxiety disorders, traumatic brain injury (TBI), situational awareness, training, medication management, etc.

Modular physiologic monitoring systems may be provide a number of benefits and advantages. In some embodiments, a robust design is provided via patch-module pairs including hubs/modules that are waterproof and sealed, with firm attachment and durable adhesion to a patch and via the patch to the subject, thus leading to user benefits in that the patch-module pairs stay attached to the subject in extreme circumstances and environments. The patch-module pairs are also easy to use, in that the patch may be as easy to apply, remove and replace as a standard bandage, thus fitting into a subject's daily workflow without interfering with daily routines. The patch-module pairs are also comfortable, in that they are lightweight and include highly stretchable and breathable membranes that are similar to skin and unobtrusive, and thus are suitable for long-term wear without the subject feeling that the patch-module pairs are being worn.

In some embodiments, modular physiologic monitoring systems provide benefits of robust data, in that patch-module pairs are configured for multi-modal data collection including via use of secondary sensors as described above, thus providing increased confidence in data and more accurate assessments of user status. Physical attachment of patch-module pairs may be hidden or visible, with the subtle physical profile of patch-module pairs allowing for strategic application to the subject for quality data and improved data confidence, which may reduce the risk of false alarms and incorrect data.

Modular physiologic monitoring systems also provide benefits for long-term measurements, such as continuous monitoring and feedback for chronic wear, providing hot-swappable hubs/modules, etc. thus fitting long-term usage scenarios including military operations.

In some embodiments, cost of ownership benefits are provided, in that the modular physiologic monitoring system may utilize patch-module pairs with cost effective combinations of durable and disposable components, suitable for widespread usage including in military ruggedized International Traffic in Arms Regulations (ITAR) stock-keeping unit (SKU).

Modular physiologic monitoring systems may also provide secure data through secure data transmission such as that conformable with Systems and Network Attack Center (SNaC) and Department of Defense (DoD) security guidelines.

Data quality benefits may also be provided via reliable data collection, precise physiological data measurement and confidence metrics, thus allowing for high confidence in data accuracy even in extreme usage scenarios.

Versatile data and versatile software may also be provided in some embodiments. Patch-module pairs may be used for robust and redundant data collection, providing fail-safes to continue collecting data during fault or compromised usage scenarios. Versatile software provides proactive monitoring, user interfaces for event registration, on-going continuous feedback, fallback storage during network downtime, etc. thus allowing for collection of data during down times, during user identified alerts and events, etc.

It will be appreciated that additional advantages and modifications will readily occur to those skilled in the art. Therefore, the disclosures presented herein and broader aspects thereof are not limited to the specific details and representative embodiments shown and described herein. Accordingly, many modifications, equivalents, and improvements may be included without departing from the spirit or scope of the general inventive concept as defined by the appended claims and their equivalents.

What is claimed is:

1. An apparatus comprising:
a processor; and
a memory coupled to the processor;
the processor being configured:
to receive monitoring data from at least one sensing device coupled to a subject;
to analyze the monitoring data to identify one or more physiologic parameters of the subject;
to provide signaling to at least one stimulating device in response to the identified physiologic parameters, the signaling comprising instructions for controlling a stimulus applied to the subject;
wherein analyzing the monitoring data comprises detecting one or more measured values of physiologic parameters indicating that an event is likely to occur; and
wherein the stimulus is controlled to reduce a likelihood that the event will occur.

2. The apparatus of claim 1, wherein the apparatus comprises a host device wirelessly coupled to the sensing device and the stimulating device.

3. The apparatus of claim 1, wherein the signaling comprises instructions for controlling at least one of a type, a duration, and an amount of the stimulus applied to the subject to effect one or more changes in the identified physiologic parameters.

4. The apparatus of claim 1, wherein the stimulus comprises an electrical stimulus.

5. The apparatus of claim 4, wherein the electrical stimulus comprises application of a pulse train.

6. The apparatus of claim 5, wherein the pulse train comprises two or more pulses having duration and charge delivery sufficient to stimulate tactile sensation while limiting pain fiber stimulation.

7. The apparatus of claim 5, wherein the signaling comprises instructions for controlling at least one of: a duration of at least one pulse in the pulse train; and a total charge of the at least one pulse in the pulse train.

8. The apparatus of claim 5, wherein the pulse train when applied to the subject mimics another stimulus, the other stimulus comprising at least one of vibration, pain, a wet sensation, heat or cold, taste, tension or stretch, sound, pressure and light.

9. The apparatus of claim 5, wherein the pulse train is applied to the subject to amplify another stimulus, the other stimulus comprising at least one of vibration, pain, a wet sensation, heat or cold, taste, tension or stretch, sound pressure and light.

10. An apparatus comprising:
a processor; and
a memory coupled to the processor;
the processor being configured:
to receive monitoring data from at least one sensing device coupled to a subject
to analyze the monitoring data to identify one or more physiologic parameters of the subject;
to provide signaling to at least one stimulating device in response to the identified physiologic parameters, the signaling comprising instructions for controlling a stimulus applied to the subject;
wherein analyzing the monitoring data comprises detecting one or more measured values of physiologic parameters indicating that an event is likely to occur;
wherein the stimulus is controlled to reduce a likelihood that the event will occur;
wherein the event comprises a sleep apneic event; and
wherein the stimulus is applied to a plantar aspect of a foot of the subject.

11. An apparatus comprising:
a processor; and a memory coupled to the processor;
the processor being configured:
- to receive monitoring data from at least one sensing device coupled to a subject;
- to analyze the monitoring data to identify one or more physiologic parameters of the subject;
- to provide signaling to at least one stimulating device in response to the identified physiologic parameters, the signaling comprising instructions for controlling a stimulus applied to the subject;

wherein analyzing the monitoring data comprises detecting one or more measured values of physiologic parameters indicating that an event is likely to occur;

wherein the stimulus is controlled to reduce a likelihood that the event will occur;

wherein the event comprises determining a sleep posture of the subject; and wherein the stimulus is controlled to alter the sleep posture of the subject.

12. The apparatus of claim 1, wherein the sensing device and the stimulating device are physically distinct.

13. The apparatus of claim 1, wherein the at least one sensing device comprises a first sensing device at a first location on the subject and a second sensing device at a second location on the subject different than the first location.

14. The apparatus of claim 13, wherein the first sensing device is configured to measure a first physiologic parameter of the subject at the first location and the second sensing device is configured to measure a second physiologic parameter different than the first physiologic parameter at the second location.

15. The apparatus of claim 13, wherein the first sensing device and the second sensing device are configured to measure a same physiologic parameter at the first location and the second location.

16. The apparatus of claim 1, wherein the at least one stimulating device comprises a first stimulating device at a first location on the subject and a second stimulating device at a second location on the subject different than the first location.

17. The apparatus of claim 16, wherein the signaling comprises instructions:
- to apply a first stimulus utilizing the first stimulating device at the first location; and
- to apply a second stimulus different than the first stimulus utilizing the second stimulating device at the second location.

18. The apparatus of claim 1, wherein the at least one stimulating device is integrated into a surface configured for contact with the subject.

19. The apparatus of claim 1, wherein the at least one stimulating device is integrated into a device not contacting the subject.

20. The apparatus of claim 1, wherein the at least one stimulating device comprises:
- a disposable component configured to conform to an anatomy of the subject and comprising one or more electrodes configured to apply a stimulus to the subject; and
- a reusable component configured to interface with the disposable component, to receive the signaling, and to direct the one or more electrodes to apply the stimulus in response to the signaling.

* * * * *